(12) United States Patent
Waag et al.

(10) Patent No.: US 11,844,648 B2
(45) Date of Patent: Dec. 19, 2023

(54) DEVICE, SYSTEM, AND METHOD FOR HEMISPHERIC BREAST IMAGING

(71) Applicant: Habico, Inc., Honey Falls, NY (US)

(72) Inventors: Robert C. Waag, Buffalo, NY (US); Jeffrey P. Astheimer, Honey Falls, NY (US)

(*) Notice: Subject to any disclaimer, the term of this patent is extended or adjusted under 35 U.S.C. 154(b) by 0 days.

(21) Appl. No.: 17/507,319

(22) Filed: Oct. 21, 2021

(65) Prior Publication Data

US 2022/0175341 A1    Jun. 9, 2022

Related U.S. Application Data

(63) Continuation of application No. 15/501,792, filed as application No. PCT/US2015/043628 on Aug. 4, 2015, now Pat. No. 11,191,519.

(Continued)

(51) Int. Cl.
*A61B 8/00* (2006.01)
*A61B 8/08* (2006.01)
(Continued)

(52) U.S. Cl.
CPC .............. *A61B 8/14* (2013.01); *A61B 8/08* (2013.01); *A61B 8/0825* (2013.01); *A61B 8/406* (2013.01); *A61B 8/4281* (2013.01); *A61B 8/4483* (2013.01); *A61B 8/4494* (2013.01); *A61B 8/483* (2013.01); *A61B 8/5207* (2013.01);
(Continued)

(58) Field of Classification Search
CPC ......... A61B 8/14; A61B 8/0825; A61B 8/406; A61B 8/4483; A61B 8/4494; A61B 8/483; A61B 8/5207; G01S 15/8959
See application file for complete search history.

(56) References Cited

U.S. PATENT DOCUMENTS 4,052,723 A   10/1977  Miller
4,452,081 A    6/1984  Seppi
(Continued)

FOREIGN PATENT DOCUMENTS

WO    2002082669 A2    10/2002

OTHER PUBLICATIONS

J. A. Jensen et al., "SARUS: A synthetic aperture real-time ultrasound system," in IEEE Transactions on Ultrasonics, Ferroelectrics, and Frequency Control, vol. 60, No. 9, pp. 1838-1852, Sep. (Year: 2013).*

(Continued)

*Primary Examiner* — Shahdeep Mohammed
*Assistant Examiner* — Amal Aly Farag
(74) *Attorney, Agent, or Firm* — Blank Rome LLP

(57) ABSTRACT

A device, system, and method for volumetric ultrasound imaging is described. The device and system include an array of transducer elements grouped in triangular planar facets and substantially configured in the shape of a hemisphere to form a cup-shaped volumetric imaging region within the cavity of the hemisphere, A plurality of data-acquisition assemblies are connected to the transducers, which are configured to collect ultrasound signals received from the transducers and transmit image data to a network of processors that are configured to construct a volumetric image of an object within the imaging region based on the image data received from the data-acquisition assemblies.

20 Claims, 25 Drawing Sheets

Related U.S. Application Data

(60) Provisional application No. 62/033,313, filed on Aug. 5, 2014.

(51) Int. Cl.
  *A61B 8/14* (2006.01)
  *A61B 8/15* (2006.01)
  *G01S 15/89* (2006.01)

(52) U.S. Cl.
  CPC ........ *A61B 8/5269* (2013.01); *G01S 15/8915* (2013.01); *G01S 15/8929* (2013.01); *G01S 15/8977* (2013.01); *G01S 15/8993* (2013.01); *G01S 15/8959* (2013.01)

(56) References Cited

U.S. PATENT DOCUMENTS

| | | |
|---|---|---|
| 4,662,222 A | 5/1987 | Johnson |
| 5,042,492 A | 8/1991 | Dubut |
| 5,305,752 A | 4/1994 | Spivey et al. |
| 5,365,929 A | 11/1994 | Peterson |
| 5,428,999 A | 7/1995 | Fink |
| 5,588,032 A | 12/1996 | Johnson et al. |
| 5,591,911 A | 1/1997 | Masuzawa et al. |
| 5,964,709 A | 10/1999 | Chiang et al. |
| 6,013,032 A | 1/2000 | Savord |
| 6,102,860 A | 8/2000 | Mooney |
| 6,345,194 B1 | 2/2002 | Nelson et al. |
| 6,436,040 B1 | 8/2002 | Collamore et al. |
| 6,478,739 B1 * | 11/2002 | Hong ............... A61B 8/0825 128/915 |
| 6,503,204 B1 | 1/2003 | Sumanaweera et al. |
| 6,613,004 B1 | 9/2003 | Vitek et al. |
| 6,981,417 B1 | 1/2006 | Oravecz |
| 7,018,334 B2 | 3/2006 | Israel |
| 7,652,410 B2 | 1/2010 | Prus |
| 7,864,846 B2 | 1/2011 | Chujoh et al. |
| 8,608,672 B2 | 12/2013 | Vortman et al. |
| 2001/0031922 A1 | 10/2001 | Weng et al. |
| 2001/0032511 A1 | 10/2001 | Nagai et al. |
| 2002/0045830 A1 | 4/2002 | Powers et al. |
| 2002/0188198 A1 | 12/2002 | Hong |
| 2003/0023168 A1 | 1/2003 | Benjamin |
| 2003/0149357 A1 | 8/2003 | Liu |
| 2003/0214379 A1 | 11/2003 | Satoh et al. |
| 2004/0068184 A1 | 4/2004 | Trahey et al. |
| 2004/0081273 A1 | 4/2004 | Ning |
| 2004/0254464 A1 | 12/2004 | Stribling |
| 2005/0007882 A1 | 1/2005 | Bachelor et al. |
| 2005/0096515 A1 | 5/2005 | Geng |
| 2005/0143638 A1 | 6/2005 | Johnson et al. |
| 2005/0203370 A1 | 9/2005 | Patch |
| 2006/0064012 A1 | 3/2006 | Waag et al. |
| 2007/0106157 A1 | 5/2007 | Kaczkowski et al. |
| 2007/0208254 A1 | 9/2007 | Johnson et al. |
| 2007/0268287 A1 | 11/2007 | Magnin et al. |
| 2007/0282200 A1 | 12/2007 | Johnson et al. |
| 2008/0187095 A1 | 8/2008 | Boone et al. |
| 2008/0273424 A1 * | 11/2008 | Wodnicki ............. A61B 8/0833 257/E27.107 |
| 2008/0294046 A1 | 11/2008 | Chiang et al. |
| 2008/0319318 A1 | 12/2008 | Johnson et al. |
| 2009/0043206 A1 | 2/2009 | Towfiq et al. |
| 2009/0066727 A1 | 3/2009 | Lu et al. |
| 2009/0171217 A1 | 7/2009 | Kim et al. |
| 2009/0230823 A1 * | 9/2009 | Kushculey ............. B06B 1/0637 310/366 |
| 2010/0036244 A1 | 2/2010 | Angelsen et al. |
| 2010/0113921 A1 | 5/2010 | Fear et al. |
| 2010/0172469 A1 | 7/2010 | Poulsen et al. |
| 2010/0174189 A1 | 7/2010 | Abraham |
| 2010/0186017 A1 | 7/2010 | Eeratta et al. |
| 2010/0195881 A1 | 8/2010 | Orderud et al. |
| 2010/0298688 A1 | 11/2010 | Dogra et al. |
| 2010/0305449 A1 | 12/2010 | Wegener et al. |
| 2010/0328759 A1 | 12/2010 | Kirkby et al. |
| 2011/0083511 A1 | 4/2011 | Taki et al. |
| 2011/0227934 A1 | 9/2011 | Sharp |
| 2011/0295119 A1 | 12/2011 | Miller et al. |
| 2011/0306865 A1 | 12/2011 | Thornton et al. |
| 2012/0179044 A1 | 7/2012 | Chiang et al. |
| 2012/0271165 A1 | 10/2012 | Liu et al. |
| 2013/0310679 A1 | 11/2012 | Natarajan et al. |
| 2013/0044924 A1 | 2/2013 | Spencer |
| 2013/0060140 A1 | 3/2013 | Sinelnikov |
| 2013/0116561 A1 | 5/2013 | Rothberg et al. |
| 2013/0168532 A1 | 7/2013 | Schmid et al. |
| 2013/0172752 A1 | 7/2013 | Hu et al. |
| 2013/0197366 A1 | 8/2013 | Rigby et al. |
| 2013/0251222 A1 | 9/2013 | Huang |
| 2013/0253322 A1 | 9/2013 | Suzuki et al. |
| 2013/0267850 A1 | 10/2013 | Berman |
| 2013/0303895 A1 | 11/2013 | Littrup et al. |
| 2013/0312526 A1 | 11/2013 | Oishi |
| 2013/0336551 A1 | 12/2013 | Clingman et al. |
| 2013/0338485 A1 | 12/2013 | Mougenot et al. |
| 2014/0043933 A1 | 2/2014 | Belevich et al. |
| 2014/0066769 A1 | 3/2014 | Wang |
| 2014/0135681 A1 | 5/2014 | Angelsen |
| 2014/0180105 A1 | 6/2014 | Hancock et al. |
| 2014/0180128 A1 | 6/2014 | Corl |
| 2014/0187903 A1 | 7/2014 | Oyama et al. |
| 2014/0243614 A1 | 8/2014 | Rothberg et al. |
| 2014/0288415 A1 | 9/2014 | Forzoni et al. |
| 2014/0309527 A1 | 10/2014 | Namati et al. |
| 2016/0106395 A1 | 4/2016 | Hynynen et al. |
| 2016/0113632 A1 | 4/2016 | Ribes et al. |
| 2016/0310111 A1 | 10/2016 | Cho et al. |
| 2019/0000423 A1 | 1/2019 | Watanabe |
| 2019/0183347 A1 | 6/2019 | Hirata |
| 2019/0239860 A1 | 8/2019 | Hayashi et al. |
| 2019/0246941 A1 | 8/2019 | Bannister et al. |
| 2020/0008784 A1 | 1/2020 | Yamanaka et al. |
| 2020/0038694 A1 | 2/2020 | Theuer |

OTHER PUBLICATIONS

W. Jiang, "Ultrasound Focusing by Use of Aperture with Different Pitches and Ultrasound Imaging by Use of a Hemispheric Transducer Array", University of Rochester, NY 2011; 151 pages.

Garland, et al., "Parallel Computing Experiences with CUDA", IEEE Micro, IEEE Service Center, Los Alamitos, CA, US. vol. 28, No. 4, Jul. 2008; pp. 13-27.

Jaros et al., "Use of multiple GPUs on shared memory multiprocessors for ultrasound propagation simulations", Australian Computer Society, Inc., Jan. 30, 2012, pp. 43-52.

Hersford et al., "Fast inverse scattering solutions using the distorted Born iterative method and the multilevel fast multipole algorithm", The Journal of the Acoustical Society of America, American Institute of Physics for the Acoustical Society of America, New York, NY US, vol. 128, No. 2, Aug. 1, 2010, pp. 679-690.

Supplementary European Search Report of European Application No. 15782236.2; 3 pages.

F. Simonetti et al., "A multiscale approach to diffraction tomography of complex three-dimensional objects", Applied. Physical Letters 95, 061904 (2009); https://doi.org/10.1063/1.3204021.

F. Simonetti et al., "Diffraction and coherence in breast ultrasound tomography: A study with a toriodal array", Medical Physics 36(7), 2955-2965, Jul. 2009.

Bryan Ranger et al., "Breast Ultrasound Tomography Versus MRI for Clinical Display of Anatomy and Tumor Rendering: Preliminary Results", www.ajronline.org, AJR:198, Jan. 2012.

Bryan Ranger et al., "Breast imaging with acoustic tomography: a comparative study with MRI", https://proceedings.spiedigitallibrary.org/conference-proceedings-of-spie, 2009.

\* cited by examiner

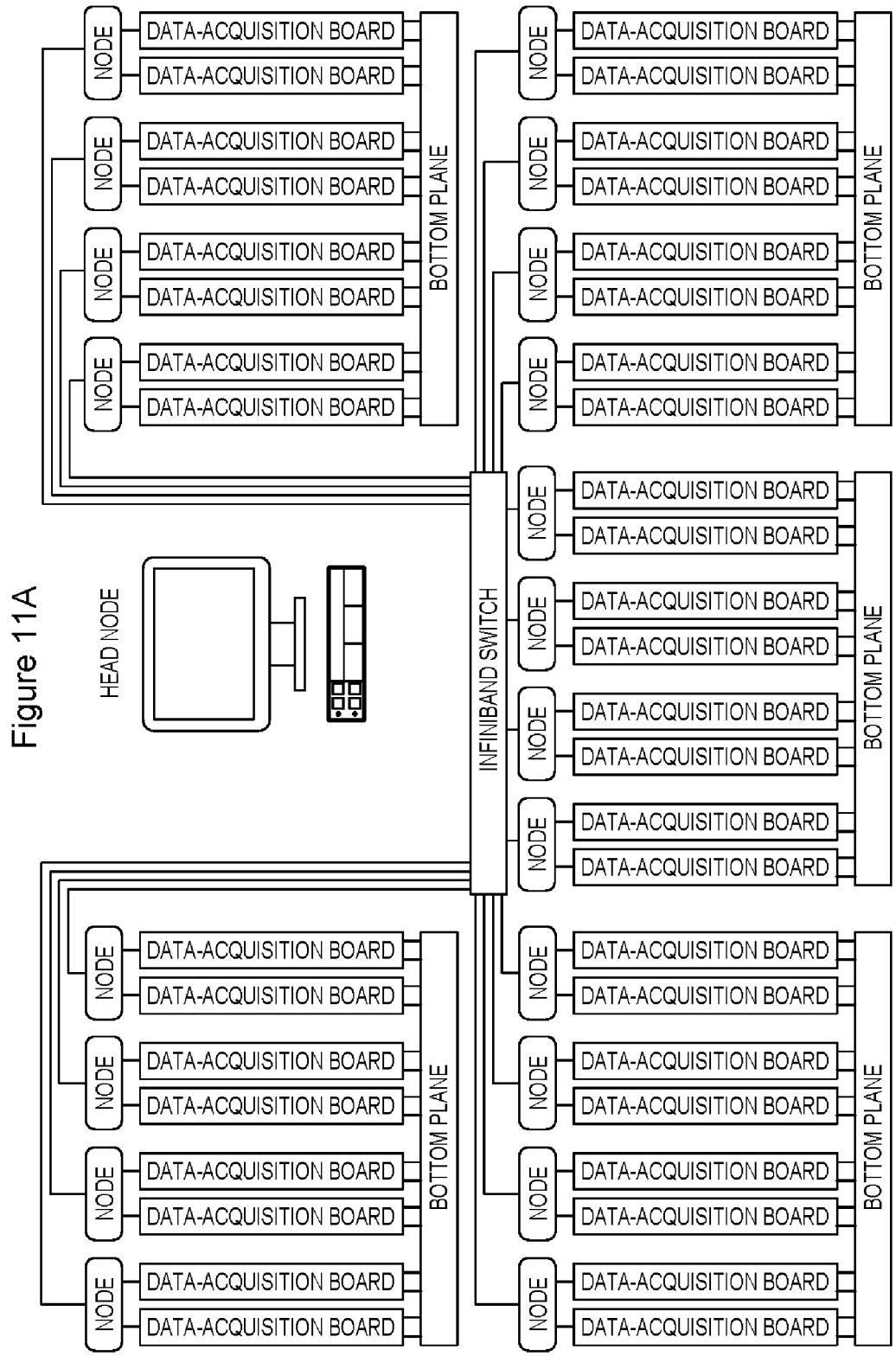

DEVICE, SYSTEM, AND METHOD FOR HEMISPHERIC BREAST IMAGING

RELATED APPLICATIONS

This application is a continuation of co-pending U.S. patent application Ser. No. 15/501,792, filed Feb. 3, 2017, which is a national stage application of PCT Pat. Appl. No. PCT/US2015/043628, filed Aug. 4, 2015, which claims priority to U.S. Prov. Pat. Appl. No. 62/033,313, filed Aug. 5, 2014. The entire contents of the aforementioned patent applications are hereby incorporated by reference.

STATEMENT REGARDING FEDERALLY SPONSORED RESEARCH OR DEVELOPMENT

This invention was made with government support under Grant Nos. EB009692 and EB010069 awarded by the National Institutes of Health (NIH). The government has certain rights in the invention.

BACKGROUND

Breast cancer is a significant health problem worldwide. In the United States alone, more than 230,000 new cases of invasive breast cancer are estimated to be diagnosed each year and about 40,000 women are expected die of the disease this year. Globally, when excluding non-melanoma cancers of the skin, breast cancer is the most common cancer in women.

An important clinical goal is to detect breast masses when they are as small as possible, preferably less than several millimeters in diameter. Reports indicate that women who have invasive breast cancer detected when the size is less than 15 mm have a 15-year survival rate of 89-93% (95% confidence interval). Imaging is the primary way that cancer in the breast can be detected when the cancer is small. In addition, imaging can also be used for staging and monitoring response to the treatment of a patient with breast cancer.

The breast can be imaged using a number of methods, including conventional x-ray mammography, x-ray tomosynthesis, and magnetic resonance imaging (MRI). However, current implementations of these methods often suffer from low resolution, poor contrast, or other issues that reduce the effectiveness of these techniques in detecting or identifying breast disease.

For example, X-ray mammography is generally considered to be the most cost-effective tool for the early detection of breast cancer. However, the specificity and positive predictive value of mammography is limited, due to the potential overlap in the appearances of benign and malignant lesions, and to poor contrast in patients with dense breast tissue.

Ultrasound is not typically used for the diagnosis of breast disease because the process of obtaining the images is highly operator dependent. Further, ultrasound resolution is generally not adequate, particularly in the direction orthogonal to the imaging plane, i.e., the slice thickness dimension, and speckle can make images hard to interpret or can obscure calcifications. Current ultrasound techniques also often poorly describe lesion margins that are known to be an important feature for the diagnosis of cancer.

Accordingly, there is a continuing need in the art for imaging techniques that can be used to image breasts accurately for the purposes of detecting or identifying breast disease.

SUMMARY

In one embodiment, a device for volumetric ultrasound imaging is claimed. The device includes an array of ultrasound transducer elements substantially configured in the shape of a hemisphere to form a cup-shaped volumetric imaging region within the cavity of the hemisphere. In another embodiment, the array of transducers includes 40 triangular planar facets. In another embodiment, 10 of the facets are equilateral triangles and 30 of the facets are isosceles triangles. In another embodiment, each triangular transducers includes 256 piezoelectric elements. In another embodiment, the piezoelectric elements are arranged pseudorandomly on each facet. In another embodiment, at least one of the transducers further includes a diverging lens. In another embodiment, at least one of the transducers further includes two matching layers. In another embodiment, the hemisphere array of transducers is positioned within the surface of a patient table, such that the opening of the cup-shaped volumetric imaging region is substantially flush with the patient table surface. In another embodiment, the device further includes a cup-shaped container sized to fit substantially within the imaging region cavity of the hemisphere. In another embodiment, the cup-shaped container is disposable.

In another embodiment, a system for volumetric ultrasound imaging is claimed. The system includes an array of planar faceted ultrasound transducers substantially configured in the shape of a hemisphere to form a cup-shaped volumetric imaging region within the cavity of the hemisphere, a plurality of data-acquisition assemblies connected to the transducers, and a network of processors connected to the data-acquisition assemblies. The ultrasound transducers are configured to generate and receive ultrasound signals within the imaging region, the data-acquisition assemblies are configured to collect ultrasound signals received from the transducers and transmit measured data to the network of processors, and the network of processors is configured to construct a volumetric image of an object within the imaging region based on the image data received from the data-acquisition assemblies. In another embodiment, the number of data-acquisition assemblies is equal to the number of transducer elements, and that each data-acquisition assembly is dedicated to an individual transducer. In another embodiment, the array of transducers comprises 40 triangular planar faceted transducer subarrays. In another embodiment, 10 of the facets are equilateral triangles and 30 of the facets are isosceles triangles. In another embodiment, each transducer comprises 256 piezoelectric elements. In another embodiment, each data-acquisition assembly comprises at least 256 send/receive channels. In another embodiment, the network of processors comprises at least 20 nodes. In another embodiment, each node comprises at least one graphical processing unit (GPU). In another embodiment, each node is configured to process data received from at least two data-acquisition assemblies in parallel.

In another embodiment, a method for reconstructing a volumetric ultrasound image is claimed. The method includes the steps of generating ultrasound signals from an array of transducer elements substantially arranged in the shape of a hemisphere, such that the generated signals are incident on a scattering object positioned within the cavity formed by the hemisphere of transducer elements; measuring a plurality of scattered ultrasound signals with the ultrasound transducer elements; pre-processing the measured signals with a plurality of data-acquisition assemblies; and reconstructing a volumetric image of the scattering object with a network of processors based on the pre-processed signals. In one embodiment, the image of the scattering object is reconstructed via an inverse-scattering model.

In one embodiment, the image of the scattering object is reconstructed by relating the measured scattered ultrasound signals to background medium variation. In such an embodiment, an estimate image of the scattering object is reconstructed from a subset of the measured signals; one or more refined images of the scattering object are reconstructed from the estimate image of the scattering object and pre-processed signals; and the volumetric image of the scattering object is reconstructed from the one or more refined images and pre-processed signals. In one embodiment, the background medium variation is substantially linear in relation to the measured signals.

In one embodiment, at least a portion of the scattering object data is interpolated. In one such embodiment, the interpolation comprises a prefiltering step. In one embodiment, scattering measured in the hemisphere transducer array is used to estimate scattering object detail that would come from scattering in the antipodal hemisphere. In one embodiment, the measured signals are divided into overlapping subvolumes. In one embodiment, the subvolumes are tetrahedral. In one embodiment, the background medium variation of each subvolume is calculated independently. In one embodiment, the calculation of the background medium variation of each subvolume is processed substantially simultaneously. In one embodiment, an array of background medium variation values corresponding to the overlapping subvolumes is rotated during reconstruction. In one embodiment, the background medium variation array is rotated to align an axis of the background medium variation array with an axis of a portion of the transducer elements. In one embodiment, the rotation of the background medium variation array is factored into one or more skew operations. In one embodiment, virtual scattering measurements from the background medium variations are computed at the vertices of a regular grid that span the surface of each facet. In one embodiment, the virtual scattering measurement computations further comprise an inverse two-dimensional Fast Fourier transform of spatial frequency integrals. In one embodiment, the virtual scattering measurements are used to interpolate actual scattering measurements at the locations of the facet elements. In one embodiment, the interpolations further comprise a prefiltering step.

In one embodiment, an estimate image of the scattering object is reconstructed from a subset of the measured signals; one or more refined images of the scattering object are reconstructed from the estimate image and pre-processed signals corresponding to the overlapping subvolumes of measured signals; and a volumetric image of the scattering object is reconstructed from the one or more refined images and pre-processed signals corresponding to the overlapping subvolumes of measured signals.

In one embodiment, a time gate is applied to the measured signals prior to reconstruction to isolate the measured signals from different subvolumes.

BRIEF DESCRIPTION OF THE DRAWINGS

The following detailed description of embodiments will be better understood when read in conjunction with the appended drawings. It should be understood, however, that the embodiments are not limited to the precise arrangements and instrumentalities shown in the drawings.

FIG. 4, comprising FIG. 4A is a photo image of the inner surface of the transducer element subassembly, FIG. 4B is a cross-sectional X-ray image of a portion of the subassembly, and FIG. 4C is a photo image of the outer surface of the subassembly.

FIG. 11A is a schematic of an exemplary embodiment of a high-performance computer network communicatively connected to the hemispheric transducer array of a HABIS.

FIGS. 14 and 14B, is a diagram of the reconstruction of a 10-point resolution target (14A) and a corresponding b-scan of the target (14B). The surfaces shown are 50% of the maximum amplitude. The two upper-most points are 200 m apart, the two left-most points are 300 m apart, and the two right-most points are 400 m apart. In each panel, an edge of the cubic volume has a length of 2.9 mm and the tic increment on the axes is 0.5 mm.

Orthogonal relation between the subvolume sections, x-y plane at z=0, x-z plane at y=0, and y-z plane at x=0. Scattering throughout the hemisphere was used to estimate scattering obtained from a virtual array in the opposite hemisphere and then both sets of data were used in the inverse scattering reconstruction. The b-scan used reception from a 64-element subtriangle and used transmission from that 64-element subtriangle and three surrounding 64-element subtriangles to allow quick formation of a volumetric image. In each panel, an edge of the section has a length of 6.4 mm, and the outer region of the section is weighted by a window used to blend adjacent reconstructed subvolumes. The x, y, and z axes are denoted accordingly. The z axis is the polar axis of the hemisphere, the approximate direction of the b-scan lines which mainly highlight discontinuities perpendicular to them. The original subvolume and the reconstructed subvolume are shown on a linear scale and the b-scan is shown on a log scale.

Figure 16:
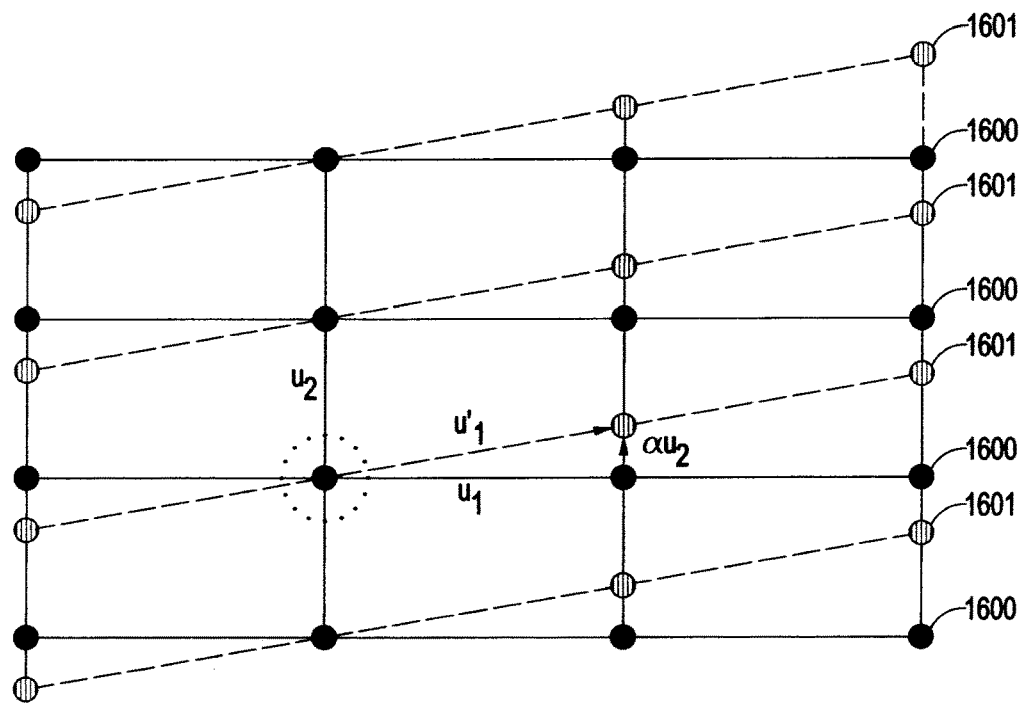

FIG. 16 illustrates coordinate transformation produced by skewing the horizontal generating vector.

Figure 17:
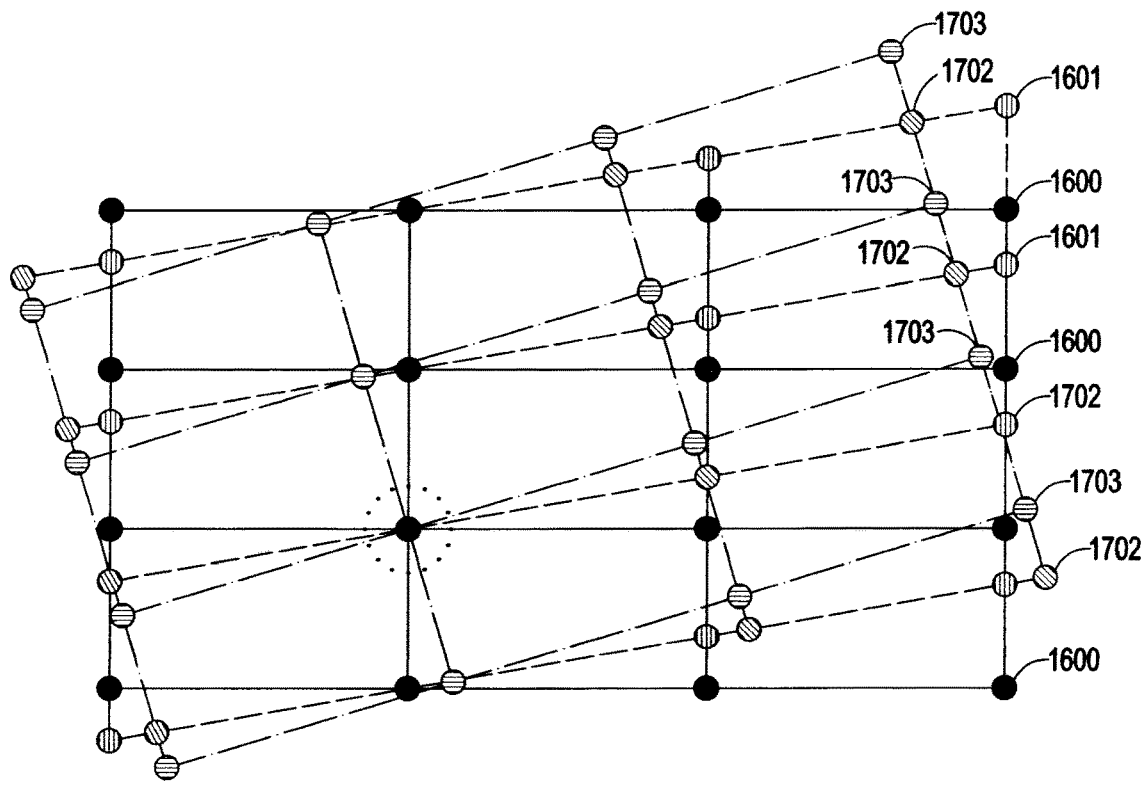

FIG. 17 illustrates three skew transformations that yield a rotated coordinate system.

Figure 18:
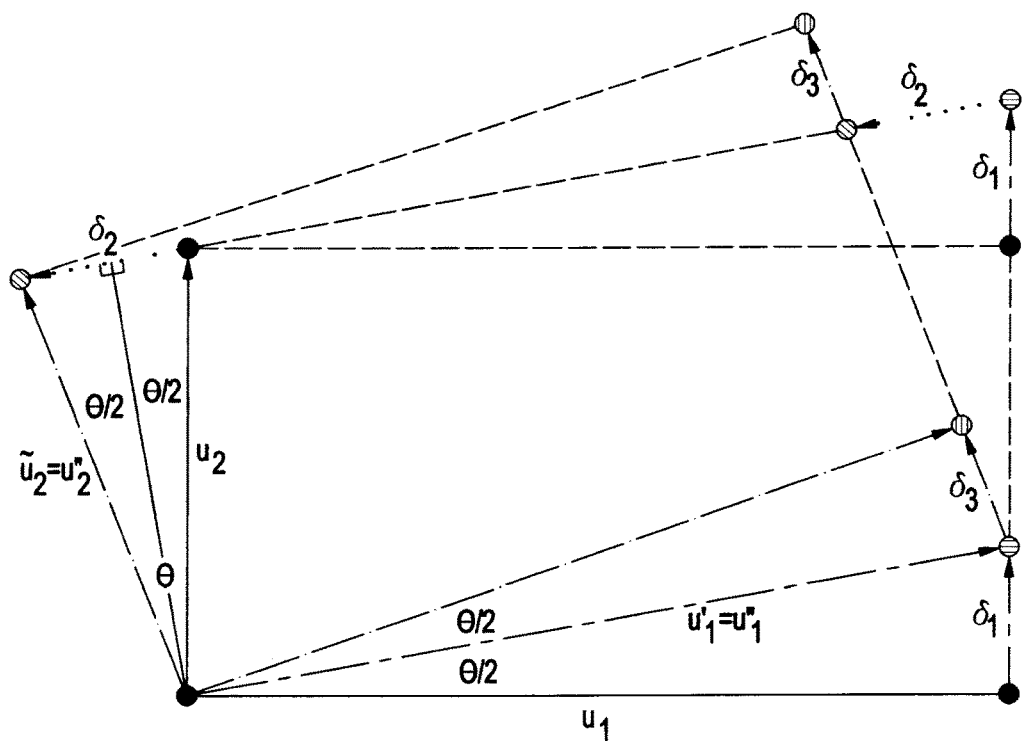

FIG. 18 illustrates geometry used to determine skews that result in a θ rotation.

Figure 19:
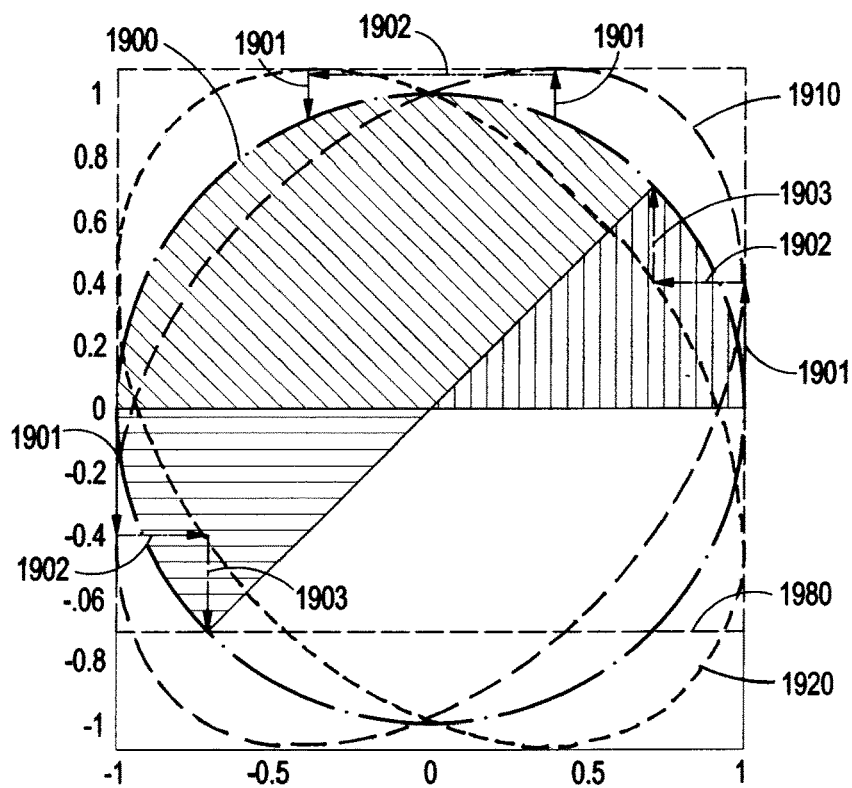

FIG. 19 illustrates geometry of array size requirements for in-place rotation.

Figure 20:
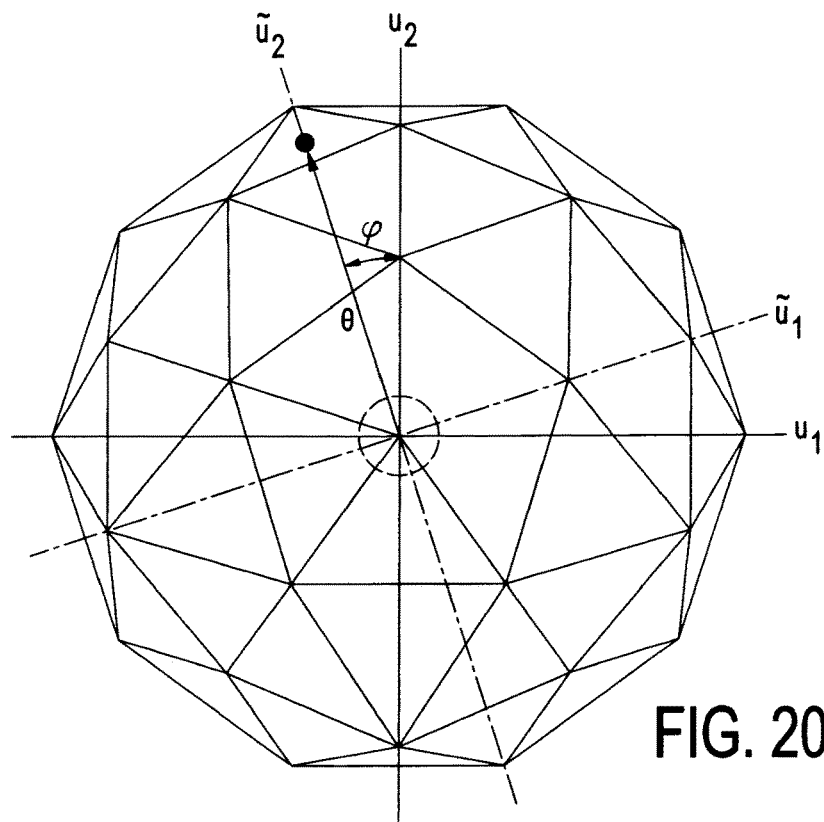

FIG. 20 illustrates planar rotations $R_\theta^2 R_\phi^3$ satisfy $R_\theta^2 R_\phi^3 u_3 = \sin\theta \cos\phi u_1 + \sin\theta \sin\phi u_2 + \cos\phi u_3$.

Figure 21:
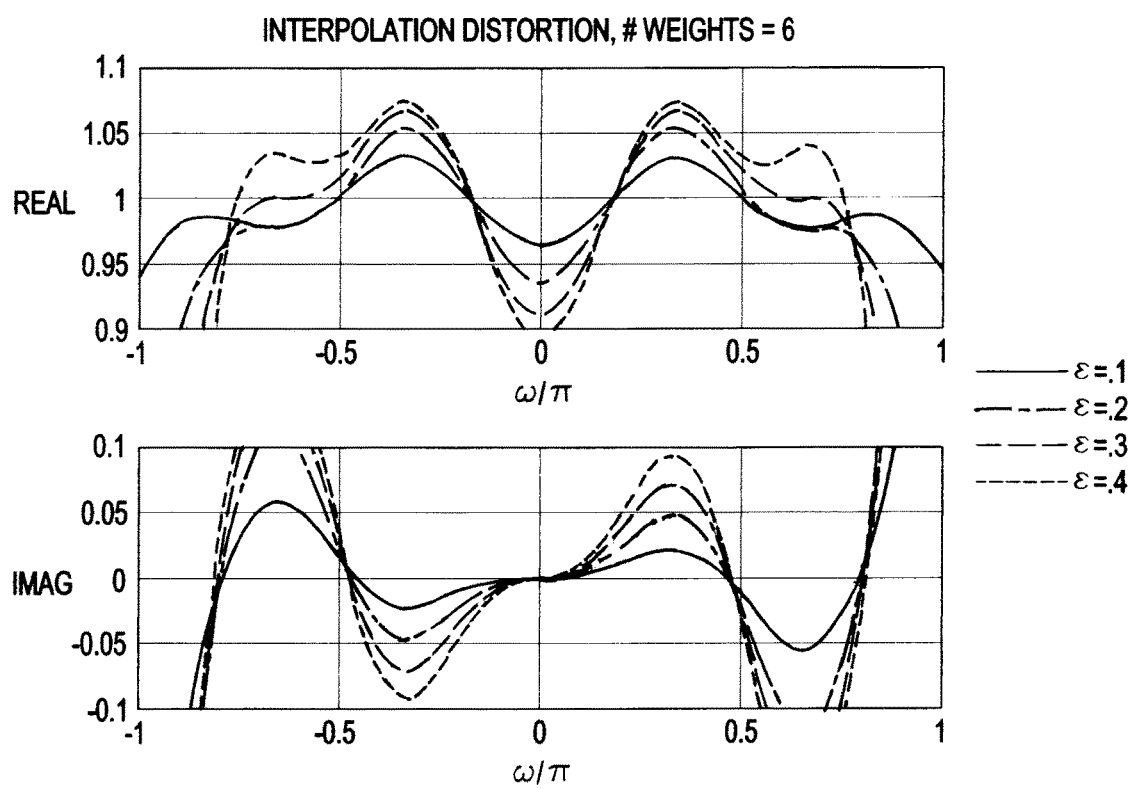

FIG. 21 illustrates distortion curves of interpolations at fractional offsets of 0.1, 0.2, 0.3, and 0.4 using coefficients giving minimum least-square error in the frequency band $[-\pi, +\pi]$. The interpolation filter has coefficients.

Figure 22:
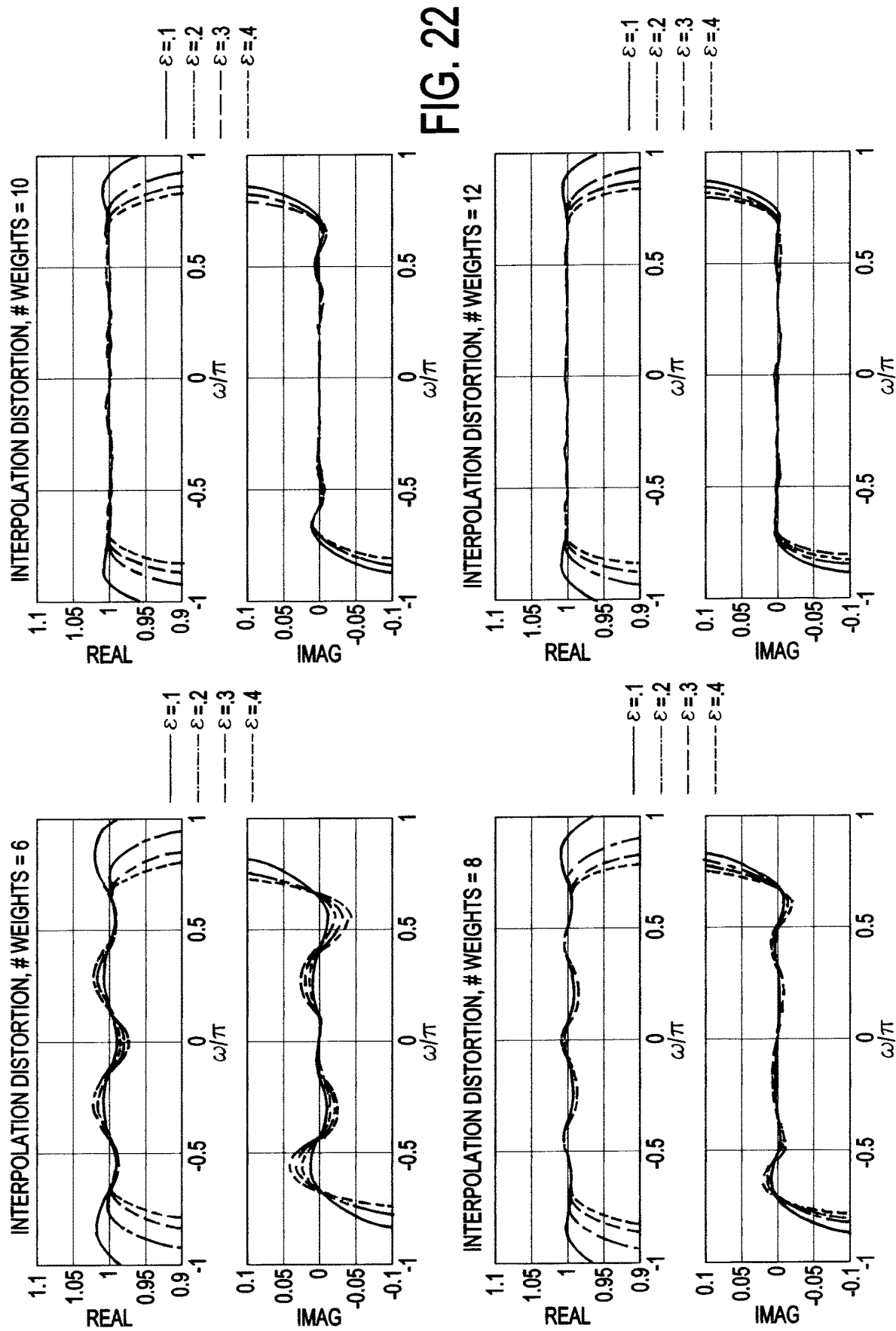

FIG. 22 illustrates distortion curves of interpolations at fractional offsets of 0.1, 0.2, 0.3 and 0.4 using coefficients giving minimum least-square error in the frequency band $[-0.75\pi, +0.75\pi]$ The four panels show the distortion for interpolation filters with 6 (upper left), 8 (upper right), 10 (lower left) and 12 (lower right) coefficients.

Figure 23:
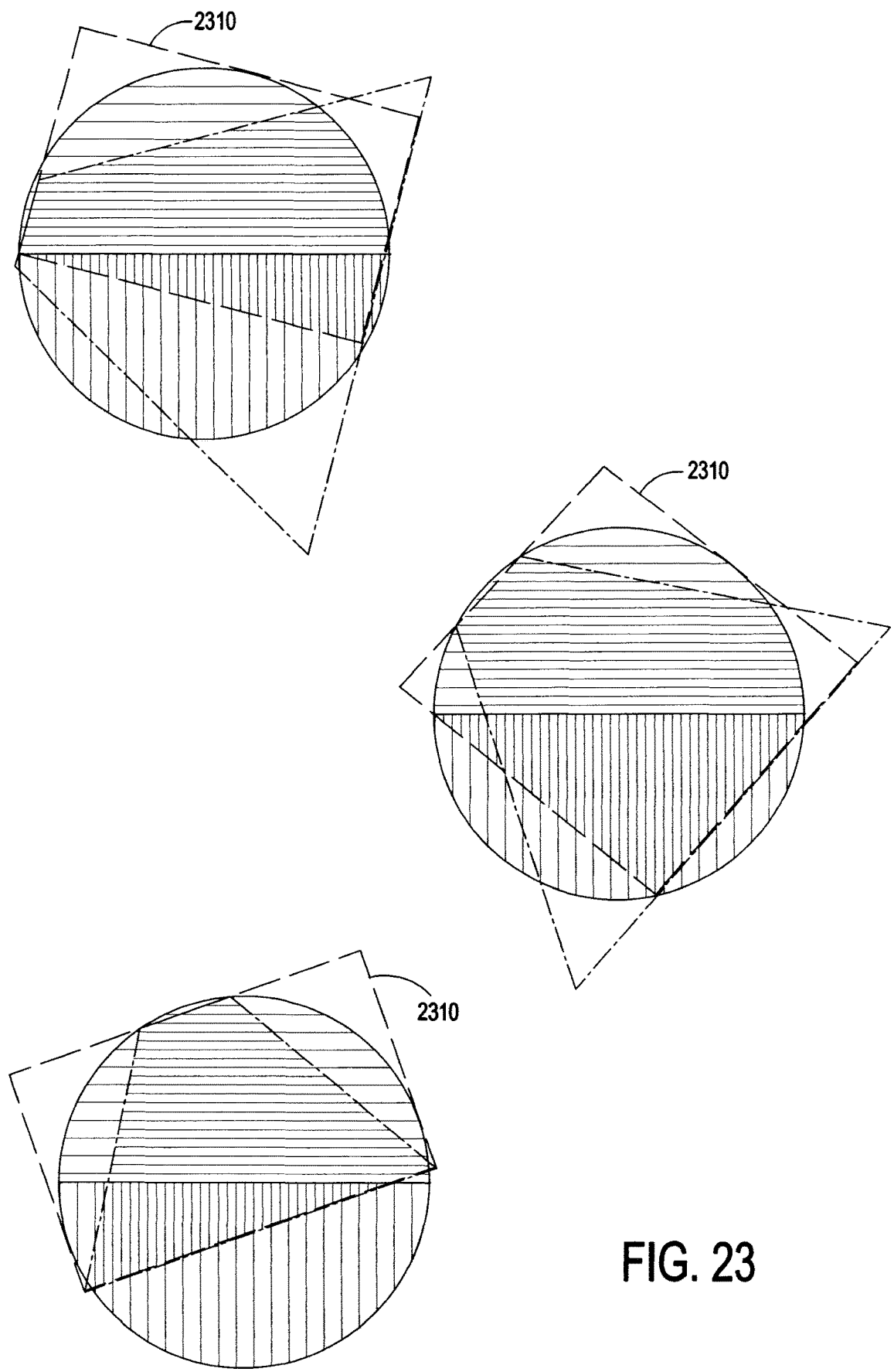

FIG. 23 illustrates rectangular boundaries of forward solutions from transmit elements in a facet that contain the upper hemisphere (dotted rectangles) and the additional boundaries associated with the directivity patterns of all the elements in the facet (trapezoidal regions).

Figure 24:
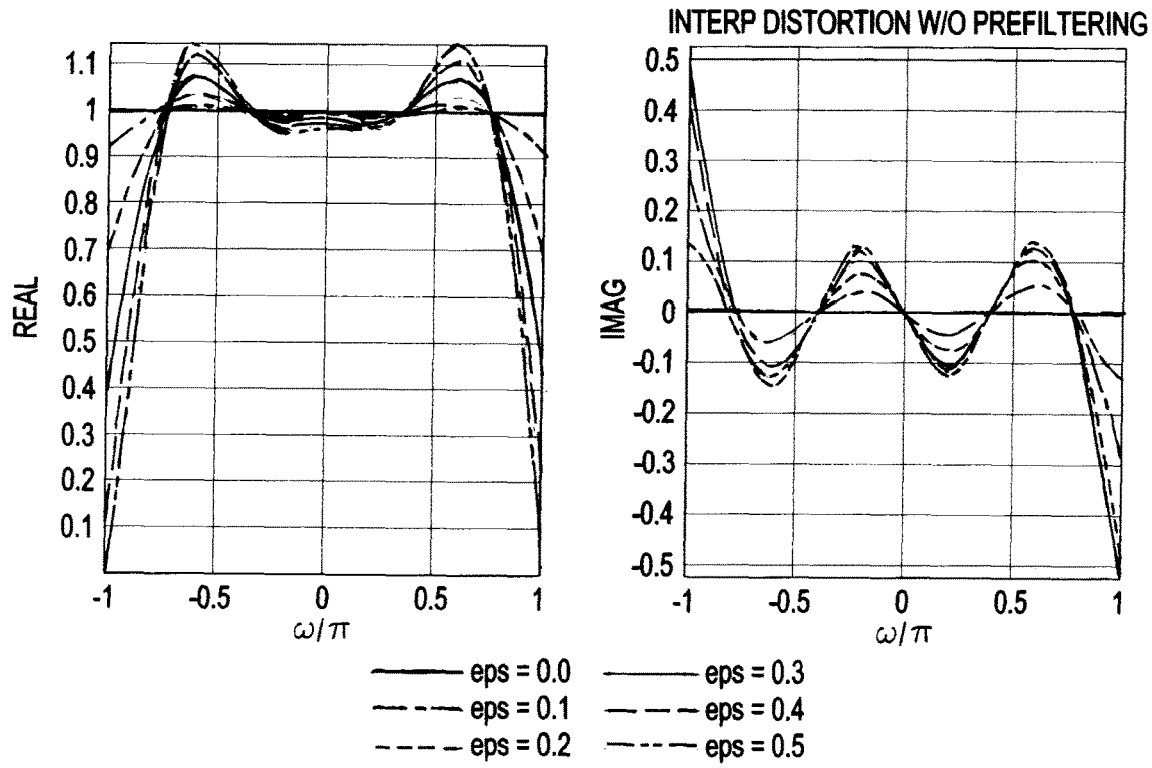
Figure 25:
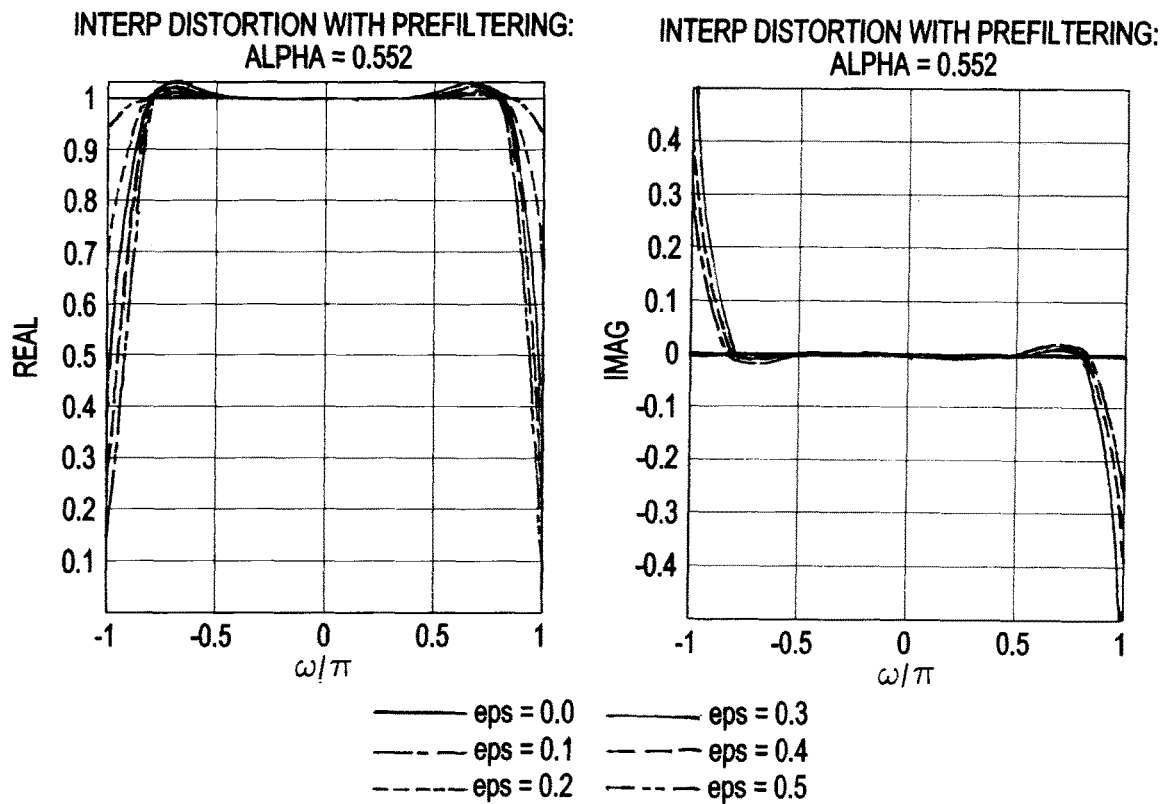

FIG. 24 illustrates frequency-dependent distortion from interpolations at different fractional offsets that result from four-point interpolations using weights that are determined by fitting the frequency response of the interpolation to the time-shift response $e^{-j\omega\epsilon}$ FIG. 25 illustrates frequency-dependent distortion from interpolations at different fractional offsets that result from four-point interpolations using weights that are determined by fitting the frequency response of the interpolation to the time-shift response $W_\alpha(\omega)e^{-j\omega\epsilon}$ and $1/W_\alpha(\omega)$ prefiltering.

Figure 26:
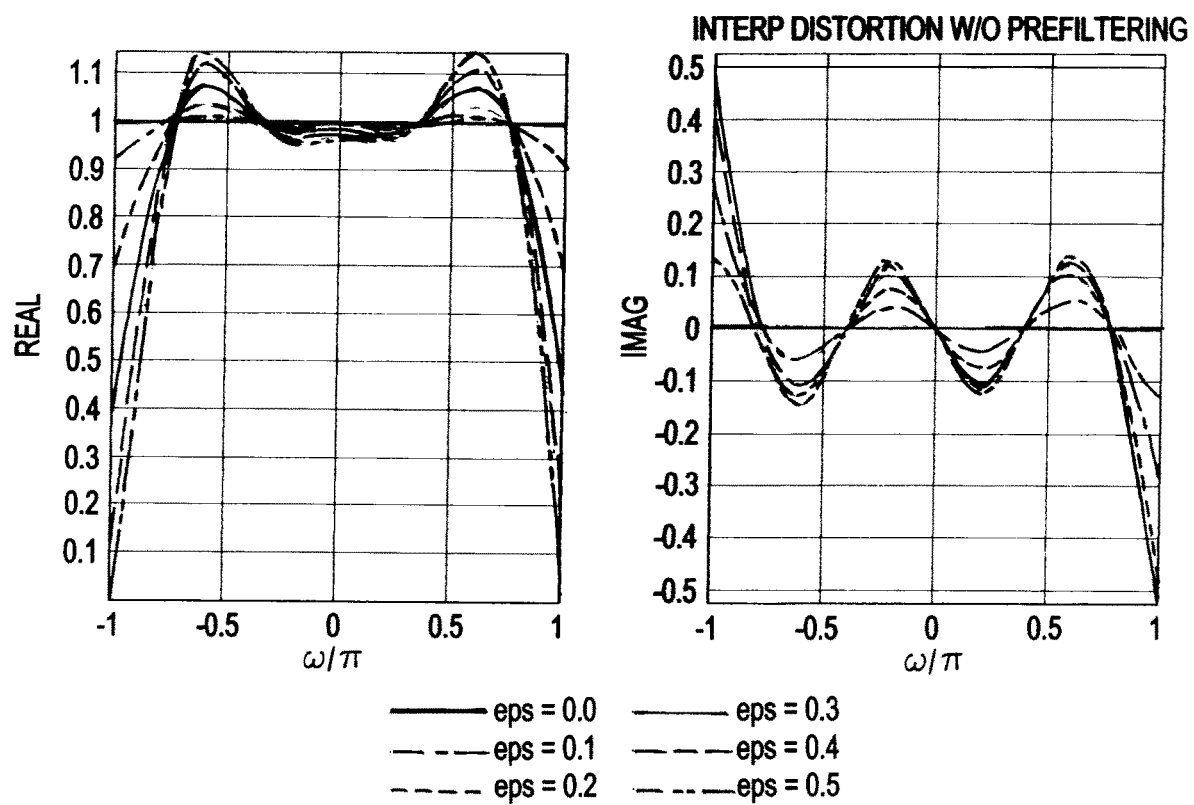

FIG. 26 illustrates frequency dependent distortion from interpolations at different fractional offsets that result from four-point interpolations using weights that are determined by fitting the frequency response of the interpolation to the time-shift response $W_\alpha(\omega)e^{-j\omega\epsilon}$ over the frequency range $[-0.8\pi, +0.8\pi]$ and $1/W_\alpha(\omega)$ prefiltering.

DETAILED DESCRIPTION

It is to be understood that the figures and descriptions have been simplified to illustrate elements that are relevant for clear understanding, while eliminating, for the purpose of clarity, many other elements found in the field of ultrasound imaging systems. Those of ordinary skill in the art may recognize that other elements and/or steps are desirable and/or required in implementing the systems and methods described herein. However, because such elements and steps are well known in the art, and because they do not facilitate a better understanding, a discussion of such elements and steps is not provided herein. The disclosure herein is directed to all such variations and modifications to such elements and methods known to those skilled in the art.

Definitions

Unless defined otherwise, all technical and scientific terms used herein have the same meaning as commonly understood by one of ordinary skill in the art. Any methods and materials similar or equivalent to those described herein can be used in the practice for testing of the systems and methods described herein. In describing and claiming the systems and methods, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of 20%, ±10%, ±5%, ±1%, or +0.1% from the specified value, as such variations are appropriate.

The terms "HABIS," "system," and the like are used interchangeably herein and refer to a system comprising a hemispheric array of ultrasound transducers and a computer network suitable for high-performance parallel processing of data collected from the hemispheric array. As described herein, such a system may include software and associated algorithms to reconstruct volumetric images of a patient's breast. It is also contemplated herein that such a system can be configured to reconstruct volumetric images of other parts of a patient's anatomy, or any other scattering object.

The terms "patient," "subject," "individual," and the like are used interchangeably herein, and refer to any animal amenable to the systems, devices, and methods described herein. Preferably, the patient, subject or individual is a mammal, and more preferably, a human.

Ranges: throughout this disclosure, various aspects can be presented in a range format. It should be understood that the description in range format is merely for convenience and brevity and should not be construed as an inflexible limitation on the scope. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

Described herein is a hemispheric breast imaging system (HABIS) that acquires ultrasound scattering measurements using a hemispheric array of transducers, and reconstructs the volume of a subject's breast using a high-performance computer network. As contemplated herein, there are two hardware components of HABIS, i.e., a data-acquisition apparatus and a high-performance computer network, have been integrated to implement efficiently and accurately an inverse scattering algorithm that reconstructs high-resolution images of a subject's breast volume. In one embodiment, the data-acquisition apparatus includes an array of ultrasound transducers arranged in a generally hemispheric pattern and all electronics required for transmitting and receiving ultrasound signals from the array. In one embodiment, the high-performance computer network includes a plurality of interconnected computer nodes configured for fast, parallel processing of the data received from the data-acquisition apparatus.

Described herein is also an inverse scattering algorithm for reconstructing an image of a breast or other target scattering object. The general purpose of the inverse scattering algorithm is to reconstruct an image of the scattering object from measurements of the effects that the object has on incident signals used to probe the object.

However, reconstructions using existing techniques can be challenging for a number of reasons. For example, the relationship between the object and the scattering measurements is nonlinear, thus, high-quality reconstructions generally require iterative procedures. Since only a finite set of scattering measurements can be acquired, the scattering object can never be completely characterized. The scattering information is particularly limited when physical restrictions are present on the range of incident and receive signal directions. Further, fine details of the object correspond to small variations in the scattering measurements, which can be overwhelmed by other scattering responses and can be easily confused with system noise. Lastly, numerical methods that ameliorate these problems can be prohibitively time-consuming, computationally expensive, or both. HABIS resolves the above issues through the implementation of a unique algorithmic and engineering design as described herein.

As described herein, HABIS provides speckle-free, high-resolution, quantitative images of intrinsic tissue characteristics, e.g., sound speed and attenuation slope, for improved detection, diagnosis, and treatment monitoring of breast cancer. In one embodiment, the system can acquire data during an approximately two-second interval by using 10,240 parallel channels for transmission and reception. The system can image an entire breast volume within minutes, with isotropic point resolution as good as the lateral resolution of x-ray mammography, by using an algorithm that independently and simultaneously reconstructs subvolumes spanning the breast. Using ultrasound, the system can be used to examine a breast with non-ionizing radiation for cancer detection. The system overcomes limitations of x-ray mammography such as low resolution of contrast in dense breast tissue, i.e., breast tissue with high x-ray attenuation; distortion and discomfort resulting from compression-induced deformation of the breast, and poor imaging of breasts having implants. Accordingly, the system can significantly improve the detection and diagnosis of breast cancer, and can also improve the monitoring of response to breast cancer treatment, compared to systems currently available.

The reconstruction algorithm described herein can reconstruct subvolumes independently, i.e., in parallel. Graphic processing units (GPUs) allow small high-performance computers (HPCs) to perform massively parallel computations that are ideally suited for implementation of the described parallelized reconstruction algorithm. Accordingly, in one embodiment, the system can include a GPU-based HPC network coupled to a data-acquisition apparatus that enables reconstructions of the breast volume to be obtained in a relatively short amount of time. For example, in one embodiment, the breast volume can be reconstructed in less than 20 minutes, and in other embodiments, in less than 15 minutes, in less than 10 minutes, or in less than 5 minutes. However, it is contemplated herein that a person skilled in the art could readily modify the system to even further decrease the reconstruction time, for example by using faster processing units or by increasing the number of nodes. In contrast to this, on a supercomputer using an existing method for reconstruction of a large single volume, such reconstructions can require time periods of as much as a few days. This improvement in reconstruction time provided by HABIS can have an enormous impact on the clinical utility of imaging systems because data can be acquired, and the reconstructed volumes of the breast viewed, in the course of a single visit. Accordingly, because HABIS is capable of producing images with at least 100 micron resolution in minutes, HABIS provides an improved and efficient way to screen for breast cancer and also to diagnose other breast diseases. In a manner previously unattainable.

Imaging System

In one embodiment, HABIS comprises an apparatus for acquiring data from an array of ultrasound transducers. In another embodiment, HABIS includes an examination table that houses or otherwise integrates at least part or all of the data acquisition apparatus, which may include both its front-end and back-end electronics. In yet another embodiment, the data acquisition apparatus can be connected to a network of computers that can process or otherwise perform the desired image reconstruction. For example, in one embodiment, the front-end electronics are arranged radially under the patient "head" end of the table around the generally hemispheric transducer array. In one embodiment, under the foot-end of the table are electronic modules that can include power supplies, power-supply filter boards, control boards, isolation transformers, high-voltage regulator boards, circuit breakers, and cable channels, as needed. In one embodiment, the system can also include other components suitable for use with a particular application associated with the image acquisition, such as a fluid-handling cart and an operator console which can be positioned near the examination table.

Figure 1:
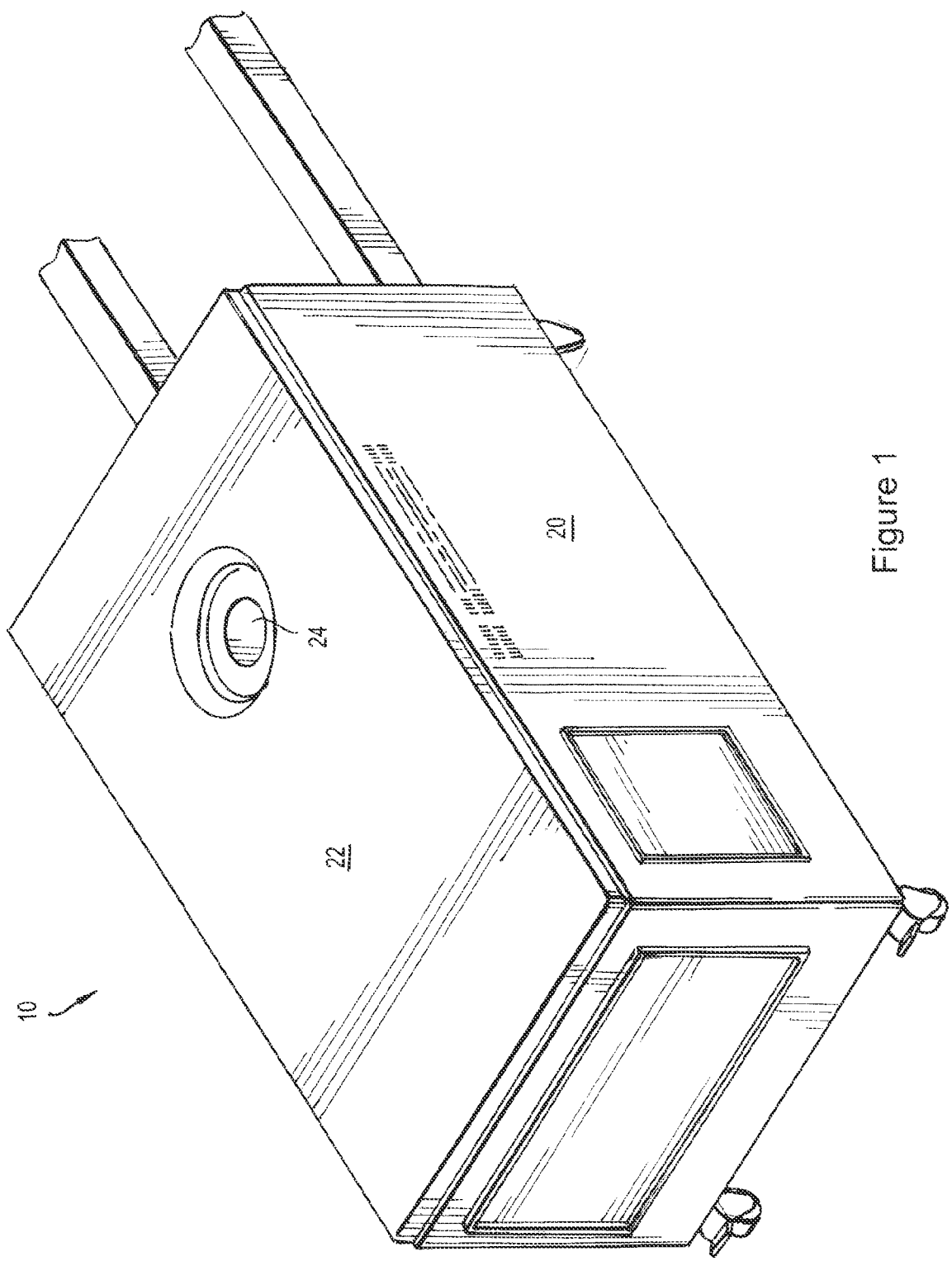
FIG. 1 is a schematic of an exemplary embodiment of a hemispheric breast imaging system (HABIS) integrated with a patient examination table.
Figure 2:
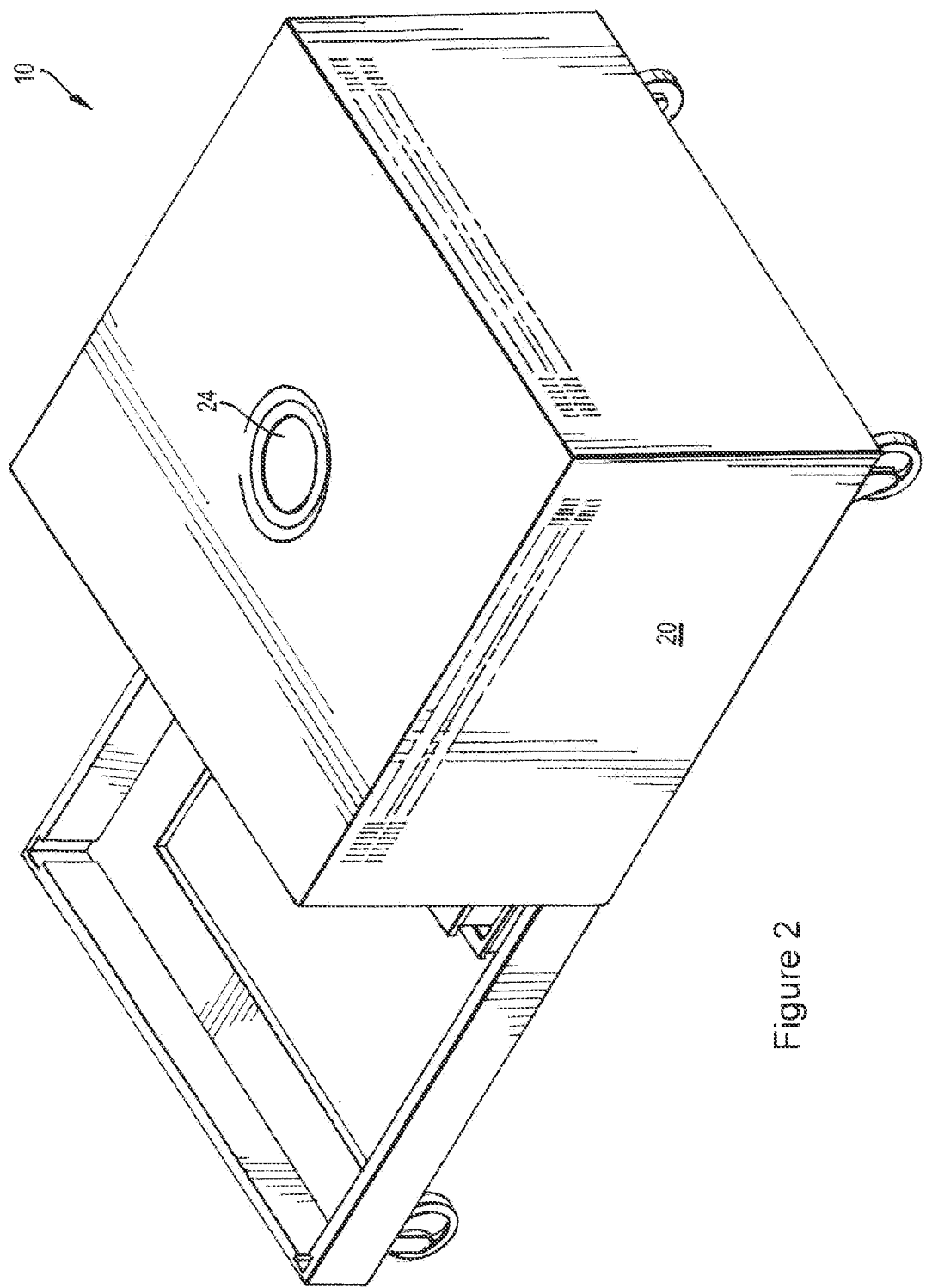
FIG. 2 is a schematic of another exemplary embodiment of a HABIS integrated with a patient examination table, wherein the examination table surface and a portion of the sides of the table have been removed.

Referring now to FIG. 1, an exemplary embodiment of the data acquisition apparatus 10 of the system is shown, wherein the apparatus is at least partially integrated into the surface of an examination table 20 generally having a surface 22 for a subject to lie on. Surface 22 has an opening or cup 24 into which a scattering object, such as a patient's breast, can be placed. The hemispheric transducer array of the system may form the exposed walls of cup 24, or alternatively, cup 24 may be a permanent or disposable container that fits within the cavity of the transducer array hemisphere to prevent direct contact of the scattering object with the transducers, and/or to hold a suitable amount of coupling fluid, gel or other material used during the imaging procedure. For example, the container may be a detachable and disposable cup-shaped container. Accordingly, a patient can lie prone on table surface 22 with either the right breast or the left breast pendant in cup 24. Further, cup 24 can be filled with a coupling fluid or any other suitable material as desired during an ultrasound imaging procedure. FIG. 2 is a schematic of another embodiment of data acquisition apparatus 10, wherein the examination table surface and a portion of the sides of table 20 have been removed. Again, the head end of table 20 houses the hemispheric array assembly, which is designed to image an object placed in cup 24.

Figure 3:
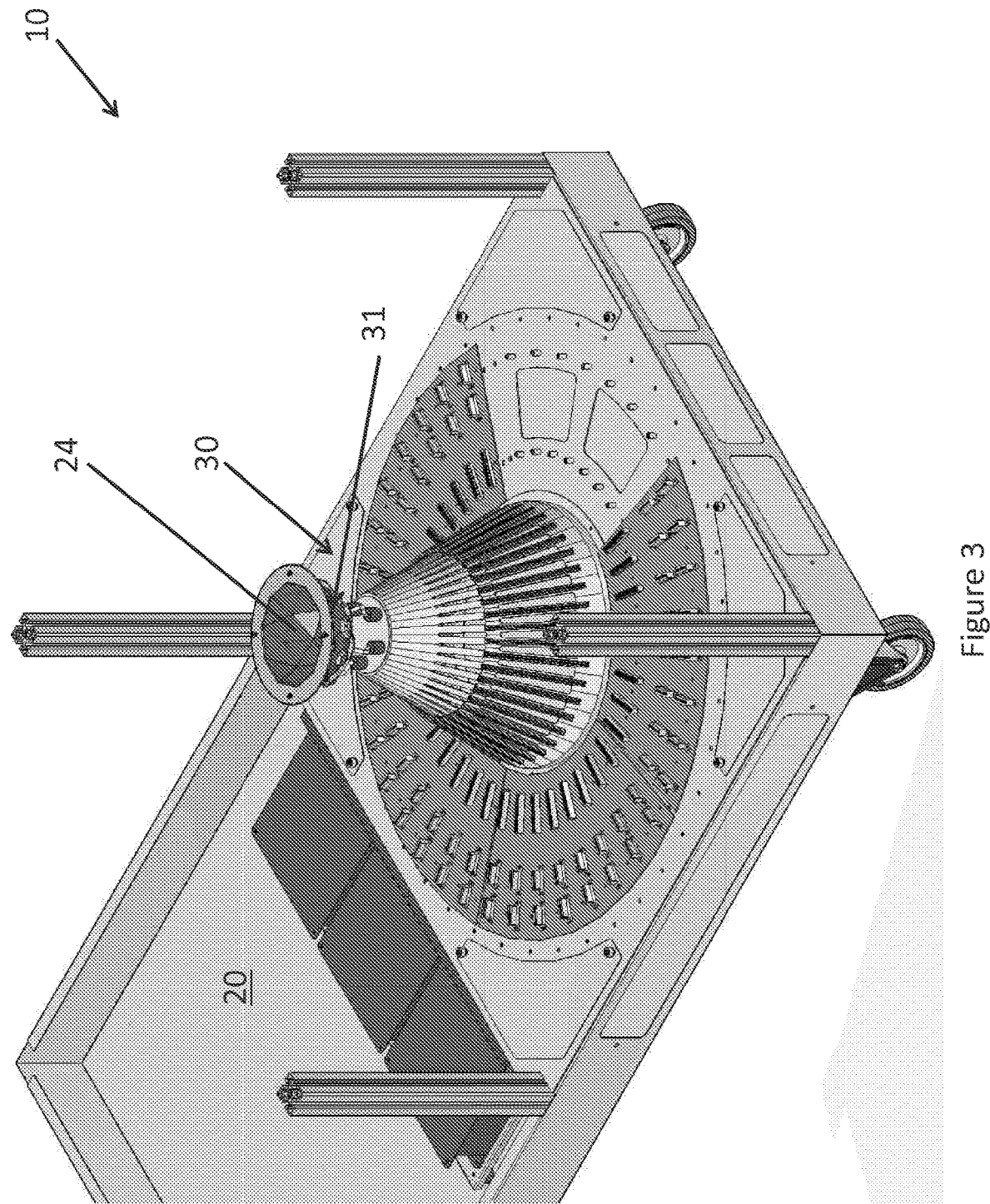
FIG. 3 is a schematic of the front-end electronics of an exemplary embodiment of a HABIS, showing a hemispheric cup and ultrasound transducer assemblies.

FIG. 3 is another schematic of data acquisition apparatus 10, wherein all sides of table 20 have been removed to show a portion of a hemispherical array assembly 30. Hemispherical array assembly 30 includes a plurality of transducers, or transducer element assemblies 31 having an inner surface for transmitting and receiving ultrasound signals via a plurality of piezoelectric elements, and an outer surface configured with suitable circuitry for transferring electrical current and signal data to/from the piezoelectric elements within the transducer facets. Accordingly, the inner surface of cup 24 forms a cavity for holding a scattering object, for example a patient's breast, that can be imaged using ultrasound. Further, cup 24, or otherwise the cavity formed by the inner surfaces of the transducers, also defines the imaging region within the apparatus or device. As contemplated herein, the cup can comprise any material suitable for ultrasound analysis, as would be understood by a person skilled in the art. In the embodiments described herein, the cup is substantially hemispherical in shape. However, the cup may be a shape other than a hemisphere, provided that the array of ultrasound transducers and other electronic components of the system, and also the image reconstruction algorithm described later herein, are suitably modified to suitably image the resultant object volume within the imaging region.

In one embodiment, data acquisition apparatus 10 of the system can acquire a complete scan of over 100 million receive waveforms in about a two-second time period, with minimal noise contributions to the receive waveforms, and with very precise control over both the timing of the transmissions and the sampling of the received waveforms. In various embodiments, hemispheric array assembly 30 comprises a plurality of data-acquisition subassemblies connected to the transducer elements. In one embodiment, hemispheric array assembly 30 comprises forty (40) data-acquisition subassemblies that are each connected to a single transducer element assembly. However, the number of data-acquisition subassemblies is not limited to forty, and can be more or less than forty, depending on the number of transducer assemblies and/or other factors, such as the desired resolution and/or speed of the reconstructed image.

Figure 4A:
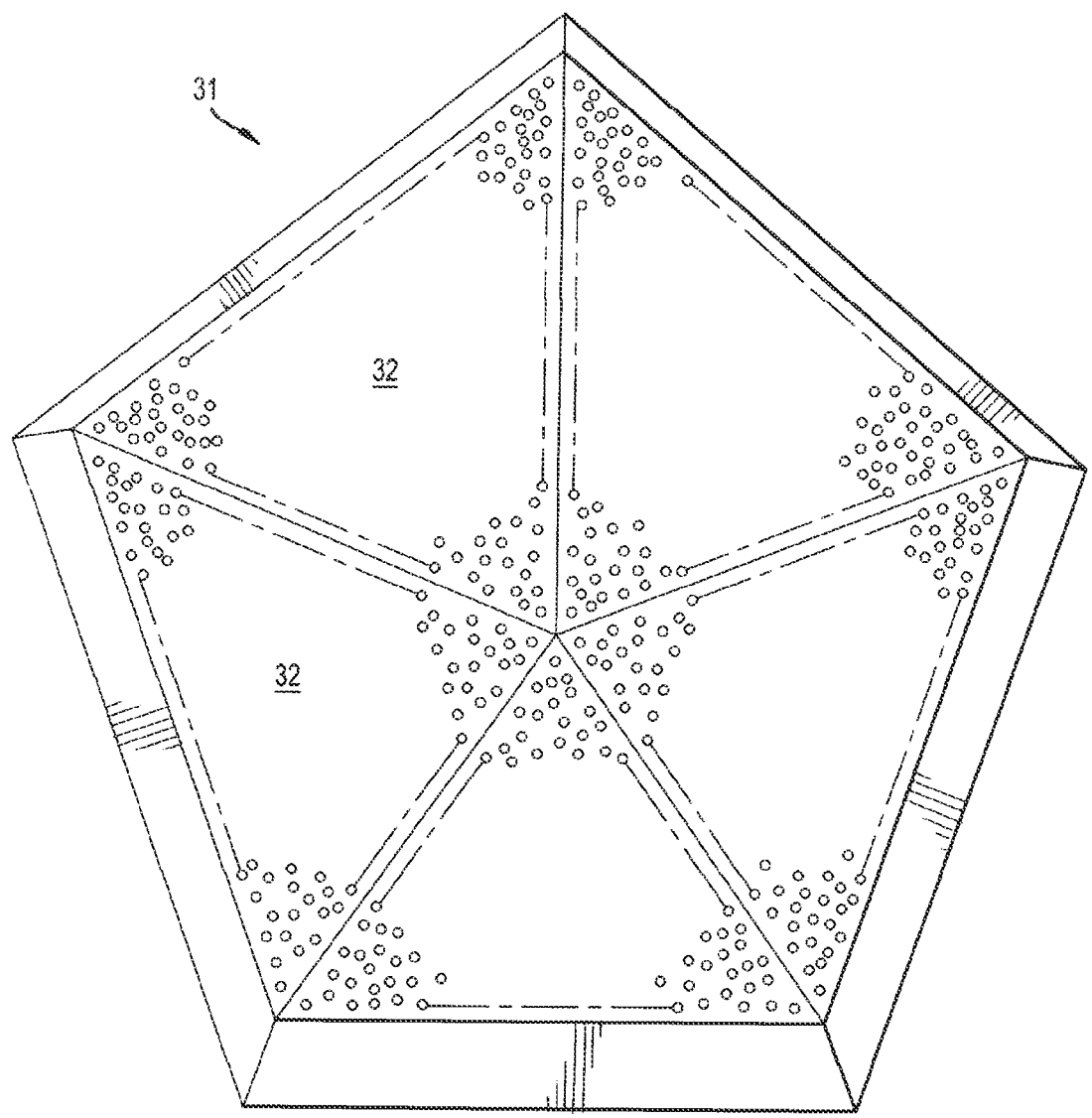
FIGS. 4A through 4C, is a set of images of an exemplary embodiment of a transducer element subassembly, which can form a part of a hemispheric ultrasound transducer array.
Figure 4B:
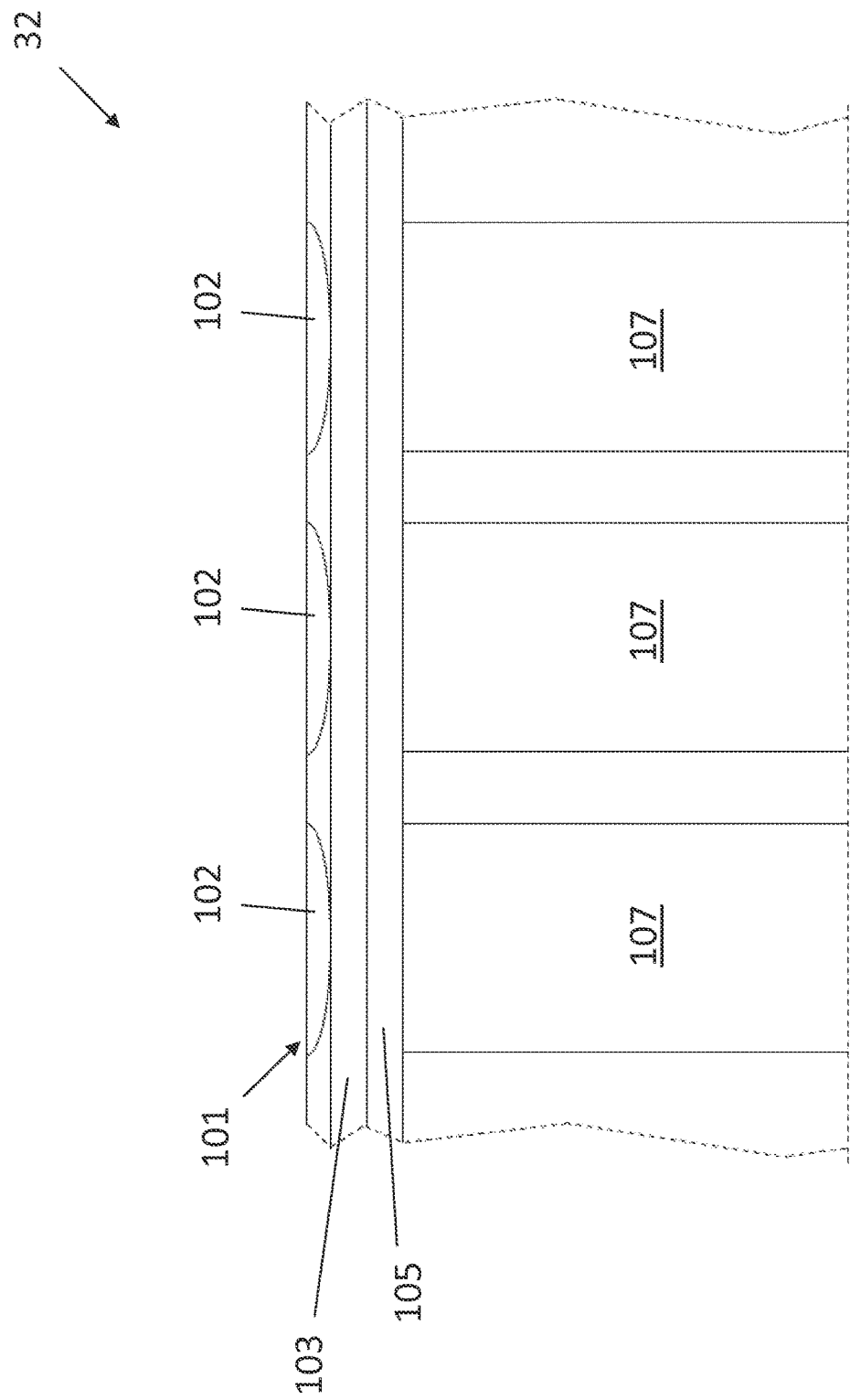
Figure 4C:
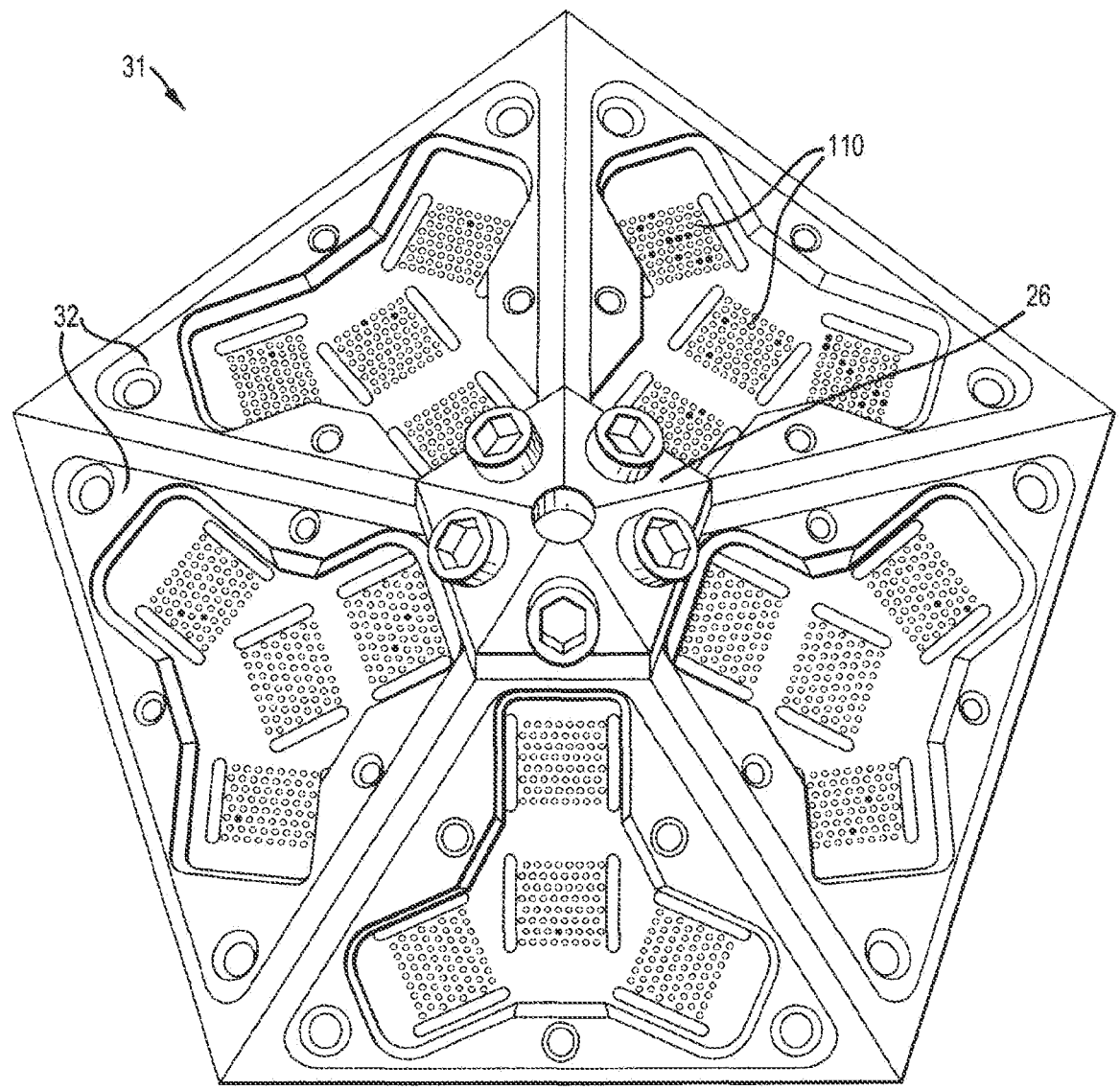

Referring now to FIG. 4, an exemplary embodiment of a transducer element subassembly 31 is shown. FIG. 4A is a view of the inner surface of transducer element subassembly 31 comprising five triangular planar facets 32. Each planar facet 32 comprises a plurality of piezoelectric elements that are located underneath the dimples or depressions on the surface of facets 32. In FIG. 4B, a cross-sectional X-ray of an exemplary planar facet 32 is shown. Facet 32 includes a surface layer 101 that comprises a plurality of depressions or dimples 102. In one embodiment, a diverging lens is located in each dimple 102. In one embodiment, surface layer 101 can be coated with a polymer, for example a Parylene polymer. Beneath surface layer 101 are two matching layers 105. In one embodiment, facet 32 can comprise a number of matching layers other than 2, for example 1 or 3 matching layers. Matching layers 103 and 105 can comprise any material, and can be any thickness, that would be suitable for an ultrasound transducer matching layer, as would be understood by a person skilled in the art. Beneath matching layers 103 and 105 is a plurality of ultrasound transducer elements 107. Each transducer element 107 is substantially aligned with a dimple 102. Transducer elements 107 can comprise any material suitable for an ultrasound transducer known in the art, for example PZT crystal. Further, facet 32 comprises a backing layer (not shown) beneath transducer elements 107. The backing layer can comprise any suitable backing material for an ultrasound transducer. In one embodiment, the backing layer comprises a conductive epoxy. In one embodiment, facet 32 can comprise additional layers, for example a conductive metal coating on either side of the transducer elements, for grounding and excitation. In one embodiment, facet 32 can comprise additional components, for example printed circuit boards. FIG. 4C is a view of the outer surface of transducer subassembly 31. Five triangular planar facets 32 are connected together via a bracket 26. A plurality of wire connectors 110 are located on the outer surface of each facet 32. Wire connectors 110 can be used to communicatively couple transducer elements 107 to the data-acquisition components described later herein, for example via printed circuit boards.

Figure 5:
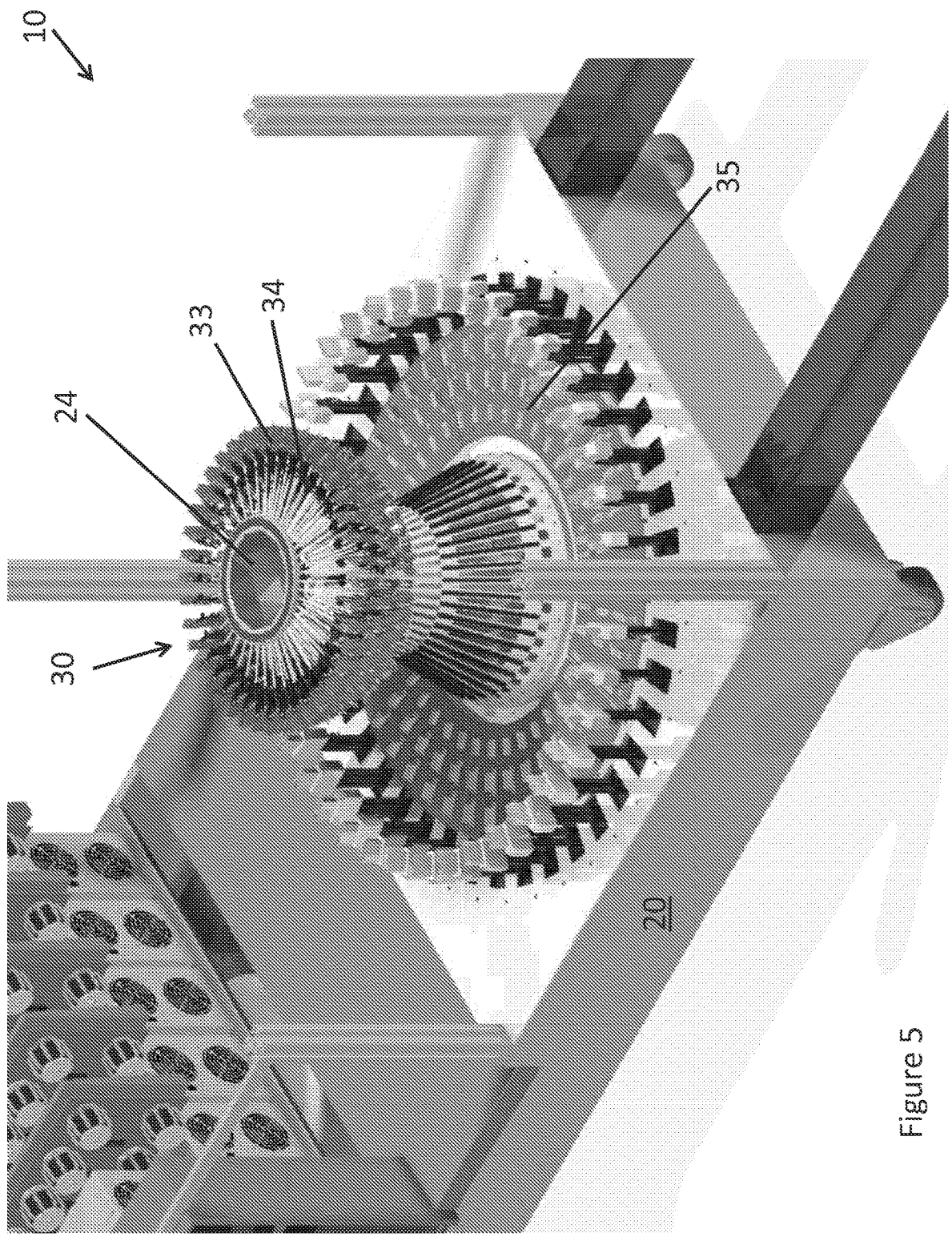
FIG. 5 is a schematic of the front-end electronics of an exemplary embodiment of a HABIS, showing a portion of the data-acquisition subassemblies.

Referring now to FIG. 5, transducer assemblies 31 of hemispheric array assembly 30 are shown coupled to forty front-end boards, i.e., data-acquisition subassemblies 33 (only a portion of these boards are shown in FIG. 5). In this embodiment, data-acquisition subassemblies 33 radiate from the axis of assembly 30. In one embodiment, each data acquisition subassembly 33 comprises 256 channels of electronics, and is connected to the transducer assemblies 31 via cable connections 34, which may be relatively short in length to minimize signal loss. In one embodiment, cable connections 34 are PCIe cables. Hemispheric array assembly 30 also includes bottom-plane boards 35 for distributing power and timing, as would be understood by those skilled in the art. In one embodiment, data collected by at least one of the 256-channel data acquisition subassemblies 33 can be sent to imaging computers through suitable cables, e.g., PCIe cables. In one embodiment, the cables may be about five meters long, but it should be appreciated that these cables can be any length desired, as would be understood by a person skilled in the art. This arrangement allows each ultrasound transducer element assembly 31 to be in close proximity with the front-end circuitry that is used to collect signals from the element. The close proximity between the transducer elements and the data acquisition circuitry lowers signal loss and extends the range and angle over which useful signals can be transmitted and received.

Figure 6:
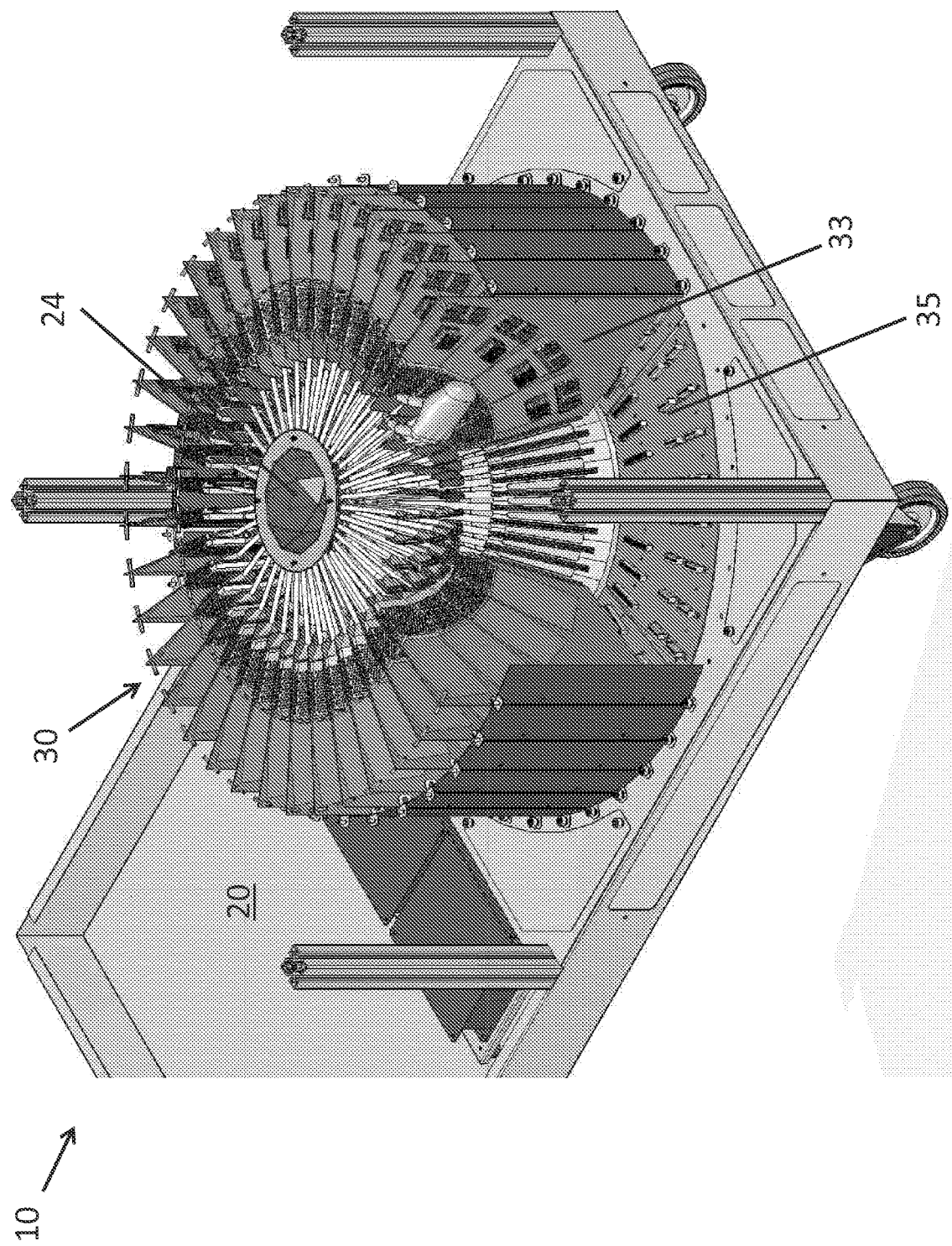
FIG. 6 is a schematic of the front-end electronics of an exemplary embodiment of a HABIS, showing a plurality of data-acquisition subassemblies connected to the ultrasound transducer assemblies.

Referring now to FIG. 6, the forty sets of data-acquisition electronics subassemblies 33 are shown mounted in groups of eight on five bottom plane boards 35 that together form an annulus encircling the axis of the hemisphere array in a plane below the hemisphere. Bottom-plane boards 35 are used to distribute timing and control information as well as to provide power to the forty data-acquisition subassemblies 33. This data-acquisition subassembly and bottom-plane arrangement enables high-precision timing signals to be distributed without appreciable degradation. In the embodiment shown, each data-acquisition subassembly 33 includes four blocks of 64-channel electronics positioned in successive angular sections of the board. This arrangement allows transducer assemblies 31, comprising a total of 10,240 transducer elements, to be in proximity to the hemispheric array electronics. In such an embodiment, transducer assemblies 31 are connected to the electronics through 160 short cables.

Figure 7:
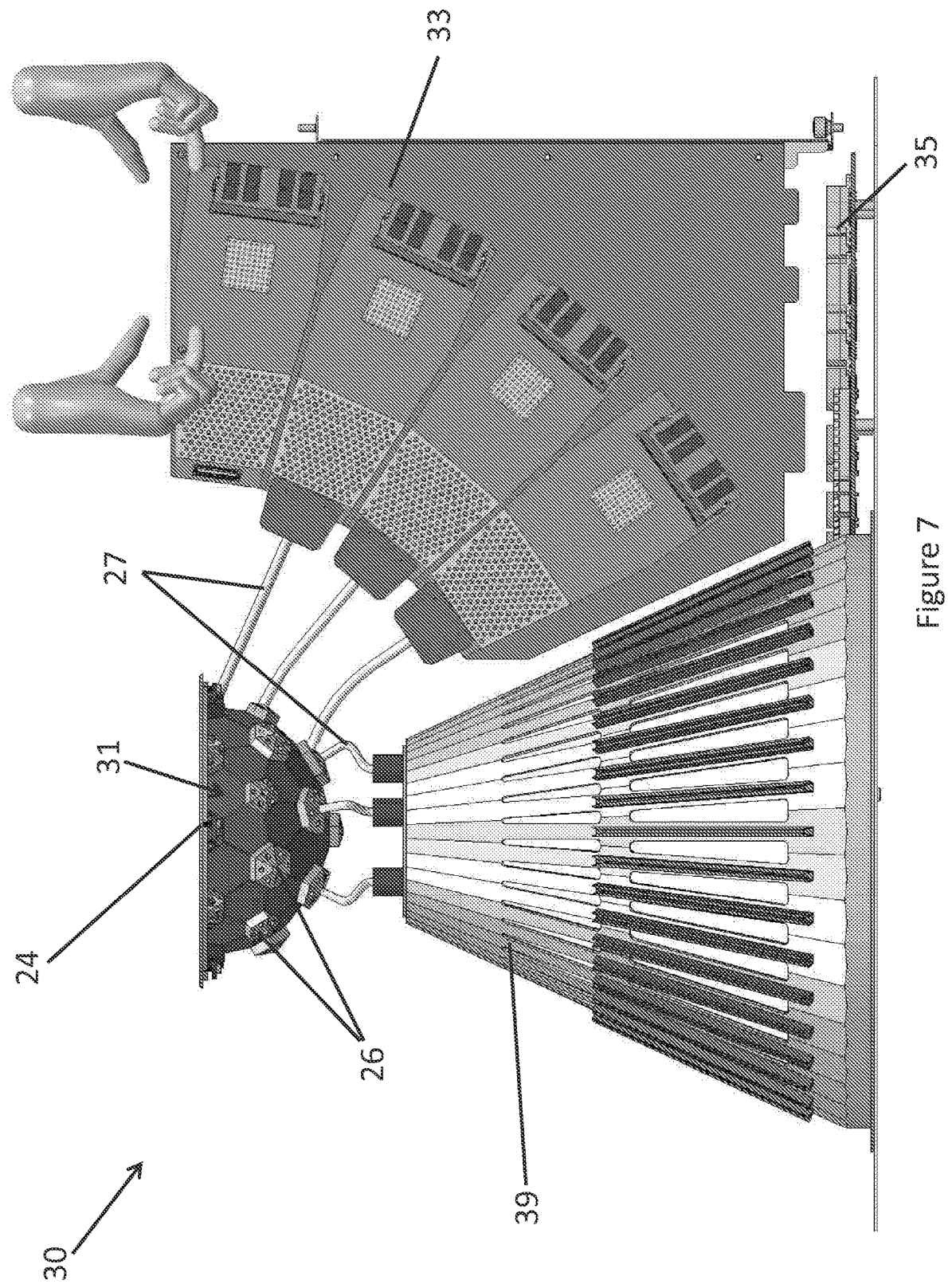
FIG. 7 is a schematic of the front-end electronics of an exemplary embodiment of a HABIS, showing how an exemplary data-acquisition subassembly is connected to an ultrasound transducer assembly.

FIG. 7 shows how the 256-channel data-acquisition subassemblies 33 plug into hemispheric array assembly 30 and shows the conical frame 39 that supports the inboard edge of the 256-channel subassemblies 33. Conical frame 39 also forms a plenum to direct air flow, for example air flow from fans that can be placed in another portion of the examination table. In one embodiment, each transducer element subassembly 31 includes a bracket 26. In one embodiment, brackets 26 can be connected to data-acquisition subassemblies 33 via a plurality of flexible supports 27. Further, transducer element assemblies 31 are connected to data-acquisition subassemblies 33 via wiring suitable for sending and receiving signals (not shown).

In one embodiment, during each two-second scan, every data acquisition subassembly 33 receives 10,240 waveforms with 4,096 temporal samples in each waveform from 256 different transducer elements located in transducer assemblies 31. Thus, a total of 32.2 GB is acquired by each subassembly. By comparison, if a typical computational system would be used for reconstruction, then the data from all forty data acquisition subassemblies 33, i.e., a total of 40×32.2 GB, or 1.28 TB, would need to be aggregated and transferred to that system. However, a significant part of the processing can be performed on data from each acquisition subassembly 33 without reference to data from the other acquisition subassemblies. As a result, the amount of data that needs to be transferred to a computer system to complete the reconstruction, after the initial phase of independent parallel processing has been completed, is about 1,000 times smaller than without the use of such parallel processing. Currently available GPU architectures have the processing capability to complete the computations required for HABIS. Accordingly, data acquisition apparatus 10 includes GPU cards that are distributed in the nodes of the data acquisition network. Further, superimposing a web of InfiniBand connections on the network enables rapid inter-node communication necessary in later stages of the computation so that the remainder of the reconstruction computations can be completed with similar speed. As a cost-saving and space-saving measure, in one embodiment, the HABIS data-acquisition subassemblies each incorporate 256 channels of circuitry. Such an arrangement can be used to prevent noise from the digital electronics from interfering with analog reception.

Figure 8:
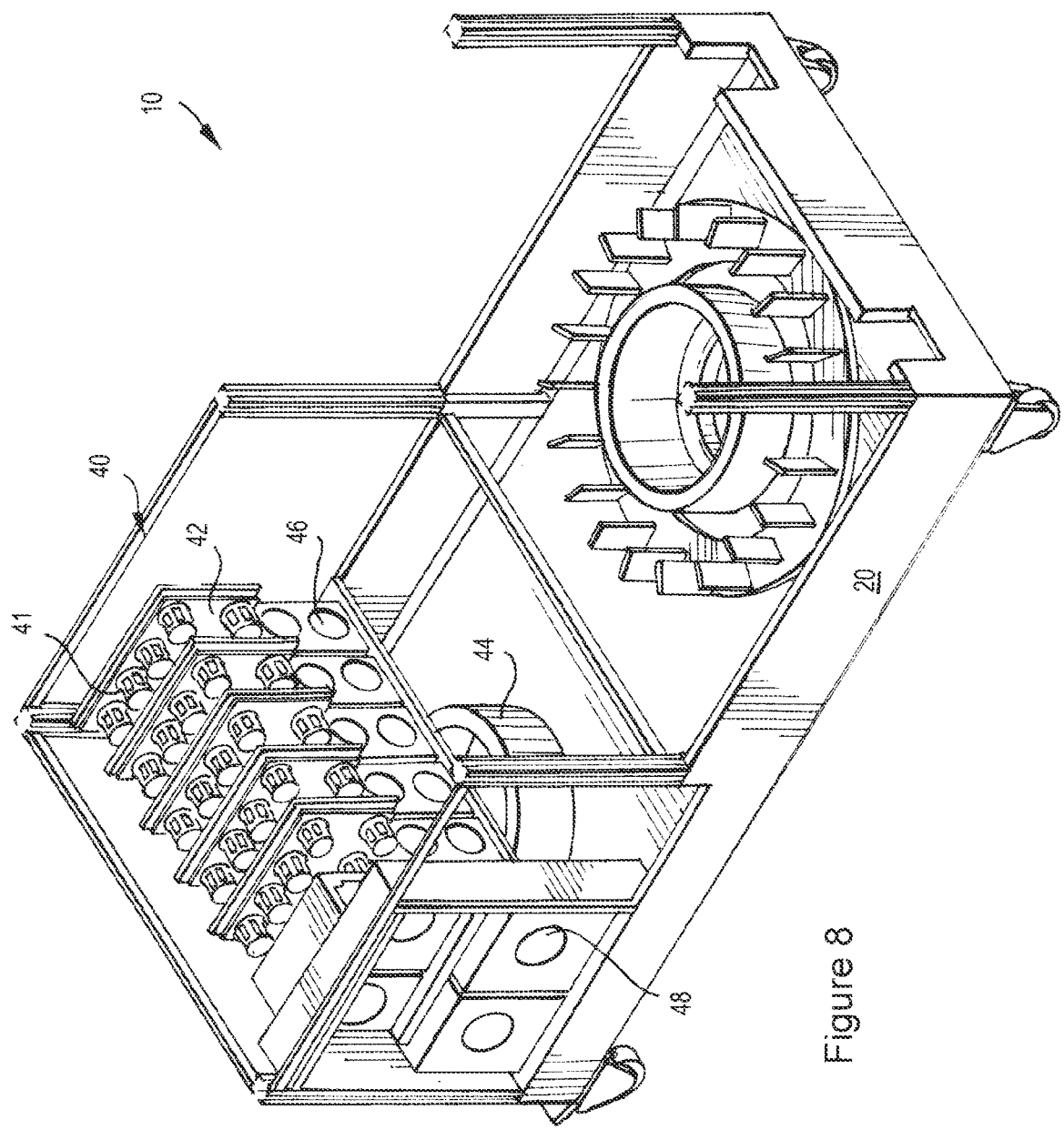
FIG. 8 is a schematic of the AC wiring and power supply distribution of an exemplary embodiment of a HABIS.

FIG. 8 is a diagram showing the power supply assembly 40 positioned within the interior of table 20. Power supply assembly 40 can include components necessary for the operation of hemispheric array assembly 30, including, but not limited to: a plurality of power supplies 41, power-supply filter boards 42, isolation transformers 44, cooling fans 46, air ducts 48, high-voltage regulator boards, a power-control module, wiring connection blocks, disconnect switches, and circuit breakers within examination table 20. Alternatively, in one embodiment, such components can be placed in a location outside of examination table 20, for example in a secondary cabinet.

Figure 9:
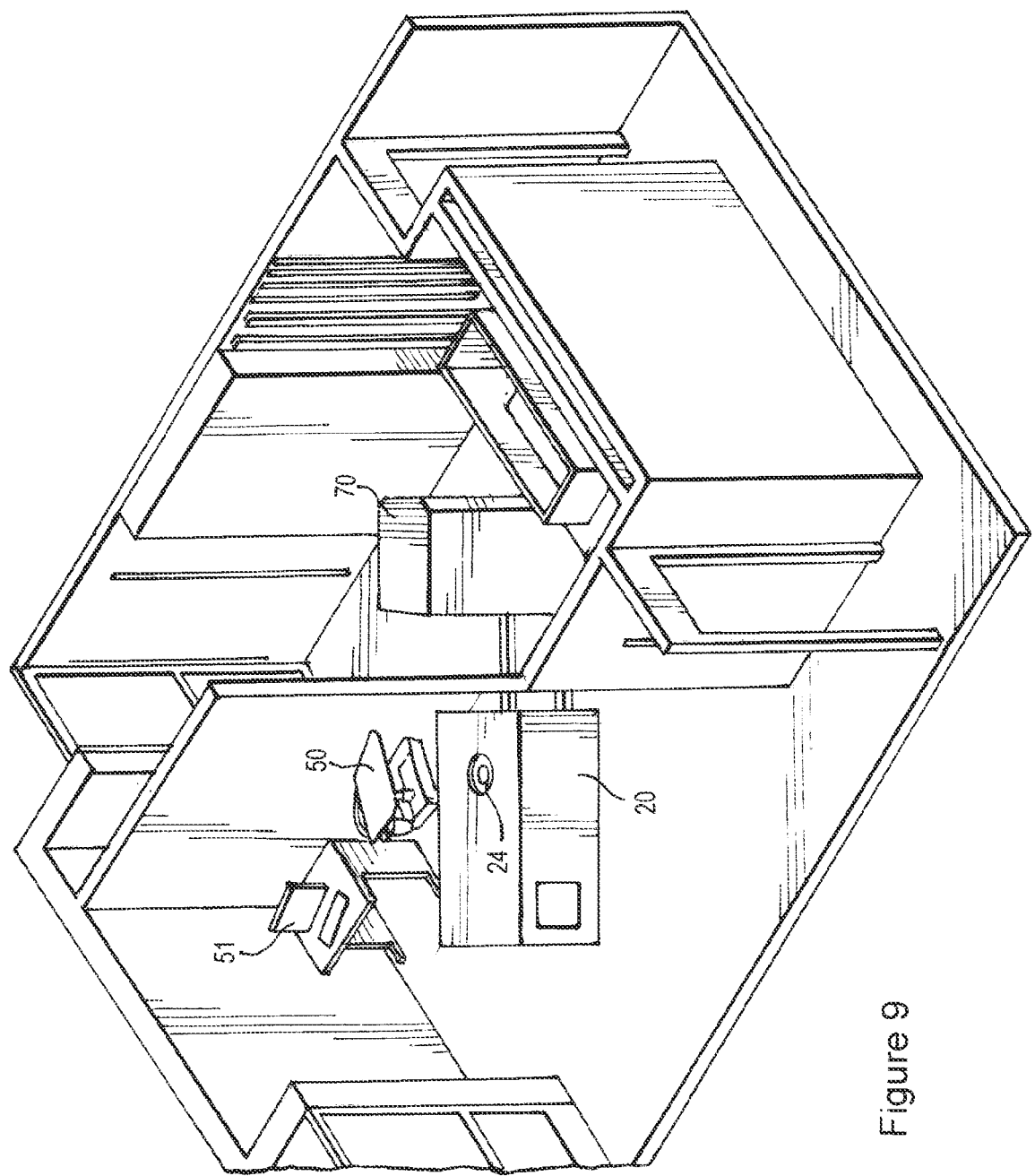
FIG. 9 is a schematic of the HABIS patient examination table of FIG. 1 positioned in an exemplary examination room.

FIG. 9 is a diagram showing examination table 20 in an examination room. Examination table 20 can be connected to an operator console 51, which can be used to control any portion of the system, as needed. In addition, a fluids cart 50 can be connected to table 20 to provide a supply and/or recirculation of coupling, i.e., ambient fluid to cup 24. Further, table 20 can be connected to a computer network/scalable server set 70 for image reconstruction, as will be described later herein.

In various embodiments, the components of HABIS can be connected to one or more power supplies suitable to provide power for their operation. For example, in one embodiment, examination table 20 can be connected to a three-phase 208-volt AC supply through a disconnect switch and an isolation transformer. Computer network 70 can be connected to another three-phase 208-volt AC supply through another disconnect switch. In one embodiment, no isolation transformer is included in computer network 70 because the only connection between examination table 20 and computer network 70 is a set of 40 low-voltage PCIe cables. However, the various components of HABIS can be supplied power in any manner as would be understood by a person skilled in the art, and the power supply arrangement is not limited to the specific embodiments described herein.

As previously described, in one embodiment, HABIS is an integrated data-acquisition apparatus and high-performance network that rapidly collects imaging data and efficiently implements fast parallel computation of images via an inverse scattering algorithm. In such an embodiment, the architecture of the system permits GPU-based parallel computations on each node and InfiniBand-based aggregation of results at each node. The design of the system avoids extensive time-consuming data aggregation, permits parallel computation of refined data sets that substantially reduce the amount of data transferred between computer nodes for subsequent parallel reconstruction of subvolumes, and enables fast transfer of intermediate computational results between computing nodes. The parallel computation takes place on two levels: a high level on each computing node and a low level on each GPU. A head node in the network can provide command, control, and monitoring. In one embodiment, an Internet connection can enable command, control, and monitoring to be performed remotely. Data-acquisition apparatus 10, as shown and described herein, provides a large number of independent channels, which can accommodate a large volume of data in a short time period, thereby exceeding the performance of currently available systems. For example and without limitation, the system architecture may include separate connections between pairs of data-acquisition electronics sets and nodes of the high-performance computer network. These connections allow processing to take place prior to aggregation of the receive signals. The system architecture may also include configuration of individual compute nodes with cost-efficient resources that efficiently perform the parallel computations used in HABIS reconstructions. The system architecture may also include InfiniBand connections and switching that efficiently perform in a cost-effective manner the burst transfers of data after each stage of computation. The system architecture may also include a mechanical configuration of the data-acquisition apparatus to minimize the lengths of the data paths between the transducer elements and the transmit and receive electronics so that the range and angle over which useful signals can be transmitted and received is greatly extended. The system architecture may also include circuitry designs to reduce cost by consolidation of data-acquisition and data processing electronics. Further, the system architecture may also include a timing and control system that meets the stringent tolerances imposed by coherent imaging and transmission encoding.

Transducer Elements and the Hemispheric Array

Figure 10:
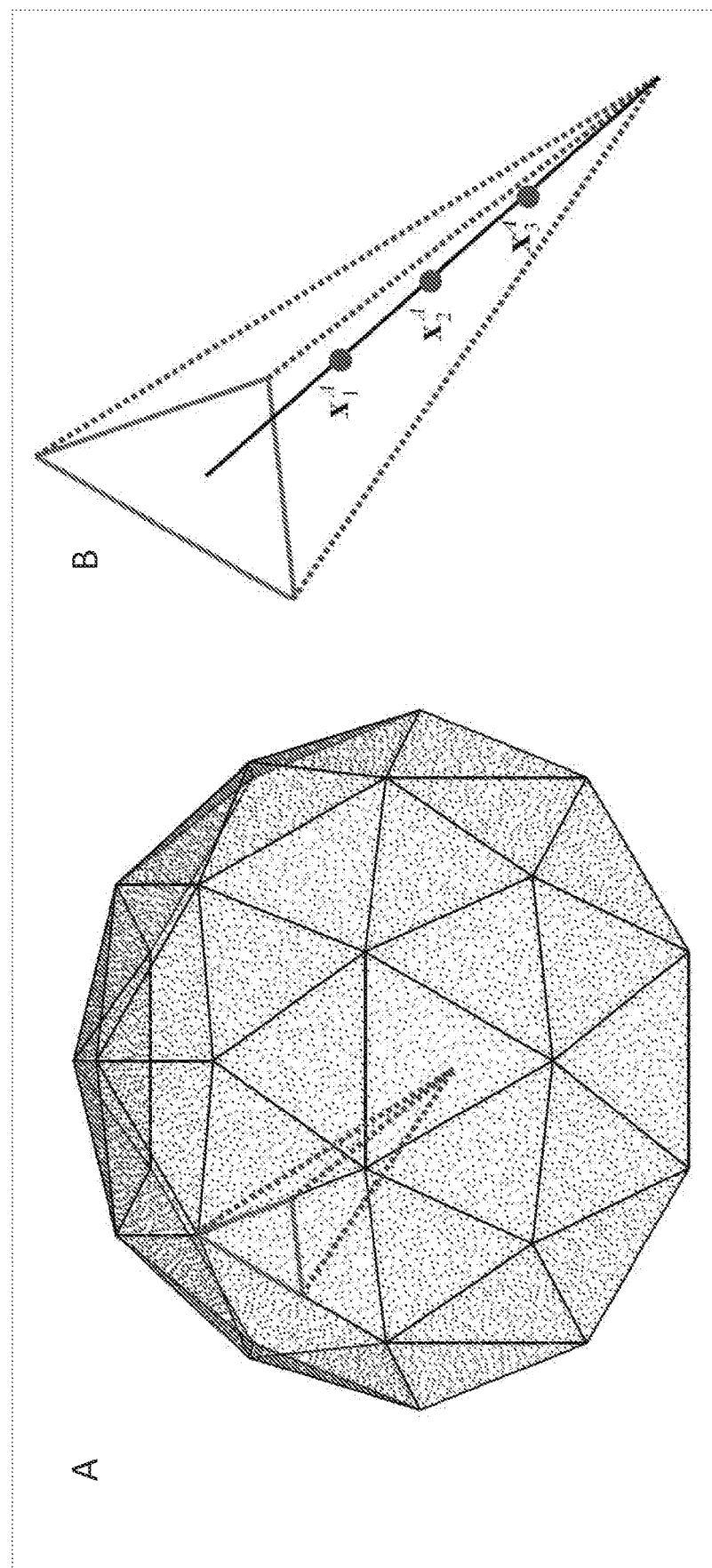
FIG. 10 is a schematic of a hemispheric volume (FIG. 10A) and the tetrahedral region that is associated with a subtriangle of the hemispheric array (FIG. 10B). The portion of the hemispheric volume imaged by the data from the triangular block of receive elements in the triangle is the tetrahedron formed by the vertices of the solid-line triangle and the center of the hemisphere.

In one embodiment, the array of transducer elements of HABIS is arranged in a faceted construction to provide imaging of a generally hemispheric volume. As shown in FIG. 10, in one embodiment, the hemispheric array in HABIS is approximated using 40 triangular planar facets. In one such embodiment, ten of the facets are equilateral triangles and 30 of the facets are isosceles triangles. The use of a faceted approximation of a hemisphere with two types of triangular planar elements greatly simplifies the construction of the array. Further, in such an embodiment, each facet contains 256 small diameter piezoelectric elements, as indicated by the dots on the facets in FIG. 10A, made from a ceramic material composite that suppresses undesirable lateral modes of vibration.

In one embodiment, the elements on the facets are positioned pseudorandomly. The pseudorandom positions permit the use of many fewer elements (and, thus, fewer independent transmit and receive channels) than would be otherwise required to avoid grating lobes during the formation of transmit and receive beams. In one embodiment, one configuration of pseudorandom positions is used on the equilateral facets and another configuration of positions is used on the isosceles facets. The use of two configuration sets of pseudorandom positions significantly facilitates practical fabrication of the array without degrading the capability of the array to form beams.

Each element may include a diverging lens that broadens the pattern of the transmit beam and the pattern of the receive sensitivity. This broadening extends the volume, i.e., the solid angle, of the scattering object illuminated by transmissions from the elements. The broadening also extends the volume i.e., the solid angle, of the scattering object from which ultrasound signals can be received by the elements. The result of the extended coverage is an appreciably enhanced capability to concentrate focuses formed using the array.

Each element in the array may include two matching layers. The matching layers produce a wider temporal-frequency bandwidth than would be obtained without the layers. The matching layers also increase the transmission energy over the energy that would be transmitted without the layers. Additionally, the layers increase the sensitivity of reception over the reception sensitivity that would be obtained without the layers. Further, the transmit waveform applied to the transducer elements is designed to concentrate the transmitted energy within the temporal-frequency bandwidth of elements.

In addition, the receive circuitry contains a tuning element, i.e., an inductor, that cancels the bandwidth-narrowing effect of the capacitance associated with the transducer elements, the cable between the transducer element and the front-end electronics, the parasitic capacitance of the printed circuit wiring, and the input capacitance of the low-noise amplifier in the receiver chain.

The use of transmissions that are coded without degrading crosstalk and the ability to decode receptions without degrading crosstalk is enabled by the front-end electronics assembly design of HABIS. In the system, the connection between the transducer elements and the cable to the electronics is made through a special signal redistribution arrangement implemented on a printed circuit board with wide trace separation and shielding. Additionally, a special pattern of shielded connections between the cable from the transducer and printed circuit board containing the front-end electronics reduces crosstalk significantly compared to the crosstalk that would otherwise exit. The tuning elements noted above are shielded and widely separated to suppress magnetic coupling between channels.

High-Performance Computer Network

As previously described, in one embodiment, HABIS includes a high-performance computer network that is connected to the data-acquisition assembly. A specialized architecture consisting of a data-acquisition apparatus and a high-performance computer network is required to collect the ultrasound data in a short time and to reconstruct the breast volume in minutes thereafter. This is because a computational capability must be integrated into HABIS to enable immediate parallel preprocessing of the acquired data. The initial computations performed in the data-acquisition subassemblies yield refined data sets that substantially reduce the amount of data transferred between computer nodes for subsequent parallel reconstruction of subvolumes. As mentioned elsewhere herein, the system architecture may include 40 sets of data-acquisition subassemblies, with each set containing 256 independent transmit and receive channels, and 20 high-performance computing nodes with each node containing four GPUs. In other embodiments, comparable architectures with different numbers of data-acquisition subassemblies and high-performance computing nodes can be used, as the system is not limited to the specific numbers and arrangements of data-acquisition subassemblies and computer nodes described herein.

Figure 11B:
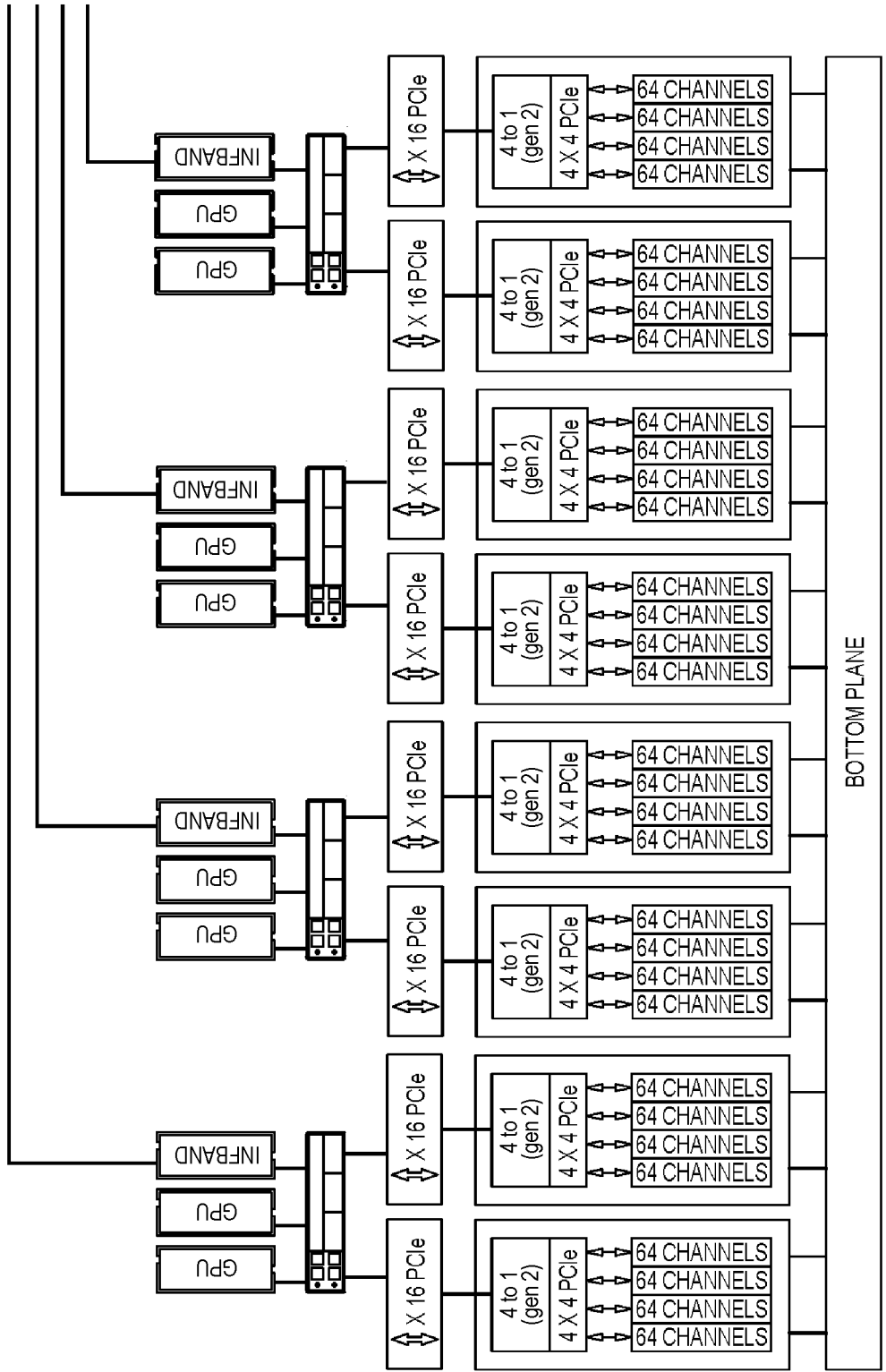
FIG. 11B is an enlarged view of a portion of the high-performance computer network of FIG. 11A.

FIG. 11A is a diagram of an exemplary embodiment of a scalable computing network suitable to meet the processing needs for HABIS as described herein. For example, FIG. 11A shows the interconnections of a 21-node network that is comprised of 20 hybrid (acquisition and computation) nodes and a head (or control) node, which supervises the computing network. In this embodiment, the 40 data-acquisition boards are arranged in five groups of eight. Two data-acquisition boards are connected to each of the 20 computing nodes. The head node may also serve as a console for rendering images and for controlling the instrument. FIG. 11B shows a group of eight boards and their corresponding nodes in greater detail. The 20 computing nodes, each with two GPUs, form an efficient numerical engine for massively parallel computations. Single-precision GPUs are ideal computational engines for several reasons. Since the data acquired from the hemispheric transducer have 14 bits of precision, and since the computations applied to this data are not numerically unstable, single-precision arithmetic is sufficient. In fact, reduced memory requirements and faster transfer rates associated with single-precision data make this format desirable. Each reconstruction requires a very large number (about $50 \times 10^{15}$ floating-point operations, i.e., 50 petaflops) of single-precision operations. Each node receives data from two of the 40 sets of data-acquisition electronics (shown as the green rectangles that contain four 64-channel blocks in FIG. 11B) via fast PCIe connections. Four GPUs are also connected to each node to form a powerful single-precision computational engine for parallel processing. InfiniBand connections to a central switch enable rapid inter-node communication necessary between stages of the computation. These switches allow 20 InfiniBand connections to be active simultaneously. In one embodiment, all the nodes of the network can also be connected to a local Ethernet switch (not shown) for command, control, and monitoring. A high-speed connection of the local Ethernet to the Internet further enables command, control, and monitoring from a remote location.

The reconstruction algorithm, which is described in detail later herein, can be parallelized at both a high and a low level. The high-level parallelization factors the computations into large-scale operations that are performed independently on separate nodes. The low-level parallelization reduces these operations to a succession of vector and matrix computations that can be implemented as GPU kernels. Also, only a modest amount of logic is needed to direct the flow of data and to sequence the computations. Careful sequencing of these kernels can use the asynchronous data transfer capability of currently available general-purpose GPUs to eliminate data transfer latencies, resulting in improved efficiency. Data-transfer latencies are further suppressed by generation 3 PCIe connections used in currently available general-purpose GPUs.

During an approximately two-second period of data acquisition that comprises a volume scan by HABIS, each of the 40 sets of data-acquisition electronics subassemblies receives 10,240 waveforms from 256 different transducer elements. For a sampling rate of 20 MHz over a time interval of 204.8 µs and for two bytes per sample, all of which are representative of those used in HABIS, a total of (2 bytes per sample)×(20 samples per s)×(204.8 µs per waveform)×(10,240 waveforms per element)×(256 elements)=21.47483×$10^{10}$ bytes or about 21.5 gigabytes (GB) are acquired and stored by each set of electronics. As mentioned previously, if a separate computational facility were used for reconstruction, then the data from all 40 sets of the data-acquisition electronics (i.e., a total of 40×21.47483×1010 bytes=8.589934×$10^{11}$ bytes or about 0.859 TB) would need to be aggregated and transferred to that facility, a time-consuming process given the large amount of data to be transferred.

Figure 12:
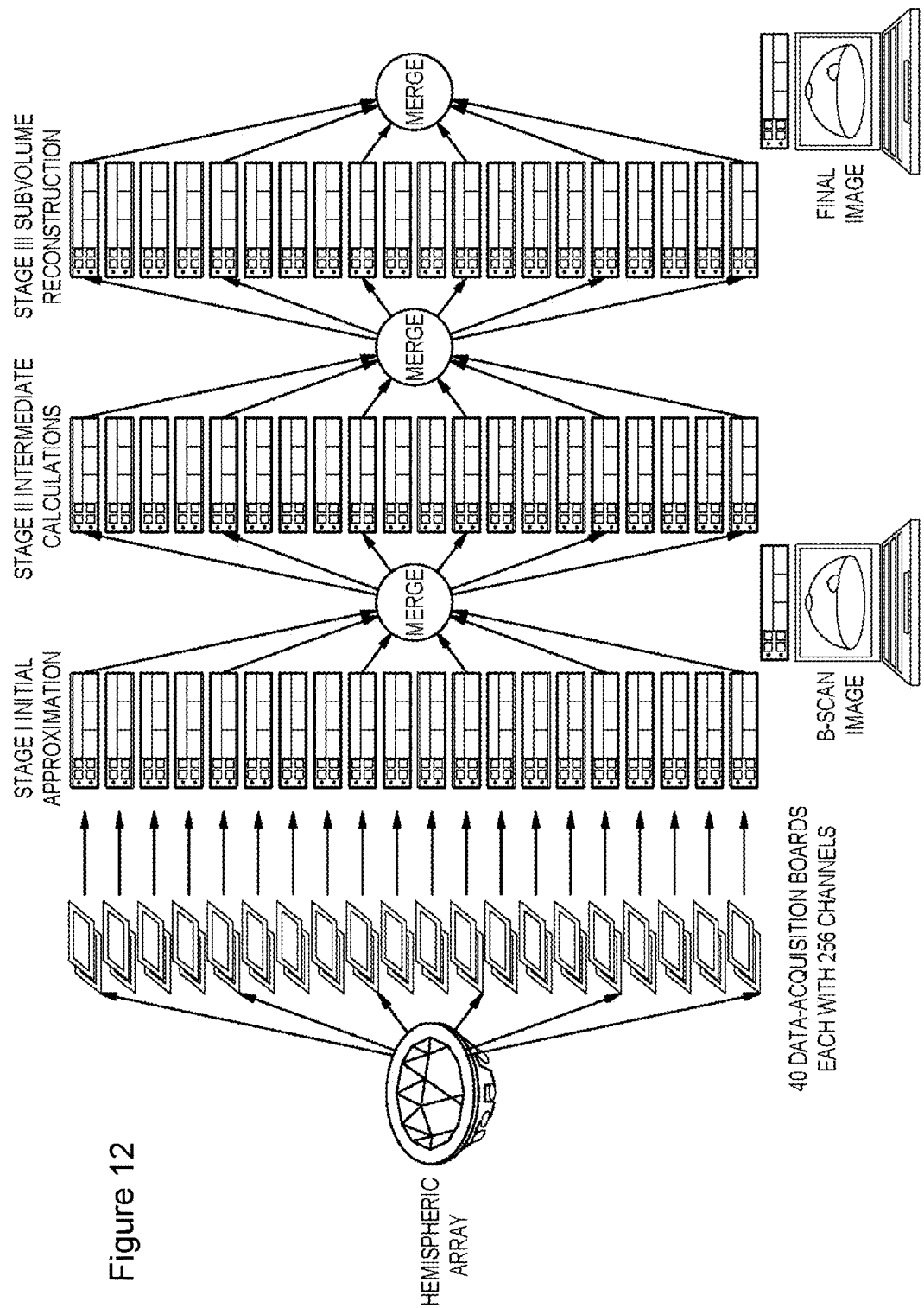
FIG. 12 is a diagram of a data processing flow through an exemplary HABIS and associated high-performance computer network.

As contemplated herein, FIG. 12 illustrates an exemplary data processing flow (via the image reconstruction algorithm) that permits processing to be performed in stages that consist of parallel computations on each node. As shown, these parallel computations on one node may be completely independent of the computations on the other nodes. As shown in FIG. 12, Stage I operations include preprocessing steps (such as time-variable gain compensation, transmission decoding, and application time gates to isolate the response from different regions), b-scan imaging, and initial approximation of the scattering object. Stage II operations include split-step propagation of fields that emanate from each of the 10,240 transducer elements and pass through the approximate scattering object, reduction of these fields to simplified representations each limited to a single subvolume, and estimation of the portions of the scattering measurements attributable to the approximate scattering object. Stage III operations produce a refined approximation of the scattering object by using residual scattering measurements to reconstruct residual medium variations in each subvolume. After each stage of computations, the results of the computations at each node are redistributed to other nodes for the next stage of computations.

Computational efficiency and cost-effective implementation of the staged processing scheme described above were the main criteria used to design the high-performance computer network. Two key requirements follow from these criteria. One requirement is that the nodes must have enough computational capacity to complete each stage of computation in a timely manner. The other requirement is that the nodes must be able to exchange data rapidly enough so that data redistribution is not a bottleneck.

The computer nodes must also be endowed with enough memory to insure that the GPUs can be continuously supplied with input data, and also have enough storage for intermediate results so that saving and recalling data from disk files is unnecessary. In one embodiment, each HABIS compute node is equipped with four GPUs and a total of 128 GB of memory. These allocations allow each node to conduct four completely independent parallel computations during each processing stage. This combination of resources results in relatively low-cost compute nodes that have precisely the right kind of numerical capability for efficient implementation of the HABIS algorithm. In other embodiments, each HABIS compute node can include a different number of GPUs and/or memory, as would be understood by a person skilled in the art.

The transfer of data from the acquisition apparatus to the computer network and the node-to-node data transfers that occur after each stage of computation all involve large volumes of data. Each compute node in the architecture is responsible for collecting a receive signal of 4,096 two-byte temporal samples from a group of 512 receive channels for each of 10,240 transmissions. Based on the previously-noted volume of data for a 256-channel set, the total volume of all these samples is about 43 GB. Excluding overhead, this volume of data can be transferred over a fast 16-lane PCIe connection with an overall transfer rate of 8 GB/s in about 5.4 seconds and can be transferred over a pair of such PCIe connections in about 2.7 seconds.

Preprocessing occurs initially in each node without inter-node communication and consists of transmit-receive channel response equalization, compensation for time-varying gain, Fourier transformation, and signal decoding requires expansion of the two-byte samples to a larger size. In HABIS, although other expansions are possible, the expansion to a larger size is accomplished by conversion of the two-byte integer samples into four-byte floating-point values. This increases the volume of data associated with one node to 86 GB from 43 GB. Although Fourier transformation that is part of the preprocessing expands the four-byte floating-point values to complex values each occupying eight bytes, the volume of the complex data is orders of magnitude less if only a set of Fourier components in the useful bandwidth of the system are retained and the relation between positive and negative frequencies imposed by real temporal signals is used. In view of this, node-to-node data transfers that proceed subsequent processing involve smaller volumes of data.

The required node-to-node transfers can be performed quickly using InfiniBand connections instead of PCIe connections. The efficiency of InfiniBand connections is illustrated by considering the transfer of results from the parallel Stage II calculations, i.e., the scattering-measurement matrix $\tilde{M}$ with entries $\tilde{M}_{mn}$ for the approximate scattering object. This matrix is comprised 10,240×10,240 complex numbers that are each eight bytes. Thus, the size of the entire matrix is about 0.84 GB, of which one-twentieth resides on each compute node. The aggregation of the entire matrix at each node for the Stage III computations requires a total transfer of $$\underbrace{20}_{\substack{\text{Nodes that contain} \\ \text{a portion of } \tilde{M}_{nn}}} \times \qquad \text{Eq. (30)}$$

$$\underbrace{0.84 \text{ GB}/20}_{\substack{\text{Size of each} \\ \text{portion of } \tilde{M}_{nn}}} \times \underbrace{19}_{\substack{\text{Nodes to get} \\ \text{each portion}}} = 16 \text{ GB.}$$

For a 4X QDR InfiniBand connection that, excluding overhead, has a data transfer rate of about 4 GB/s (i.e., 32 Gb/s), this transfer can be completed in four seconds using a single InfiniBand connection, and can be completed in about 0.2 seconds using 20 simultaneously-active InfiniBand connections.

Communication and Control

The preprocessing and b-scan imaging that take place in Stage I are performed with no communication between the 20 nodes in the network. However, full inverse scattering reconstruction is completed by the Stage II and Stage III computations that require node-to-node transfers of data over the InfiniBand network. The 20 nodes also need to receive commands from an operator using a terminal to control the data collection, processing operations, b-scan image formation, and image reconstruction via inverse scattering. Communication software provides the necessary capabilities for data exchange, distributed control, and coordinated calculations among the nodes. Each of the 20 nodes includes a library that provides an interface to the other 19 nodes and a head node with a keyboard and monitor. From the head node, commands originated by an operator can be broadcast to the 20 computing nodes by using control program that runs on each node. The program can include logic that allows each node to determine its data-acquisition functions from the operator-originated requests. The program also supervises the preprocessing calculations. Additional programs that run on all the nodes form b-scan images and reconstruct images via inverse scattering. The terminal that accepts operator commands can be used as a user interface that runs on one of the 20 nodes or, alternatively, on the head node.

HABIS Algorithm

Inverse Scattering Framework

Monochromatic, i.e., single-frequency, measurements of scattering measurements are used in the HABIS imaging algorithm. The measurements are conveniently arranged as a two-dimensional matrix M of complex values with 10,240 rows and 10,240 columns. The value of the matrix entry $M_{mn}$ with row index m and column index n is the scattering amplitude that is measured at the n-th receiving element in response to a transmission from the m-th element.

Scattering objects are reconstructed by determining variations of the background medium $\Delta\eta(x)$ that account for the observed scattering measurements. This determination requires a mathematical model that relates the medium variations to the scattering measurements. A weak-scattering model, i.e., one in which the scattered wave is small relative to the incident wave, is desirable because the scattering measurements in a weak-scattering model depend linearly on the medium variations. The explicit expression for weak scattering is $$M_{mn} = \int \psi_n(x)\psi_m(x)\Delta\eta(x)d^3x \qquad \text{Eq. (1)}$$

where $\psi_m(x)$ denotes the spatially varying amplitude of the field that is transmitted by element m and propagates through an empty background, and $\psi_n(x)$ denotes the spatially varying sensitivity pattern of receiver n that also propagates through an empty background. The transmit field of element n is the same as the receive sensitivity pattern of element n.

Unfortunately, weak scattering is usually not very accurate in practical applications because, in actual measurements, the value $\psi_m(x)$ of the transmit field that appears in the integrand of Eq. (1) is altered by medium variations encountered between the transmit element and x, and, likewise, the value $\psi_n(x)$ of the receiver sensitivity pattern that also appears in the integrand of Eq. (1) is altered by medium variations encountered between x and the receive element. A more accurate model of the scattering measurements is formulated by incorporating an approximate scattering object in the scattering expression. This yields the revised scattering expression $$M_{mn} - \tilde{M}_{mn} = \int \tilde{\psi}_n(x)\tilde{\psi}_m(x)\Delta\eta(x)d^3x \qquad \text{Eq. (2)}$$

where $\tilde{\psi}_m(x)$ denotes the spatially varying amplitude of the field transmitted from element m that propagates through the approximate object, $\tilde{\psi}_n(x)$ denotes the spatially varying sensitivity pattern of receiver n that propagates through the approximate object, $\tilde{M}_{mn}$ denotes the scattering from the approximate object, and $\Delta\eta(x)$ denotes medium variations that are relative to the approximate object.

The integral on the right side of Eq. (2) is a distorted weak scattering expression for the residual scattering measurement $M_{mn} - \tilde{M}_{mn}$. Equation (2) reduces to the original weak scattering expression given by Eq. (1) when an empty background is used for the approximate scattering object, but Eq. (2) is more accurate than Eq. (1) when the approximate object is a good approximation of the true object. For this reason, inverse scattering algorithms are usually iterative. In each iteration, the approximate scattering object $\eta q(x)$ is improved by appending a refinement term $\Delta\eta(x)$ that is derived from Eq. (2). This is the general framework for inverse scattering. The main differences between specific implementations are in the way that the refinements are estimated.

An important feature of these iterative procedures in breast imaging applications is that the quality of refinements to the approximate scattering object does not improve uniformly. The reason for this can be found in Eq. (2) and does not depend on the way that $\Delta\eta(x)$ is estimated. In Eq. (2), the contribution to the residual scattering measurement $M_{mn} - \tilde{M}_{mn}$ that is due to the medium variation $\Delta\eta(x)$ at x is weighted by the factor $\tilde{\psi}_n(x)\tilde{\psi}_m(x)$. However, $\tilde{\psi}_n(x)$ and $\tilde{\psi}_m(x)$ are approximate oscillatory signals that do not take into account the influence of variations to the approximate object that are encountered as the fields propagate to x from the transmit element, and from x to the receive element. If these influences cause appreciable phase shifts in $\tilde{\psi}_n(x)$ and $\tilde{\psi}_m(x)$, then the scattering contribution that Eq. (2) attributes to $\Delta\eta(x)$ will be weighted erroneously. Thus, Eq. (2) is only an accurate expression of the relationship between the scattering measurements and the medium variations in regions where the field approximations $\tilde{\psi}_n(x)$ and $\tilde{\psi}_m(x)$ are accurate, and any estimate of $\Delta\eta(x)$ that is derived from Eq. (2) can only be expected to improve the approximation of the scattering in these regions. Furthermore, to make significant improvements in the accuracy of the field approximations a global update of the approximate scattering object is needed that refines the medium variations along the full range of propagation paths that emanate from the transducer elements. These circumstances result in very slow convergence of the iterative refinements described above when the true scattering object is poorly approximated. However, much more rapid convergence can be expected when the approximate scattering object is close enough to the true object to allow accurate representation of transmit fields and receiver sensitivity patterns.

The HABIS imaging algorithm substitutes a two-step procedure for the general iterative scheme outlined above. First, an approximate scattering object is estimated to obtain field approximations that are good enough to ensure that Eq. (2) is accurate in the region of interest. A single inverse-scattering refinement is then computed to produce a sharper and more detailed reconstruction of the medium variations in this region. Starting with a high-quality initial estimate can bypass many iterations in the early stage when convergence is slow. The method used to obtain the initial approximation to the scattering object and the method used for iterative refinement of the scattering object are described in the sections below along with other important aspects of the HABIS imaging methodology.

Although formation of the initial approximation logically precedes iterative refinement, the method for iterative refinement is discussed first as this method is more fundamental.

Refinement of an Approximate Scattering Object

In this section, the following quantities are assumed to be known:

$\eta(x)$: medium variations that constitute an approximate scattering object $\tilde{\psi}_m(x)$: spatially varying amplitude of field transmitted from element m that propagates through $\eta(x)$ $\tilde{\psi}_n(x)$: spatially varying sensitivity pattern of receiver n that propagates through the approximate object $\tilde{M}_{mn}(x)$: computed scattering from $\eta(x)$ that would be received at element n in response to a transmission from element m, (m, n=1, 2, . . . , 10,240)

$M_{mn}$: measured scattering that is received from the true object at element n in response to a transmission from element m (m, n=1, 2, . . . , 10,240)

The above list includes all the terms that appear in Eq. (2) except for the unknown variation $\Delta\eta(x)$. The methods that are used to estimate $\Delta\eta(x)$ from Eq. (2) are described below.

First estimate of $\Delta\eta(x)$

The typical strategy for estimation of $\Delta\eta(x)$ is to adopt a finite-dimensional representation of $\Delta\eta(x)$ that reduces Eq. (2) to a system of linear equations. Some commonly used parameterizations of $\Delta\eta(x)$ include: sample values at the vertices of a rectilinear grid, a linear combination of sincfunctions that are centered at the vertices of a rectilinear grid, or a linear combination of the eigenfunctions of a scattering operator. The systems of equations that result from these parameterizations are usually either underdetermined or overdetermined and must be supplemented with auxiliary conditions, such as norm minimization, to ensure that the solution is unique and well-conditioned. In many cases, the numerical problems associated with solving these large systems of equations are significant.

The approach used by the HABIS algorithm avoids these time-consuming numerical challenges. The value of $\Delta\eta(x)$ at each location is assumed to depend linearly on the residual scattering measurements and may, therefore, be estimated by $$\widetilde{\Delta\eta}(x) = \sum_{n,m=1}^{10,240} \alpha_{nm}(x)(M_{mn} - \tilde{M}_{mn}) \qquad \text{Eq. (3)}$$

where $\alpha_{nm}(x)$ is a matrix of coefficients that varies from point to point. To determine these coefficients the expression on the right side of Eq. (2) is substituted for the residual scattering measurement $M_{mn} - \tilde{M}_{mn}(x)$ that appears on the right side of Eq. (3). Exchanging the order of the sum and the integral gives $$\widetilde{\Delta\eta}(x) = \int \left[\sum_{n,m=1}^{10,240} \alpha_{nm}(x)\tilde{\psi}_n(x')\tilde{\psi}_m(x')\right]\Delta\eta(x')d^3x' \qquad \text{Eq. (4)}$$

The quality of this estimate depends on how closely the bracketed term in Eq. (4) approximates the translated $\delta$-function $\delta(x'-x)$. A natural way to realize this approximation is to set $\alpha_{nm}(x) = \beta_n(x)\beta_m(x)$, where the $\beta$ factors are chosen to form a synthetic focus of the transmit and receive fields at x. For example, if $\beta_m(x) = 1/\tilde{\psi}_m(x)$ and $\beta_n(x) = 1/\tilde{\psi}_n(x)$, then the bracketed sum in Eq. (4) is equal to $$\left[\sum_{m=1}^{10,240} \frac{\tilde{\psi}_m(x')}{\tilde{\psi}_m(x)}\right]^2$$

The value of this double sum is $(10,240)^2$ when $x'=x$. At other locations, however, the magnitude of the sum is much smaller because at other locations the summands do not accumulate coherently. Thus, the bracketed term in Eq. (4) is concentrated at values of x' that are near x when $\alpha_{nm}(x) = \beta_n(x)\beta_m(x)$.

Improvement of the Estimate of $\Delta\eta(x)$

Several adaptations of the estimate in Eq. (3) are needed, however, to normalize and to improve the accuracy of the estimate. These adaptations are facilitated by subdivision of the scattering object into overlapping subvolumes. Refinements of the approximate scattering object in each subvolume are estimated independently. These refinements are then blended together in the regions where the subvolumes overlap. For the rest of this section, the procedures for estimating $\Delta\eta(x)$ are intended for application to variations within a single rectangular subvolume. Also, for the rest of this section, the origin of the spatial coordinate system is assumed to be the center of the subvolume.

Setting $\alpha_{nm}(x) = \beta_n(x)\beta_m(x)$ yields, for the bracketed term in Eq. (4), the expression $$K(x, x') = \sum_{n,m=1}^{10,240} \beta_n(x)\beta_m(x)\tilde{\psi}_n(x')\tilde{\psi}_m(x') \qquad \text{Eq. (5)}$$

where K (x, x') may be interpreted as the imaging kernel for the estimate $$\widetilde{\Delta\eta}(x) = \sum_{n,m=1}^{10,240} \beta_n(x)\beta_m(x)(M_{mn} - \tilde{M}_{mn}). \qquad \text{Eq. (6)}$$

The kernel given by Eq. (5) is not translation invariant, but is nearly translation invariant in local neighborhoods. Thus, for sufficiently small subvolumes Eq. (4) can be rewritten $$\widetilde{\Delta\eta}(x) = \int K(x, x' - x)\Delta\eta(x')d^3x' \qquad \text{Eq. (7)}$$
$$= \int K(x' - x, 0)\Delta\eta(x')d^3x'.$$

This equation expresses the estimate $\widetilde{\Delta\eta}(x)$ as the convolution of $\Delta\eta(x)$ with the impulse response $$K(x, 0) = \sum_{n,m=1}^{10,240} \beta_n(x)\beta_m(x)\tilde{\psi}_n(0)\tilde{\psi}_m(0). \qquad \text{Eq. (8)}$$

The representation of $\widetilde{\Delta\eta}(x)$ given by Eq. (7) implies that a more accurate and normalized estimate, $\widehat{\Delta\eta}(x)$, can be derived by deconvolution of K (x, 0) from $\widetilde{\Delta\eta}(x)$. However, this deconvolution can only reconstruct spatial-frequency components of $\Delta\eta(x)$ at the spatial frequencies where the Fourier transform of K (x, 0) is appreciable. This range of usable spatial-frequency components is constrained by the boundaries of the solid angle of incident directions of the transmit fields (and, equivalently, by the receiver sensitivity patterns) that illuminate the subvolume, and also by the temporal-frequency of the scattering measurements. For subvolumes that are contained in the interior of the hemisphere, these limitations confine the usable spatial frequencies to an asymmetric region that includes the spatial-frequency origin.

Further improvement of $\tilde{\Delta\eta}(x)$ is realized by extending the set of usable spatial frequencies to a symmetric region that contains the original asymmetric region. The improvement is accomplished by using low-spatial-frequency components of $\tilde{\Delta\eta}(x)$ to model the relationship between the real and imaginary parts of $\Delta\eta(x)$. This relationship, together with symmetry properties of the Fourier transform, can then be used to evaluate spatial-frequency components of $\Delta\eta(x)$ at spatial frequencies that are antipodal to the spatial frequencies in the original asymmetric region. This results in the final estimate $\tilde{\tilde{\Delta\eta}}(x)$ of the $\Delta\eta(x)$ that is used to add detail and resolution to the approximate scattering object.

Accordingly, important aspects of the procedure described above that are different from other inverse scattering methods include: 1) The HABIS procedure for estimating $\Delta\eta(x)$ separates the overall estimate into estimates for each of the subvolumes that can be computed independently. The computations are, therefore, ideally suited to high-level parallelization that assigns estimates of each subvolume to a different compute node of a high-performance computer network; 2) The estimate in each subvolume is found by direct computations (i.e., computations that are not directed by conditions that depend on results of prior computations) and that can be 'vectorized,' i.e., executed in parallel. This is the ideal setting for the kind of low-level parallelization that is provided by numerical acceleration engines such as graphics processing units known as GPUs; and 3) The initial estimate $\tilde{\Delta\eta}(x)$ that is obtained from synthetic focusing is not as accurate as estimates that are derived from more costly algorithms, but the improved estimates $\tilde{\Delta\eta}(x)$ and $\tilde{\tilde{\Delta\eta}}(x)$ are able to restore full accuracy with only a fractional increase in computation.

Initial Approximation of the Scattering Object

An initial approximation of the scattering object is found by imaging methods that are similar to b-scan algorithms used in currently available commercial ultrasound imaging systems. As noted in the preceding section, initial estimates with good accuracy are needed to eliminate slowly converging iterations. These estimates are developed from a scattering model that is similar to the weak scattering model of Eq. (1), but with an important difference. The scattering measurements used to form the initial estimate are temporal responses to a pulse transmission while the scattering measurements represented by Eq. (1) are amplitudes of harmonic responses to monochromatic transmissions.

For efficient computation, the medium variations are estimated in subvolumes that can be reconstructed in parallel. However, in this case, the interior of the hemisphere is partitioned into tetrahedrons rather than cubes. Each tetrahedron has one vertex at the origin of the hemisphere, and three other vertices that form a subtriangle of one of the triangular facets of the hemispheric array. FIG. 10 shows the tetrahedral regions that are associated with subtriangle A of the hemispheric array. Since the hemispheric array previously described herein consists of 40 facets and each facet is divided into four subtriangles, the interior of the hemisphere is partitioned into 160 tetrahedrons.

The medium variations in each tetrahedron are estimated from the scattered signals that are received by the 64 transducer elements contained in the subtriangle of the hemispheric array that forms the outer face of the tetrahedron. Since the data-acquisition apparatus transfers all the received signals from the elements in this subtriangle to the same compute node, the signals are automatically distributed in data sets that are suitable for this parallel computation. Each receive element collects a total of 10,240 signals. However, only 256 of these signals are used in the estimate of the medium variations in the tetrahedron that is bounded by subtriangle A because the estimate of this subvolume only uses signals from transmit elements that belong either to subtriangle A or belong to one of the three subtriangles $A^1$, $A^2$, $A^3$ that have a common edge with subtriangle A.

Imaging Algorithm

To derive a mathematical scattering expression for the b-scan model, let p(t) denote the incident pulse that is used to excite the transmit elements that is centered at t=0. If directional effects and aberration are neglected, then the pressure variations at x that result from the transmit element at $x_m$ are given by $p(t-\|x-x_m\|/c_0)/\|x-x_m\|$, where $c_0$ is the average speed of sound in the medium. Reflections of this incident wave that are caused by an inhomogeneity $\eta(x)$ at x are detected by the receiver element at $x_n$ as the signal.

$$\frac{p(t - \delta_{nm}(x))}{\|x - x_m\|\|x - x_n\|}\eta(x) \qquad \text{Eq. (9)}$$

where $\delta_{nm}(x)$ denotes the geometric time delay $(\|x-x_m\|+\|x-x_n\|)/c_0$. Since reflections can come from any illuminated inhomogeneity, the total reflected pressure detected at $x_n$ is given by $$\varphi_{mn}(t) = \int \frac{p(t - \delta_{nm}(x'))}{\|x' - x_m\|\|x' - x_n\|}\eta(x)d^3x'. \qquad \text{Eq. (10)}$$

Equation (10) is a representation of one temporal signal in the complete map of 10,240×10,240 element-to-element responses. The strength of the reflector $\eta(x)$ at location x in subtriangle A is estimated by forming the sum $$\varphi(x, t) = \sum_{m \in A \cup A^1 \cup A^2 \cup A^3} \sum_{n \in A} \|x' - x_m\|\|x' - x_n\|\varphi_{mn}(t + \delta_{nm}(x)) \qquad \text{Eq. (11)}$$

of received signals with time offsets that cancel the delays to and from the reflector. Substituting Eq. (10) into Eq. (11) and assuming that the norms in the numerator of Eq. (11) are canceled by the norms in the denominator of Eq. (10) gives $$\varphi(x, t) = \qquad \text{Eq. (12)}$$
$$\int \left[\sum_{m \in A \cup A^1 \cup A^2 \cup A^3} \sum_{n \in A} p(t + \delta_{nm}(x) - \delta_{nm}(x'))\right]\eta(x')d^3x'.$$

The $\delta_{nm}(x)$ geometric time shifts that are used to form the sum in Eq. (11) perform the same focusing function as the $\beta$-factors that are used in Eq. (6) to focus monochromatic responses. Evaluation of Eq. (12) at t=0 gives the expression $$\varphi(x, 0) = \int \left[\sum_{m \in A \cup A^1 \cup A^2 \cup A^3} \sum_{n \in A} p(\delta_{nm}(x) - \delta_{nm}(x'))\right]\eta(x')d^3x' \qquad \text{Eq. (13)}$$

that represents $\psi(x, 0)$ as the imaged value of $\eta(x)$ that results from the imaging kernel $$K(x, x') = \sum_{m \in A \cup A^1 \cup A^2 \cup A^3} \sum_{n \in A} p(\delta_{nm}(x) - \delta_{nm}(x')). \quad \text{Eq. (14)}$$

However, the limited range of transmit and receive directions that are included in Eq. (14) yields an oscillatory imaging kernel that does not have low spatial-frequency components. To eliminate oscillations in the imaged values that are introduced by this kernel the medium variations are estimated by the value of the complex envelope of ψ(x, t) at t=0 rather than by the value of ψ(x, t) at t=0. Thus, $$\tilde{\eta}(x) = Env[\varphi(x,t)]_{t=0} \quad \text{Eq. (15)}$$

Envelope detection entails demodulation, i.e., multiplication by $e^{j\omega_0 t}$, where $\omega_0$ is the nominal center or carrier frequency of the pulse p (t), followed by a lowpass filter. However, since only one value of the envelope, i.e., the value at t=0, is required, both operations can be consolidated into the inner product $$\tilde{\eta}(x) = Env[\varphi(x,t)]_{t=0} = \int \omega(x,t) e^{j\omega_0 t} h_{LP}(t) dt, \quad \text{Eq. (16)}$$

where $h_{LP}$ (t) denotes the impulse response of the lowpass filter. These computations can also be accomplished using frequency components of the received signals rather than time samples. In that case, Eq. (11) and Eq. (16) have the forms $$\varphi(x, \omega) = \quad \text{Eq. (17)}$$

$$\sum_{m \in A \cup A^1 \cup A^2 \cup A^3} \sum_{n \in A} \|x' - x_m\| \|x' - x_n\| \varphi_{mn}(\omega) e^{-j\omega \delta_{nm}(x)}$$

and $$\tilde{\eta}(x) = \int \varphi(x, \omega) H_{LP}(\omega - \omega_0) dt, \quad \text{Eq. (18)}$$

where $H_{LP}$ (ω) is the frequency response or transfer function of the lowpass filter.

Unfortunately, envelope detection is a nonlinear process that produces imaged values that do not map to mechanical properties of the medium. The estimate $\tilde{\eta}$(x) is, therefore, only used to identify the structure of the scattering object. Explicit values of the medium variations that are assigned to this structure are determined by other means.

The computations that assign values of sound speed and attenuation to the medium variations in subtriangle A make use of aberration estimates at a series locations $x_1^A$, $x_2^A$, ... along the line from the center of the subtriangle to the center of the hemisphere (See FIG. 10). These aberration estimates are also used to compensate the receive signals in Eq. (11) to improve the accuracy of the estimate 4(x) given by Eq. (15). Estimation of aberration is, therefore, a key step in this imaging procedure, and is described below.

Aberration Estimation

If the transmission paths to and from the reflector at x are not homogeneous, then the time delays of arrival times for reflections from x will have the form $$\delta_{nm}(x) + \varepsilon_m(x) + \varepsilon_n(x) \quad \text{Eq. (19)}$$

where $\varepsilon_m$ (x) and $\varepsilon_n$ (x) are adjustments to the geometric delay $\delta_{nm}$ (x) that account for changes in sound speed between the transmitter at $x_m$ and x, and between x and the receiver at $x_n$. These terms cause misalignment of the time signals in the summation in Eq. (11) or, equivalently, phase variations in the frequency components that appear in the summation in Eq. (17). This results in a blurring of the estimate 4(x). However, if the terms $\varepsilon_m$ (x) and $\varepsilon_n$ (x) can estimated, then the estimated delays can be deducted from the geometric delay factors to restore signal alignment.

In practice, only the difference in the time delays associated with neighboring elements can be readily estimated. To describe this time-difference computation, let $x_n$ and $x_n'$ be adjacent receive elements. Also, let $$\varphi^{(n)}(x, t) = \sum_{m \in A \cup A^1 \cup A^2 \cup A^3} \|x - x_m\| \|x - x_n\| \varphi_{mn}(t + \delta_{nm}(x)) \quad \text{Eq. (20a)}$$

and $$\varphi^{(n')}(x, t) = \sum_{m \in A \cup A^1 \cup A^2 \cup A^3} \|x - x_m\| \|x - x_{n'}\| \varphi_{mn'}(t + \delta_{nm'}(x)) \quad \text{Eq. (20b)}$$

be sums of the delayed signals for all 256 transmit elements and one or the other of the receive elements n and n'. These expressions have the same form as Eq. (11) except that only one receive element is included in the sum. A relationship between these two summed signals is derived by using Eq. (10) to represent each of the element-to-element signals, but with the adjusted delays $\delta_{nm}$ (x')+$\varepsilon_m$ (x')+$\varepsilon_n$ (x') in place of the simple geometric delays $\delta_{nm}$ (x'). This gives $$\varphi^{(n)}(x, t) = \quad \text{Eq. (21a)}$$

$$\int \left[ \sum_{m \in A \cup A^1 \cup A^2 \cup A^3} p(t + \delta_{nm}(x) + \varepsilon_m(x) + \varepsilon_n(x) - \delta_{nm}(x')) \right] \eta(x') d^3 x'$$

and $$\varphi^{(n')}(x, t) = \quad \text{Eq. (21b)}$$

$$\int \left[ \sum_{m \in A \cup A^1 \cup A^2 \cup A^3} p(t + \delta_{n'm}(x) + \varepsilon_m(x) + \varepsilon_{n'}(x) - \delta_{n'm}(x')) \right] \eta(x') d^3 x'.$$

Since the receiver elements n and n' are adjacent to each other, the geometric delays $\delta_{nm}$ (x)–$\delta_{nm}$ (x') and $\delta_{n'm}$(x)–$\delta_{n'm}$ (x') will be nearly identical. If, in addition, the delays $\varepsilon_n$ (x) and $\varepsilon_{n'}$ (x) are essentially constant near the focal point, then $$\varphi^{(n')}(x,t) = \varphi^{(n)}(x, t + \varepsilon_{n'}(x) - \varepsilon_n(x)). \quad \text{Eq. (22)}$$

Thus, the two summed signals in Eq. (21a) and Eq. (21b) only differ by the time shift $\varepsilon_{n'}$ (x)-$\varepsilon_n$ (x). This time shift is usually estimated by finding the peak of the cross correlation of the two signals. Frequency-domain computations may also be used. In that case, the summed frequency responses $$\varphi^{(n)}(x, \omega) = \sum_{m \in A \cup A^1 \cup A^2 \cup A^3} \|x' - x_m\| \|x' - x_n\| \varphi_{mn}(\omega) e^{-j\omega \delta_{nm}(x)} \quad \text{Eq. (23a)}$$

And $\varphi^{(n')}(x, \omega) = \quad \text{Eq. (23b)}$ $$\sum_{m \in A \cup A^1 \cup A^2 \cup A^3} \|x' - x_m\| \|x' - x_{n'}\| \varphi_{mn'}(\omega) e^{-j\omega \delta_{n'm}(x)}$$

are formed instead of the summed signals in Eq. (20a) and Eq. (20b). The time shift difference $\varepsilon_{n'}(x)-\varepsilon_n(x)$ is then estimated from the relationship $$\varphi^{(n')}(x,\omega)=\varphi^{(n)}(x,\omega)e^{j\omega[\varepsilon_{n'}(x)-\varepsilon_n(x)]}. \qquad \text{Eq. (24)}$$

Estimates of the time shift differences for every pair of adjacent receive elements in triangular subdivisions can be summed along paths from the central element to form estimates $\tilde{\varepsilon}_n(x)$ of the time shifts at each of the 64 receiving elements. These estimates can then be used to adjust the geometrically-determined phase shifts to compensate for aberration along the ray paths to the receiving elements. Range-dependent compensation for attenuation can be included by using amplitude factors along with the phase factors for time shift compensation on receive.

Aberration estimates for the paths to the transmit elements may be obtained by a similar procedure. Differences in the transmit delays are estimated by forming the summed frequency responses $$\varphi^{(m)}(x,\omega) = \sum_{n \in A} \|x'-x_m\|\|x'-x_n\|\varphi_{mn}(\omega)e^{-j\omega[\delta_{nm}(x)+\varepsilon_n(x)]} \text{ and} \qquad \text{Eq. (25a)}$$

$$\varphi^{(m')}(x,\omega) = \sum_{n \in A} \|x'-x_{m'}\|\|x'-x_n\|\varphi_{m'n}(\omega)e^{-j\omega[\delta_{nm'}(x)+\varepsilon_n(x)]} \qquad \text{Eq. (25b)}$$

for each adjacent pair m, m' of transmit elements. These equations parallel Eq. (23a) and Eq. (23b), but include time shifts to correct for aberration along the paths to the receive elements. The time shift $\varepsilon_{n'}(x)-\varepsilon_n(x)$ is estimated from the relationship $$\varphi^{(m')}(x,\omega)=\varphi^{(m)}(x,\omega)e^{j\omega[\varepsilon_{m'}(x)-\varepsilon_m(x)]} \qquad \text{Eq. (26)}$$

Similar estimates for time shift differences between every pair of adjacent transmit elements in the triangle A and the three surrounding triangular subdivisions are summed along paths from the central element to form estimates $\tilde{\varepsilon}_m(x)$ for the time shifts at each of the 256 transmitting elements.

The aberration time shifts $\tilde{\varepsilon}_n(x)$ and $\tilde{\varepsilon}_m(x)$ found from these computations are used to form the compensated time delays $$\tilde{\delta}_{nm}(y)=\delta_{nm}(y)+\tilde{\varepsilon}_m(x)+\tilde{\varepsilon}_n(x) \qquad \text{Eq. (27)}$$

for imaging via Eq. (17) and Eq. (18) at locations y that are close to x.

The root-mean-square size of the aberration delays generally increases with depth. Also, estimates of the time delay differences between adjacent elements become inaccurate when the aberration is strong. Additional processing is then needed to detect and correct for circulation errors in the time delay differences or to form intermediate estimates of delay differences between adjacent clusters of elements. These complications are avoided by evolving the aberration delays along the line from the center of the triangle of receive elements to the origin of the hemisphere. Referring now to FIG. 10, initial aberration estimates at $x_1^A$ are formed at a depth that is shallow enough to insure that the aberration is weak. The aberration at $x_2^A$ will be stronger. However, the aberration at $x_2^A$ can be computed using geometric delays that are already compensated by the estimated aberration at $x_1^A$. Thus, at each step, only the incremental aberration is estimated. A focus of this approach is to implement aberration correction as a straightforward computation that does not require conditional logic.

Image Consolidation

Figure 13:
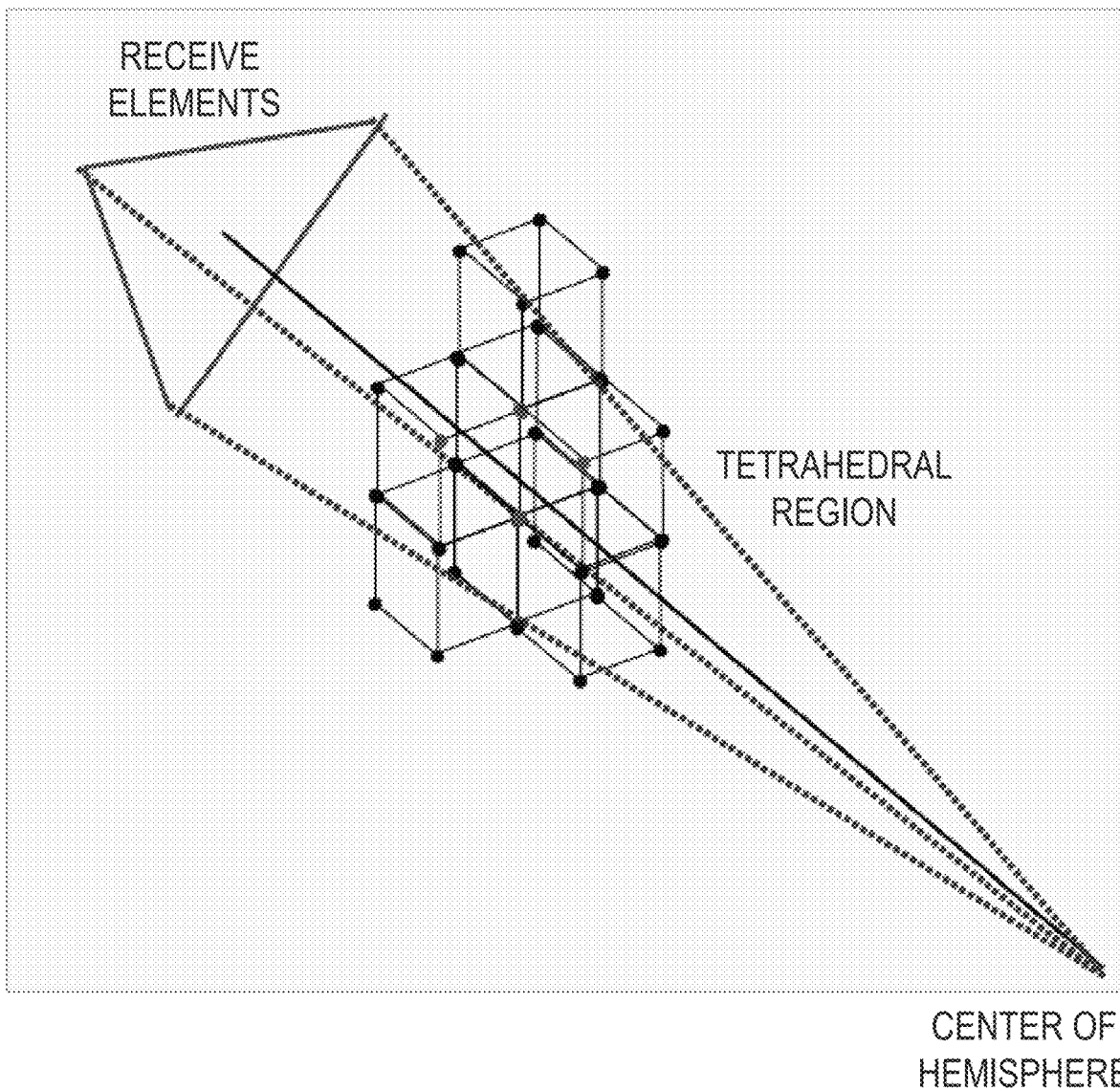
FIG. 13 is a diagram of a tetrahedral region associated with a subtriangle of the hemispheric array. Image values are computed at vertices of a set of cubic subvolumes with centers that intersects the tetrahedral subvolume.

Image values are computed as magnitudes of complex envelopes given by Eq. (15). These computations use compensated geometric delays given by Eq. (27) with aberration adjustments that are most appropriate for the imaged location, i.e., adjustments that are estimated from the focus $x_k^A$ that is closest to the image point. However, the image values are not evaluated along scan lines as is usually the case. Instead, the image values are computed at the points where the vertices of a fixed three-dimensional grid intersect the tetrahedron formed by the triangle of receive elements and the center of the hemisphere as shown in FIG. 13. These image values are reported to the head compute node that consolidates the estimated medium variations from all 160 tetrahedral subvolumes into a single three-dimensional array. This arrangement permits rapid reconstruction of a breast volume that can be rendered by standard three-dimensional rendering software.

Segmentation and Assignment of Tissue Properties

The medium variations that are produced by the procedure described above consist of intensities that are similar to the pixel intensities of b-scan images. To obtain an initial approximation of the scattering object these imaged intensities must be translated into the tissue mechanical properties of sound speed and attenuation. Sound speed assignments are more critical because variations in sound speed determine the phase distortion of the fields $\tilde{\psi}_n(x)$ and $\tilde{\psi}_m(x)$.

The first step is to segment the intensity variations into regions with similar amplitude and speckle characteristics. The methods used for this segmentation can be tailored to the specific characteristics of the imaged intensities, as would be understood by a person skilled in the art. Further, the methods can be based on methods developed for segmenting MRI images of breast tissue that are currently known in the art. For example, a comparison of temporal and spectral scattering methods using acoustically large breast models derived from magnetic resonance images is provided in Hesford et al., 2014, J. Acoust. Soc. Am., 136(2). The segmentation may yield a decomposition of the medium into a small number (e.g., 10 to 20) of disjoint regions $\Re_i, \Re_j, \ldots$. These regions are assumed to represent tissues that have the unknown sound speeds $c_1, c_2, \ldots$.

To estimate the unknown sound speeds, let $\ell_n(x_k^A)=\|x_k^A-x_n\|$, denote the length of the line segment from transducer element n to $x_k^A$, where $x_k^A$ is one of the aberration focal points along the ray from the center of triangle A to the center of the hemisphere. Also, let $\ell_n^{(i)}(x_k^A)$ denote the length of the portion of this line segment that belongs to $\Re_i$. Then, geometric optics approximations give the linear equation $$\sum_{i=1,2,\ldots} \ell_n^{(i)}(x_k^A)c_i^{-1} = \ell_n^{(i)}(x_k^A)c_0^{-1} + \tilde{\varepsilon}_n(x_k^A) \qquad \text{Eq. (28)}$$

in the unknown variables $c_1^{-1}, c_2^{-1}, \ldots$. Application of Eq. (28) to each time shift estimate $\tilde{\varepsilon}_n(x_k^A)$ results in an overdetermined system of linear equations in the unknown variables $c_1^{-1}, c_2^{-1}, \ldots$ that has a unique least-square-error solution. Attenuation factors for the initial approximation are much less important and may be derived from tissue type identifications determined from the sound speeds.

The methods described above differ from conventional imaging in several respects. For example, b-scan images are usually formed by synthetic focusing of the received signals along a scan line (or at least a segment of a scan line) that is aligned with one axis of the image. This use of an extended focus reduces the amount of computation at the expense of lateral resolution. The resolution realized by the HABIS algorithm is better because separate transmit and receive focuses are formed at each voxel. Efficiency is realized in the HABIS algorithm by imaging tetrahedral subvolumes in parallel. They also differ in the scheme for using progressive compensations that are based on estimates from focal points of increasing depth. They further differ in the specialized geometry of the estimation procedure that uses one central subtriangle of receive elements and four subtriangles of transmit elements that include and surround the subtriangle of receive elements. They also differ in the partitioning of the reconstruction into tetrahedral subvolumes, and they further differ in the procedures used to segment and assign tissue mechanical properties to the image intensities.

Wide-Angle and Perturbation Formulations of Split-Step Computations

Propagation of monochromatic fields through the approximate scattering object is a time consuming computation that is required by the reconstruction procedure. Multipole or k-space methods may be used to obtain these fields, but these algorithms are too computationally costly to propagate fields from all 10,240 transducer elements. The split-step algorithm is able to perform these propagations more efficiently. Split-step methods separate monochromatic waves into components that travel in forward and backward directions with respect to a distinguished z axis. If the backward traveling components are ignored, then the propagation can proceed in steps that derive field values on successive x-y planes from the field values on preceding planes. However, exact forward propagators for these steps are nonlinear combinations of spatial and frequency domain operators that do not commute. For efficient computation, these propagators must be approximated by alternating sequences of operators that act in the spatial domain and the spatial-frequency domain. In the simplest cases, the propagators are approximated as a product of a single spatial-domain operator and a single frequency-domain operator. However, these propagators are only accurate when the propagated fields are limited to spatial frequencies with small transverse components. Better approximations that include additional terms are often called wide-angle approximations because they are applicable to fields that have spatial frequencies with larger transverse components.

Two adaptations for improving the accuracy of split-step computations are described herein:

1. Wide-angle correction: Exact forward propagators are exponential operators of the form $\exp[jk_0\Delta z(\sqrt{1+P+Q}-1)]$, where Q is a multiplication operator in spatial coordinates and P is a multiplication operator in spatial-frequency coordinates. If the P and Q operators only produce small variations, then a first-order binomial expansion of the radical can be used to obtain the approximate propagator $\exp[jk_0\Delta z(P+Q)/2]$. Further approximation of the exponential gives either $\exp(jk_0\Delta zP/2)\exp(jk_0\Delta zQ/2)$ or $\exp(jk_0\Delta zQ/2)\exp(jk_0\Delta zP/2)$. These factored propagators are used in conventional split-step algorithms and, as noted above, are only applicable to fields comprised of spatial frequencies with small transverse components. Wide-angle correction refers to the inclusion of additional terms that extend the accuracy of the approximations to spatial frequencies with larger transverse components.

The increased accuracy realized by any correction term must be weighed against the added computational cost of including the correction. These costs can be conveniently quantified by counting the number of Fourier transforms in the computation because the other operations are usually much less expensive than the Fourier transforms. The cost of simple, i.e., narrow-angle, split-step propagation is a single pair of Fourier transforms, and wide-angle correction terms generally require at least one additional pair of transforms. Thus, propagations that employ wide-angle correction require at least twice as much computation as the narrow-angle algorithm. The high computational cost of wide-angle correction implies that the benefit from the correction should be optimized. A term has been developed that is more accurate than the known published correction terms of comparable cost. The term is given by:

$$\phi(x,0) \to \phi(x,0) + jk_0\Delta z\binom{1/2}{2}^{-1}\left(\frac{\sqrt{1+P}-\frac{P}{2}-1}{P}\frac{\sqrt{1+Q}-\frac{Q}{2}-1}{Q} + \frac{\sqrt{1+Q}-\frac{Q}{2}-1}{Q}\frac{\sqrt{1+P}-\frac{P}{2}-1}{P}\right)\phi(x,0).$$

2. Split-step perturbations: In addition to wide-angle correction, a perturbation form of the split-step algorithm can be derived that gives substantially more accuracy than simple split-step propagation without requiring any additional FFTs. Although the method may not be as accurate as propagations that include the wide-angle correction, much better results than narrow-angle propagators can be obtained with essentially no additional cost.

Scattering Measurements

Another computation that the HABIS reconstruction procedure requires is the evaluation of the scattering measurements $\tilde{M}_{mn}$ that are due to the approximate scattering object. These measurements are deducted from the actual scattering measurements $M_{mn}$ to obtain the residual measurements $M_{mn}-\tilde{M}_{mn}$ that are used to determine the refinement $\Delta\eta(x)$. The scattering measurement $\tilde{M}_{mn}$ is expressed by the volume integral $$\tilde{M}_{mn}=\int\eta(x)\tilde{\psi}_m(x)\psi_n(x)d^3x, \quad \text{Eq. (29)}$$

where $\tilde{\psi}_m(x)$ is the transmit field from transducer element m that propagates through the approximate scattering object, $\psi_n(x)$ is the receive sensitivity pattern of transducer element n that propagates homogeneously, and $\eta(x)$ denotes the medium variations of the approximate scattering object. Evaluation of the volume integral in Eq. (29) is costly because the integration has to be repeated for all 10,240× 10,240 combinations of transmit and receive elements.

A much more efficient method for evaluating Eq. (29) has been developed. The method is based on: 1) Expression of the integral in the spatial-frequency domain; 2) Expansion of the Fourier transform of $\psi_n(x)$ as an angular spectrum to reduce the three-dimensional spatial-frequency integral to a surface integral over a sphere of spatial frequencies; 3) Interpolation of spatial-frequency components on the sphere to values on hemispheres that are parameterized by two-dimensional grids with the same planar orientations as the facets; 4) Evaluation of scattering measurements on two-dimensional spatial grids that each contain one of the array facets by taking the inverse two-dimensional Fourier transforms of the spatial-frequency arrays obtained in Step 3; and 5) Interpolation of the values on regular arrays of scattering measurements to obtain the values of scattering measurements at the locations of the pseudo-random distribution of element positions.

The improvement in efficiency over direct evaluation of Eq. (29) is several orders of magnitude. However, very accurate methods of interpolation are required.

Fast Rotation Algorithm

To incorporate the approximate scattering object in a split-step propagation of the field of a transducer element, the array of medium variations that prescribe the scattering object must be rotated so that one dimension of the array is aligned with the element axis. Thus, in the course of a complete reconstruction, the medium variations must be rotated to 40 different orientations that are determined by the 40 facets of the hemispheric array (because the facet normal is the propagation axis of every element in a facet). The split-step propagations produce three-dimensional arrays of field values at the same grid locations as the rotated medium variations, and these arrays must be further rotated to a single common orientation to facilitate subsequent computations. Since the dimensions of all these three-dimensional arrays are large (~1,500×1,500×1,500) the rotations are costly. In fact, the rotations are generally more time consuming than all the other computations. For this reason, a very fast three-dimensional rotation algorithm was developed that is tailored to GPU computation.

GPU algorithms are most efficient when memory accesses are coalesced and are transferred to and from global memory as infrequently as possible. To minimize the cost of global memory transfer, the algorithm can factor three-dimensional rotations into a series of skew operations that interpolate shifted values along one of the three dimensions of the array. Such a rotation algorithm can be several times faster than conventional algorithms rotations, and can also provide increased precision more efficiently than conventional algorithms. Further description of such rotation algorithms as contemplated herein are provided in Appendix A.

Fast and Accurate Harmonic Interpolation

The algorithm for computing scattering measurements and the algorithm for rotating three-dimensional arrays described above both require interpolation of a set of data values at the vertices of a regularly sampled grid. A large number of interpolated values are generally required. However, in some cases the interpolated locations are spaced irregularly, while in other cases they occur at regular intervals, e.g., at the midpoints of the sample intervals in the original array.

Since each interpolated value is computed as a linear combination of sample values in the original array, the computational cost of each interpolation is roughly proportional to the number of original sample values that take part in the interpolation. For example, a two-dimensional interpolation that employs values in a 4×4 subarray is four times as expensive as a two-dimensional interpolation that only employs values in a 2×2 subarray. Thus, to improve efficiency the size of the subarray of original values that contribute to each interpolation should be minimized. On the other hand, interpolations that employ smaller subarrays of original values are less accurate than interpolations that employ larger subarrays of original.

In one embodiment, the accuracy of interpolations that are obtained from small subarrays can be increased by optimizing the interpolation coefficients for a revised array of sample values that are obtained by a prefiltering operation. The improvement in precision realized by this technique is significant. Further, in the scattering measurement computations, the prefiltering step can be incorporated in prior computations at a very low cost. In another embodiment, the accuracy of finite-length interpolations can be increased by optimizing the interpolation coefficients with respect to a non-standard target frequency response. This scheme is ideally suited to the skew operations of the rotation algorithm. Further description of such interpolations as contemplated herein is provided in Appendix B.

Each of the algorithmic improvements described herein contribute to the performance of the HABIS reconstruction procedure. However, these improvements also all have applications in other areas. For example, split-step propagations can be used to model waves of all forms, e.g., electromagnetic, seismic, ultrasonic, etc. Similarly, the efficient form of the scattering computation can also be applied to such cases. The interpolation and volume rotation algorithms also have wide ranging applications that are completely independent of the reconstruction algorithm, as would be understood by a person skilled in the art.

Noise Reduction

Image reconstruction by HABIS is based on the scattering measurement representations given by Eq. (2) and Eq. (10). Any contributions to the scattering measurements that are not included in these representations can degrade image resolution, and may be considered noise. These contributions include conventional forms of noise such as thermal noise, crosstalk, and jitter that originate in the electronics as well as include other terms that are correctly measured responses to effects for which Eq. (2) and Eq. (10) do not account. Examples of this latter form of noise are patient movement and inaccuracy in the split-step propagations of the transmitted fields. An important aspect of the HABIS design is anticipating sources of noise and finding ways to minimize the image-degrading effects of these terms. Reconstruction of high-quality images can be difficult or impossible without the noise reduction compensations described below.

Transmission Encoding

Thermal noise from receive circuitry is inescapable. However, the effect that this noise has on image reconstruction can be diminished if the amplitudes of the received signals can be increased without increasing the noise. One way to do this is to increase the amplitude of the transmitted signals. However, practical considerations limit driving small transducer elements with high-voltage signals. Furthermore, high-amplitude ultrasound waves propagate nonlinearly and produce undesirable nonlinear responses. In conventional pulse-echo ultrasound imaging systems, reflections are amplified by transmitting ultrasound waves simultaneously from many elements that are usually concentrated by focusing in regions of interest. However, this yields a smaller set of scattering measurements that have less coherent resolution than the complete set of 10,240×10,240 element-to-element responses in the described imaging system. The signal-to-noise ratios of HABIS scattering measurements are improved by a different method. A total of 10,240 transmissions are used in each scan. Each of these transmissions is a coded combinations of signals from 2,048 transmit elements. The same basic pulse shape is transmitted from all of the 2,048 elements that participate in a given transmission. The sign of the pulse is inverted for a subset of the elements. The subset of negated pulses changes from transmission to transmission according to a scheme that allows the received signals to be added and subtracted in combinations that isolate the responses to transmissions from each of the individual elements. The purpose of this encoding and decoding of the element-to-element responses is to increase the signal-to-noise ratio of the received signals. Special system characteristics have to be satisfied for this encoding to be effective because the encoding is highly sensitive to crosstalk and jitter between samples of received signals from different receive elements. Meeting the reduced tolerances for jitter and crosstalk required specially designed electronic circuitry.

Two-Second Illumination

Imaging systems that use transducer probes or small two-dimensional arrays of transducer elements that must be translated or rotated or both to acquire scattering from different orientations have relatively long scan times that introduce measurement error caused by tissue movement. To minimize error from tissue movement, the HABIS scanning procedure was designed to collect a complete scan of 10,240 receive signals from each of 10,240 transmissions within a time span of about two seconds. This is essentially the smallest possible scan time for this set of transmissions because two seconds is about equal to the time required for 10,240 ultrasound transmissions to make round trip excursions through an average size breast. Numerous design challenges were met to accomplish this rapid acquisition. Signals from all 10,240 receivers had to be acquired simultaneously, so the receive channels could not be multiplexed. Thus, a separate data-acquisition channel was needed for each receiver. Furthermore, since each complete scan is comprised of nearly a terabyte (TB) of data, the system must include local memories to retain the acquired data as well as a high-speed data transfer system to transmit the acquired data to the high-performance computer network in a timely manner. Currently available ultrasound imaging systems employ far fewer channels and do not handle data sets of this size.

Time Gates that Eliminate Noise from Remote Scattering

All ultrasound imaging systems reconstruct medium variations by dividing the reflected signals into contributions that come from different regions. The HABIS inverse scattering algorithm is a coherent imaging method that resolves locations in the scattering object by forming linear combinations of residual scattering measurements that coherently sum the contributions that come from one location while incoherently summing the contributions that come from all other locations. This imaging technique has higher point resolution than conventional algorithms, but can have reduced contrast resolution when the incoherent sums are appreciable. Thus, incoherently summed scattering from distant reflectors is a form of noise that can degrade image quality. To reduce this degradation, receive time gates are used, prior to reconstruction, to isolate the scattering measurements that originate from different regions. The noise reduction strategy used in HABIS is not readily applicable to other inverse scattering algorithms that perform reconstructions globally. However, time gates can be conveniently included in the HABIS reconstruction algorithm because HABIS reconstructions are partitioned into a large number of subvolumes.

Calibration that Eliminates Variations in System Responses

Representation of the medium variations by Eq. (2) can only be as accurate as the estimates $\tilde{\psi}_m(x)$ and $\tilde{\psi}_n(x)$ of transmit fields and receiver sensitivity patterns that appear in the integrand of Eq. (2). These fields are computed by using the split-step algorithm to propagate fields from the element locations $x_m$ and $x_n$ through the approximate scattering object. Thus, any error in an element location can translate into phase error throughout the entire field. For this reason, accurate determination of the element positions is needed. Since minor variations in manufacturing can introduce small offsets in effective element positions, a calibration scheme was developed to determine the element positions from scans of a specially constructed calibration fixture. These scans are also used to equalize characteristics of all the elements in the hemispheric array. This equalization compensates for variations in element sensitivity and also element-to-element variation in the electro-acoustic frequency responses.

Use of Matching Fluids

The accuracy of the field estimates $\tilde{\psi}_m(x)$ and $\tilde{\psi}_n(x)$ also depend on the accuracy of the split-step algorithm. Split-step propagations lose precision when the medium variations cause strong refraction of propagated fields, and the accumulated error that results from this refraction can be especially large when the refraction occurs in the early stages of the transmission. The interface between breast tissue and the ambient fluid is always encountered at the beginning of each transmission, and causes strong refraction when the ambient fluid is water because of the difference between the speed of sound in water and the speed of sound in tissue. For this reason, an ambient fluid other than water is desirable to minimize refraction at the breast surface.

Estimation of Scattering Object Detail in the Antipodal Hemisphere

The hemispheric array breast imaging system (HABIS) includes features that provide advantages over currently available ultrasound imaging systems, including b-scan instruments and systems that employ other forms of inverse scattering. One feature is the measurement of scattering throughout a hemisphere surrounded by an array of ultrasound transducers. In one embodiment, another feature is the use of scattering measured in the hemisphere surrounded by the array to estimate scattering object detail that would come from scattering in the antipodal hemisphere, where measurements of scattering cannot be made directly.

As described herein, the HABIS reconstruction algorithm uses scattering measured throughout an entire hemisphere surrounded by the transducer array to form an estimate of the scattering object. Additionally, the HABIS reconstruction algorithm extrapolates from the measurement hemisphere spatial frequencies that correspond to scattering in the antipodal hemisphere to obtain information equivalent to that obtained from measurement of scattering in that hemisphere. In other words, the HABIS algorithm uses scattering measured in a solid angle of $2\pi$ steradians (i.e., throughout a hemisphere encompassed by the transducer array), and uses spectral extrapolation to obtain information from scattering that cannot be measured in the antipodal hemisphere directly (i.e., throughout the antipodal solid angle of $2\pi$ steradians corresponding to the other hemisphere). The result is that spatial frequencies spanning an entire lowpass volume in the Fourier transform of the image space, a transform space known as wave space, are used by the HABIS image reconstruction algorithm to obtain the maximum theoretical amount of spatial detail contained in that volume.

Accordingly, the use of all the scattering object detail in a lowpass volume of the scattering object transform space in the HABIS reconstruction algorithm provides an advantage over other ultrasound imaging methods that only measure scattering in a plane (and so ignore out-of-plane scattering), or that only measure scattering over a relatively narrow solid angle in the forward direction (and so ignore scattering in most of the total $4\pi$-steradian solid angle). These other methods do not obtain or use all of the measurable scattering object information. Therefore, the other methods are incapable of imaging detail associated with scattering throughout an entire solid angle of $4\pi$ steradians.

Another advantageous feature of HABIS is the short data-acquisition time. For example, in one embodiment, the data-acquisition time is about two seconds. This data-acquisition time, which is very much shorter than in systems that rotate or otherwise move transducers to acquire data, practically eliminates motion-induced degradation of the reconstructed volume. Yet another advantage of HABIS is point resolution that is both high and isotropic. The point resolution of HABIS is essentially equal to the lateral resolution in high-quality x-ray mammograms in which image features are typically blurred by summation of x-ray absorption along the direction of the projection.

Illustration of HABIS Imaging Capabilities

Reconstructions based on inverse scattering and corresponding b-scan images have been obtained using calculated scattering by a 10-point resolution target, and by a realistic breast model derived from 200-am resolution MRI data to illustrate the resolution and fidelity of the volumetric images produced by HABIS. Each of the inverse-scattering reconstructions used scattering at the surface of the entire hemispheric transducer array, and also used an estimation of scattering object detail that would come from measurements in the opposite hemisphere where scattering cannot be directly measured. This approach obtains spatial frequencies spanning an entire lowpass volume in the Fourier transform of the image space (a transform space known as wave space) to realize the maximum theoretical amount of spatial detail contained in that volume. Each of the b-scans used transmission from a 64-element subtriangle and three 64-element subtriangles surrounding that central subtriangle, and used reception from the central 64 element subtriangle. Use of these transmit and receive apertures takes advantage of the system architecture to allow formation of a volumetric b-scan in about one minute after a two-second interval of data collection. This b-scan has sufficient resolution to assess the quality of the acquired data for a more time-consuming volumetric reconstruction based on inverse scattering.

Figure 14:
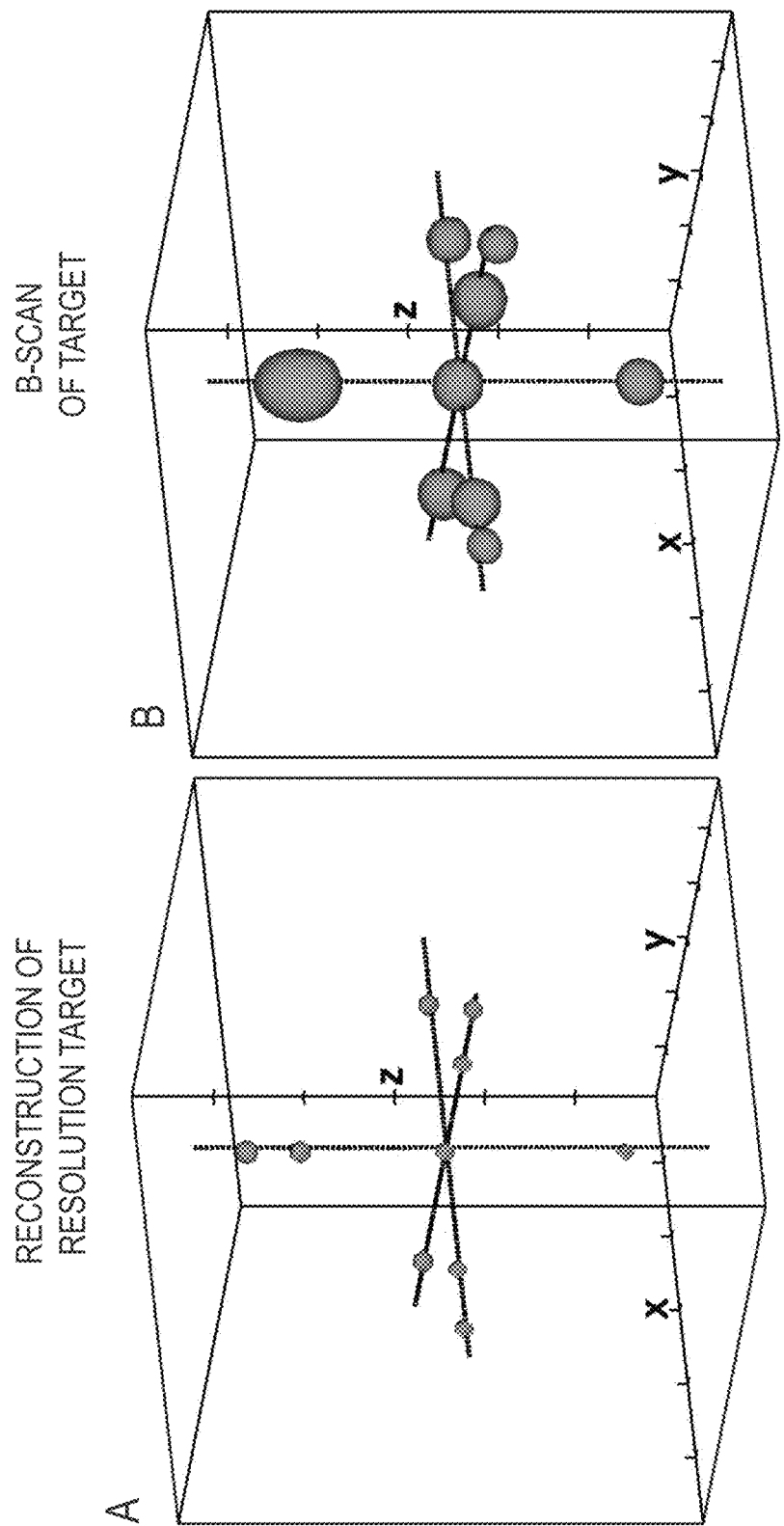
FIG. 14, comprising

Representative images of the resolution target are shown in FIG. 14. At the 5-MHz frequency used to obtain FIG. 14A, the Rayleigh-defined resolution inferred from inverse-scattering reconstructed data is 100 µm. For the location of the resolution target in the b-scan shown in FIG. 14B, the transmit f-number was about 1.5 and the receive f-number was about 2.9. The pulse spectrum used for the b-scan had a raised-cosine shape centered around 5 MHz with a −6-dB bandwidth of 2 MHz. These transmit-receive apertures and pulse bandwidth yield an isotropic Rayleigh-defined resolution of about 700 µm. A b-scan using transmission and reception throughout the hemisphere would have a lateral resolution comparable to the resolution in the reconstruction as a result of the transmit and receive effective f-numbers each being one half.

Figure 15:
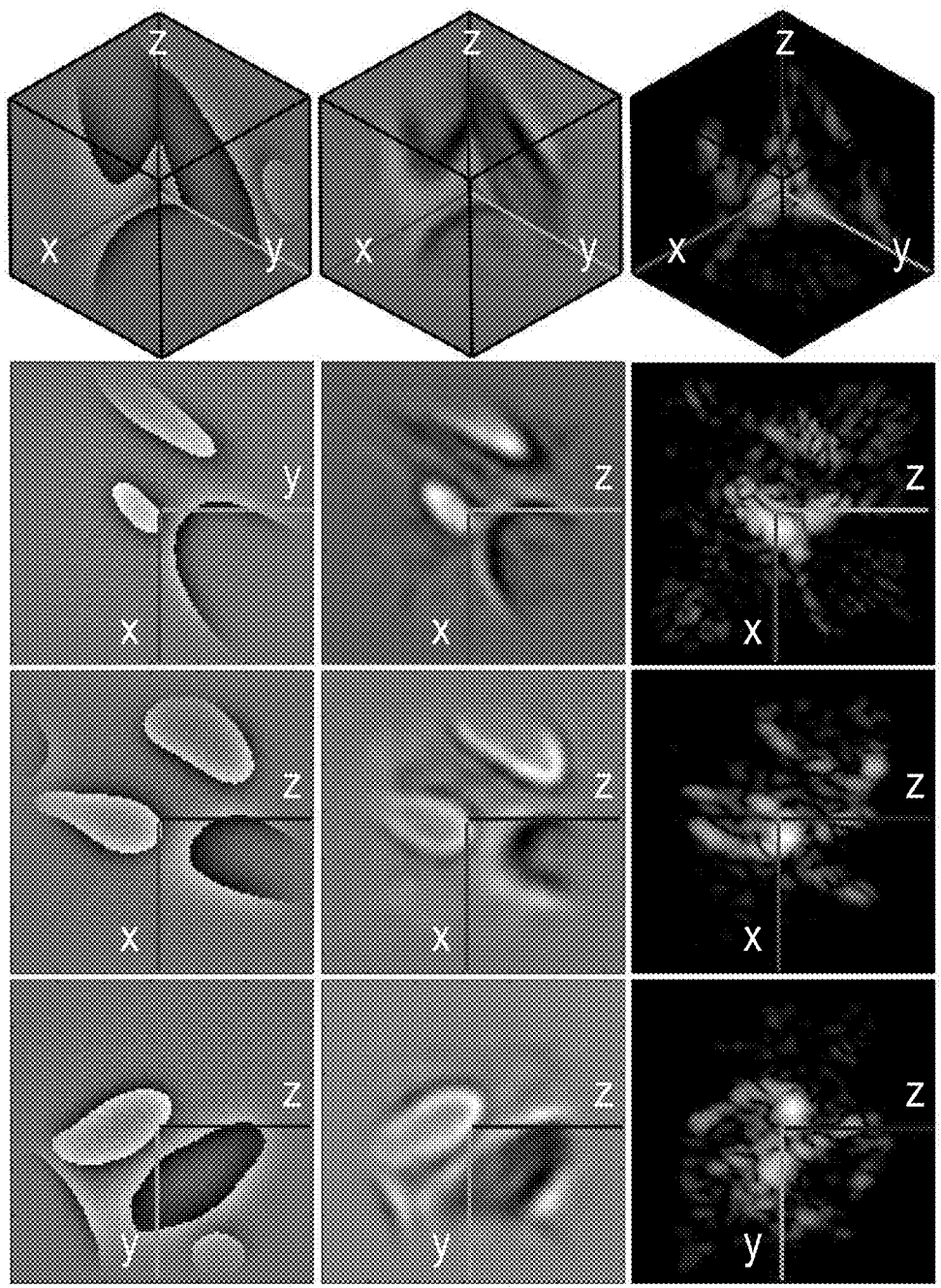
FIG. 15 is a set of images showing sections of a representative subvolume in a model of the breast. Columns left to right: Sections in the original subvolume, corresponding sections in the inverse-scattering reconstruction of the subvolume, and corresponding sections in the aberration-corrected b-scan of the subvolume. Rows top to bottom.

Representative sections of a 6.4-mm3 subvolume in the breast model are shown in FIG. 15. The reconstruction was performed at a frequency of 5 MHz as in the case of the resolution target. The detail evident in the reconstructed-image panel of FIG. 15 comes from the use of scattering throughout the entire surface of the hemispheric array. This scattering was first used to estimate scattering measurements that would be made by a virtual array in the opposite hemisphere and then the combined set of data was used in the reconstruction. The b-scan used aberration correction. For the location of the subvolume of the model, the transmit f-number in the b-scan was about 3.0 and the receive f-number in the b-scan was about 6.0. These transmit-receive apertures yield a Rayleigh-defined lateral resolution of about 1.5 mm at the 5-MHz center frequency. The pulse spectrum was the same as used for the resolution target so the axial resolution is about 700 m as in the case of the resolution target. The inverse-scattering reconstruction clearly shows the subvolume morphology with high fidelity while the b-scan mainly highlights discontinuities that are approximately perpendicular to the b-scan lines.

Rotation in Two Dimensions

Let $u_1$, $u_2$ be the pair of generating vectors used to step between vertices of a Cartesian grid v (n, m). Thus, $$v(n,m) = nu_1 + mu_2 : n, m = 0, \pm 1, \pm 2, \ldots \quad (1)$$

The vectors $u_1$ and $u_2$ are assumed to be orthogonal, but are not assumed to be of equal length. A rotated grid of vertices $$\tilde{v}(n,m) = n\tilde{u}_1 + m\tilde{u}_2 : n, m = 0, \pm 1, \pm 2, \ldots \quad (2)$$

can be formed by replacing $u_1$ and $u_2$ in Eq. (1) with counterclockwise rotations $\tilde{u}_1 = R_\theta[u_1]$ and $\tilde{u}_2 = R_\theta[u_2]$ of $u_1$ and $u_2$ where θ is the angle of rotation.

Let Q[n, m] be an array of sample values of a smooth function q x, y) at the vertices v(n, m). An efficient interpolation scheme is developed below for generating sample values $\tilde{Q}$[n, m] of q(x, y) at the rotated vertices $\tilde{v}$(n, m). The sample values at the vertices of the rotated grid are obtained from three interpolations that each generate sample values at the vertices of a new grid that is skewed relative to the vertices of the previous grid. The skewing operation is illustrated in FIG. 16. The black dots in the figure are the vertices of the original grid, and the red dots are the vertices of the skewed grid. Notice that both grids have the same vertical lines. However, the red lines that connect vertices in the non-vertical dimension are not horizontal. The vertices of the skewed grid in FIG. 16 can be represented by $$v'(n,m) = nu'_1 + mu'_2 : n, m = 0, \pm 1, \pm 2, \ldots, \quad (3)$$

where $u'_1 = u_1 + \alpha u_2$ and $u'_2 = u_2$.

Function values at the vertices of the skewed grid can be generated from function values at the vertices of the original grid by one-dimensional interpolations along the vertical grid lines. The simplicity and efficiency of these interpolations is the reason that skewing is preferable to direct rotation. A skew can also be applied to the vertical lines rather than horizontal lines. In that case, values at the skewed vertices are obtained from one-dimensional interpolation along horizontal lines in the original grid.

FIG. 17 shows a succession of skew transformations that result in a rotated grid*. The black dots in the figure are the vertices of the original grid and the red dots are the vertices of the grid that results from skewing the horizontal lines of the original grid. A second skewing of the vertical lines in the red grid then results in the grid of green vertices. Finally, skewing the green vertices in the other (roughly horizontal) dimension gives the blue grid that is a rotation of the original black grid. The grid lines associated with the green vertices are not shown because one set of lines in the green grid coincides with lines of the red grid lines, and the other set of lines in the green grid coincide with lines of the blue grid.

*A rotated orthogonal grid can be obtained with two skew transformations rather than three, but the pitches of the grid are distorted by this transformation.

The successive skew transformation shown in FIG. 17 can be expressed as changes in the grid generating vectors as follows:

$$\text{First Skew:} \quad \begin{pmatrix} u_1 \\ u_2 \end{pmatrix} \Rightarrow \begin{pmatrix} u'_1 = u_1 + \alpha u_2 \\ u'_2 = u_2 \end{pmatrix} \quad (4)$$

$$\text{Second Skew:} \quad \begin{pmatrix} u'_1 \\ u'_2 \end{pmatrix} \Rightarrow \begin{pmatrix} u''_1 = u'_1 \\ u''_2 = u'_2 + \beta u'_1 \end{pmatrix}$$

-continued $$\text{Third Skew:} \quad \begin{pmatrix} u_1'' \\ u_2'' \end{pmatrix} \Rightarrow \begin{pmatrix} \tilde{u}_1 = u_1'' + \gamma u_2'' \\ \tilde{u}_2 = u_2'' \end{pmatrix}$$

The geometry used to determine the skews $\delta_1 = \alpha u_2$, $\delta_2 = \beta u'_1$, and $\delta_3 = \gamma u''_2$ is shown in FIG. 18. Similar triangles in the figure imply that $\tilde{u}_1 = u_1$ and $\tilde{u}_2 = u_2$, and also imply that $\tilde{u}_1 = R_\theta[u_1]$ and $\tilde{u}_2 = R_\theta[u_2]$. The identities $$\|\delta_1\| = \|\delta_3\| = \|u_1\|\tan(\theta/2), \quad (5a)$$

$$\|\delta_2\| = 2\|u_2\|\sin(\theta/2), \quad (5b)$$

$$\|u'_1\| = \|u_1\|/\cos(\theta/2), \quad (5c)$$

and $$\|u''_2\| = \|u_2\|. \quad (5d)$$

that are also evident from the figure give $$\alpha = \|\delta_1\|/\|u_2\| = (\|u_1\|/\|u_2\|)\tan(\theta/2), \quad (6a)$$

$$\beta = -\|\delta_2\|/\|u'_1\| = -(\|u_2\|/\|u_1\|)\sin(\theta), \quad (6b)$$

and $$\gamma = \|\delta_3\|/\|u''_2\| = (\|u_1\|/\|u_2\|)\tan(\theta/2). \quad (6c)$$

In particular, if $\|u_1\| = \|u_2\|$, then $\alpha = \gamma = \tan(\theta/2)$ and $\beta = -\sin(\theta)$. Since coordinate rotations are generally applied to isotropic grids, the identity $u_1 = u_2$ is assumed throughout the subsequent discussion.

A step-by-step the procedure for two-dimensional rotation of the sample values Q[n, m] at the vertices of an isotropic grid is given below:

1. For each fixed value n of the first index, the one-dimensional array Q[n, m]:m=0, ±1, ±2, . . . is translated by the fractional offset n tan(θ/2) to obtain the two-dimensional array Q'[n, m]=Q[n, m+n tan(θ/2)]:n, m=0, ±1, ±2, . . . .
2. For each fixed value m of the second index, the one-dimensional array Q'[n, m]n=0, ±1, ±2, . . . is translated by the fractional offset −m tan(θ) to obtain the two-dimensional array Q"[n, m]=Q'[n−m sin(θ), m]:n, m=0, ±1, ±2, . . . .
3. For each fixed value n of the first index, the one-dimensional array Q"[n, m]:m=0, ±1, ±2, . . . is translated by the fractional offset n tan(θ/2) to obtain the rotated two-dimensional array $\tilde{Q}$[n, m]=Q"[n, m+n tan(θ/2)]:n, m=0, ±1, ±2, . . . .

A procedure for one-dimensional translation must also be specified. Exact band-limited translation can be achieved by means of harmonic interpolation, but convolution with a shifted and modified sine function can give accurate results with less computation. The accuracy of these interpolations is determined by the length of the convolution filters. If the translations are performed with convolution filters of length L, then the computational cost of the entire rotation is $$\underbrace{3}_{\text{\# of skews}} \times \underbrace{L}_{\text{Mult and adds}} \times \underbrace{2}_{\times, +} \times \underbrace{N}_{\text{\# of values}} = 6LN \text{ flops}. \quad (7)$$

Angle Reduction and Array Dimension Requirements

The procedure described in the previous section factors two-dimensional coordinate rotations into three skew transformations. However, the factorization does not consider possible limitations imposed by the finite dimensions of the array. The following additional factorizations are noted before addressing this issue:

1. If $\tilde{u}_1 = R_\pi[u_1]$ and $\tilde{u}_2 = R_\pi[u_2]$, then $\tilde{u}_1 = -u_1$, $\tilde{u}_2 = -u_2$ and, consequently, $\tilde{Q}[n, m] = Q[-n, -m]$:n, m=0, ±1, ±2, . . . .
2. If $\tilde{u}_1 = R_{\pi/2}[u_1]$ and $\tilde{u}_2 = R_{\pi/2}[u_2]$, then $\tilde{u}_1 = -u_2$, $\tilde{u}_2 = u_1$ and, consequently, $\tilde{Q}[n, m] = Q[-m, n]$:n, m=0, ±1, ±2, . . . .

Thus, reflection and transposition can be used to reduce any rotation to a rotation that is limited to the range $|\theta| \leq \pi/4$.

Let $[n_0, m_0]$ be the indices of a particular value in the original array. A rotation of the coordinates will result in a reassignment of this value to new coordinates $[\tilde{n}_0, \tilde{m}_0]$, and if these coordinates are not contained within the dimensions of the array then the value must be discarded. The array dimensions must, therefore, be large enough to include both the initial and rotated indices of all the values to be rotated. This is a natural and obvious requirement that is applicable to any in place rotation algorithm. In some cases, factorization of the rotation into skew transformations can require a larger array because values can be translated to intermediate indices that exceed the array dimensions. The translations of $[n_0, m_0]$ that result from the skew transformations can be expressed as $$[n_0, m_0] \rightarrow [n_0, m_0 + n_0 \tan(\theta/2)] \quad (8)$$
$$\rightarrow [\tilde{n}_0, m_0 + n_0 \tan(\theta/2)]$$
$$\rightarrow [\tilde{n}_0, \tilde{m}_0],$$

where $[\tilde{n}_0, \tilde{m}_0]$ are the final rotated indices. This equation implies that successful transfer of the array value with indices $[n_0, m_0]$ to the rotated indices $[\tilde{n}_0, \tilde{m}_0]$ requires both $n_0$ and $\tilde{n}_0$ to be in the range of the first array index, and also requires $m_0$, $\tilde{m}_0$ and $m_0 + n_0 \tan(\theta/2)$ to be in the range of the second array index. These requirements are illustrated in FIG. 19. The red dotted curve in the figure is the image of the unit circle after application of the first skew transformation for a π/4 rotation. The green dotted curve is the image of the red dotted line after application of the second skew operation for the same rotation. All indices inside the unit circle are mapped to points inside the red dotted curve by the first skew transformation, and are then mapped to points inside the green dotted curve by the second skew transformation. The red, green and blue arrows in the figure show the succession of all three skew transformations at a few selected points.

Successful rotation of all points inside the unit circle requires an array with padding in the second (i.e., vertical) dimension to accommodate the skew transformations that bridge the top and bottom caps of the circle[†]. The exact scale factor for the array expansion is sec (π/8)=1.0824 at both ends. However, if the initial data values only span the upper hemisphere then padding is only needed at the top of the hemisphere. This is also illustrated in the figure by the dotted blue rectangle which outlines the array of data values needed for a π/4 rotation of the upper hemisphere.

[†]Additional space is needed in the vertical rather than horizontal direction because the skew operations are not symmetric. An alternate implementation of the rotation that exchanges the first and second dimensions in the skew transformations would require additional space in the horizontal rather than vertical direction.

The original, red dotted, and green dotted circles could also be used to limit the ranges of the interpolations in the three skew operations. However, the additional logic needed to impose these limits will diminish efficiencies realized from reduced computation.

Rotation in Three Dimensions

Let $u_1$, $u_2$, and $u_3$ be the generating vectors used to step between vertices of the Cartesian grid v (n, m, o) so that $$v(n,m,o) = nu_1 + mu_2 + ou_3 : n, m, o = 0, \pm 1, \pm 2, \ldots \quad (9)$$

Assume the vectors $u_1$, $u_2$, and $u_3$ are orthogonal and of equal length. Then, a rotated grid of vertices $$\tilde{v}(n,m,o) = n\tilde{u}_1 + m\tilde{u}_2 + o\tilde{u}_2 : n, m, o = 0, \pm 1, \pm 2, \ldots \quad (10)$$

can be formed by replacing $u_1$, $u_2$, and $u_3$ in Eq. (9) with the rotated vectors $\tilde{u}_1 = R_{\phi,\theta,\psi}[u_1]$, $\tilde{u}_2 = R_{\phi,\theta,\psi}[u_2]$, and $\tilde{u}_3 = R_{\phi,\theta,\psi}[u_3]$, where $\phi$, $\theta$, and $\psi$ are Euler angles that uniquely determine the appropriate rotation. Euler rotations factor into the product $R_{\phi,\theta,\psi} = R_\psi^3 R_\theta^2 R_\phi^3$ of three two-dimensional rotations where $R_3^k$ denotes a counterclockwise rotation around the k axis through the angle ∂. However, in many applications, less general rotations are sufficient. For example, rotations that orient tissue models for split-step propagation only need to satisfy the condition $$\tilde{u}_3 = R_{\phi,\theta,\psi}[u_3] = -n, \quad (11)$$

where n is a unit vector that points in the direction of forward propagation. If spherical coordinates‡ $\phi$ and $\theta$ specify n as ‡ The azimuth angle $\phi$ used in these coordinates is measured relative to the $u_2$ axis rather than the $u_1$ axis and, consequently, the axis of the polar angle rotation $R_{-\theta}^1$ is $\tilde{u}_1$ rather than $\tilde{u}_2$.

$$-n = \sin \theta \sin \phi u_1 + \sin \theta \cos \phi u_2 + \cos \theta u_3, \quad (12)$$

then Eq. (11) is satisfied by the rotation $R_{-\theta}^1 R_\phi^3$, as illustrated in FIG. 5. To implement this rotation, the step-by-step procedure for two-dimensional rotation given earlier is supplemented with additional skew transformations as follows:

1. For each pair of fixed values n, o of the first and third indices, the one-dimensional array Q[n,m,o]:m=0, ±1, ±2, ... is translated by the fractional offset n tan($\phi$/2) to obtain the three-dimensional array Q'[n, m, o]=Q[n, m+n tan($\phi$/2), o]:n, m, o=0, ±1, ±2, ....
2. For each pair of fixed values m and o of the second and third indices, the one-dimensional array Q'[n, m, o]:n=0, ±1, ±2, ... is translated by the fractional offset −m sin($\phi$) to obtain the two-dimensional array Q''[n, m, o]=Q'[n−m sin($\phi$), m, o]:n, m, o=0, ±1, ±2, ....
3. For each pair of fixed values n, o of the first and third indices, the one-dimensional array Q''[n, m, o]: m=0, ±1, ±2, ... is translated by the fractional offset n tan($\phi$/2) to obtain the rotated three-dimensional array Q'''[n, m, o]=Q''[n, m+n tan($\phi$/2), o]:n, m, o=0, ±1, ±2, ....
4. For each pair of fixed values n, o of the first and third indices, the one-dimensional array Q'''[n, m, o]:m=0, ±1, ±2, ... is translated by the fractional offset o tan($\theta$/2) to obtain the rotated three-dimensional array Q^{iv}[n, m, o]=Q'''[n, m+o tan($\theta$/2), o]:n, m, o=0, ±1, ±2, ....
5. For each pair of fixed values n, m of the first and second indices, the one-dimensional array Q^{iv}[n, m, o]:o=0, ±1, ±2, ... is translated by the fractional offset −m sin($\theta$) to obtain the two-dimensional array Q^v[n, m, o]=Q^{iv}[n, m, o−m sin($\theta$)]:n, m, o=0, ±1, ±2, ....
6. For each pair of fixed values n, o of the first and third indices, the one-dimensional array Q^v[n, m, o]:m=0, ±1, ±2, ... is translated by the fractional offset o tan($\theta$/2) to obtain the rotated three-dimensional array Q^{vi}[n, m, o]=Q^v[n, m+o tan($\theta$/2), o]:n, m, o=0, ±1, ±2, ....

Each of these six steps is a skew transformation that is comprised of one-dimensional transformations along different axes. However, the skews transformations in Step 3 and Step 4 are in the same direction and, therefore, con be consolidated into a single step: 3+4 For each pair of fixed values n, o of the first and third indices, the one-dimensional array Q''[n, m, o]:m=0, ±1, ±2, ... is translated by the fractional offset n tan($\phi$/2)+o tan($\theta$/2) to obtain the rotated three-dimensional array Q^{iv}[n, m, o]=Q''[n, m+n tan($\phi$/2)+o tan($\theta$/2), o]:n, m, o=0, ±1, ±2, ....

This consolidation is the reason for measuring azimuth angle relative to the $u_2$ axis rather than the $u_1$ axis, and also for using a polar angle rotation $R_{-\theta}^1$ with axis $u_1$.

Interpolation Coefficients

High-performance interpolation coefficients for the skew transformations can be determined using methods described in Ref. [1]. However, the prefiltering used in Ref. [1] cannot be efficiently interleaved with the skew transformations and is, therefore, not applicable. Frequency-domain distortion of interpolations for fractional steps ε=0.1, 0.2, 0.3 and 0.4 that use six samples of the sinc function as coefficients are plotted in FIG. 21. These interpolation weights approximate the frequency response $e^{j\varepsilon\omega}$ with minimum least-square error across the entire frequency range $[-\pi, +\pi]$ (in units of radians per unit time-step). The distortion plots in FIG. 21 show the ratio of the approximate response to the ideal response. As $|\omega| \to \pi$ the distortion increases because the approximate responses are periodic but the ideal response is not periodic. The distortion at lower frequencies is exaggerated because coefficients that minimize least-square error across the entire frequency band tend to overemphasize the importance of the large error at high frequencies.

Much better results can be obtained by choosing the coefficients to minimize the least-square error in a reduced range of frequencies. The upper left panel of FIG. 22 shows the distortion that results when six coefficients are chosen to minimize the least-square error in the band $[-0.75\pi, +0.75\pi]$. The distortion of these coefficients is less than 3% in the reduced band. Figures other three panels in FIG. 22 show the further reduction in distortion that results when 8, 10, or 12 coefficients are used instead of 6. These results indicate that skew transformations that are implemented using interpolations with 10 or more coefficients will generate very accurate rotations if the initial data is band-limited to three-quarters of the Nyquist frequency. The operation count for a two-dimensional rotation using 10 coefficient interpolations is 60 floating-point operations per point (Eq. (7)), and the operation count for a three-dimensional rotation using 10 coefficient interpolations is 100 floating-point operations per point. This operation count is comparable to the cost (per point) of a single three-dimensional FFT, and is also comparable to the cost of three-dimensional rotations that interpolate using arrays of 4×4×4=64 coefficients (e.g., bi-cubic interpolation). These interpolation schemes have a computational cost of 128 floating-point operations per point and have substantially more distortion than the 10-point skew transformations.

GPU Implementation of Skew Transformations

The execution time of a skew transformation implemented on a GPU is probably not determined by the operation count. Two other factors that must also be considered are:

1. The time required to upload data to the GPU
2. The time required to access data in GPU memory Both of these operations can run in parallel with the arithmetic operations, and both operations probably require more time than the arithmetic operations. Data transfers to and from the GPU are the most time consuming operations, but the extra time needed for these transfers can be used to perform other parallel computations such as split-step propagations. However, the time spent loading data from GPU memory into registers for a skew transformation can only be parallelized with arithmetic operations for that transformation. Thus, the kernels used to implement the skew transformations should be designed to minimize the number of times that each data value is loaded from memory. A kernel design that only requires each input data value to be loaded once and that also only requires each output value to be stored once is illustrated below.

$$(\text{Input} \to reg0) \Rightarrow \begin{pmatrix} reg1 & = Coeff1 \times reg0 \\ reg2 + & = Coeff2 \times reg0 \\ reg3 + & = Coeff3 \times reg0 \\ reg4 + & = Coeff4 \times reg0 \\ reg5 + & = Coeff5 \times reg0 \\ reg6 + & = Coeff6 \times reg0 \\ reg7 + & = Coeff7 \times reg0 \\ reg8 + & = Coeff8 \times reg0 \\ reg9 + & = Coeff9 \times reg0 \\ reg0 & = Coeff0 \times reg0 \end{pmatrix} \Rightarrow \begin{pmatrix} reg9 \to \text{Ouput} \\ reg8 \to reg9 \\ reg7 \to reg8 \\ reg6 \to reg7 \\ reg5 \to reg6 \\ reg4 \to reg5 \\ reg3 \to reg4 \\ reg2 \to reg3 \\ reg1 \to reg2 \\ reg0 \to reg1 \end{pmatrix}. \quad (13)$$

The function of this kernel is to perform a fractional translation of a one-dimensional array using the 10 coefficient interpolation filter described in the previous section. The registers are initially 0, and the operation described by Eq. (13) is repeated for input values that cyclically traverse the array in either the forward or backward direction, starting at a fixed index $k_0$. The indices of the output values are always a fixed cyclical offset from the indices of the input values. The direction of index progression and the initial index $k_0$ are chosen (based on the size and sign of the translation) to insure that output values do not overwrite valid input values before the input values have been processed. This kernel design is expected to reduce the computational time of each skew transformation to the time required to copy the array inside the GPU.

Dimensions of Rotated Arrays

The tissue parameters must be sampled in a rectangular volume that contains the entire hemisphere and must, therefore, have spatial dimensions of 15 cm×15 cm×7.5 cm. However, the initial estimates of the tissue parameters are not expected to have resolution better than 0.5 mm. The dimensions of the tissue parameter arrays can, therefore, be limited to 300×300×150=13, 500,000 samples. This only requires about 54 megabytes of memory per parameter if the parameter values are single precision floating-point numbers. To implement split-step computations these arrays must be upsampled to arrays of higher density. However, upsampling can take place after the tissue parameters have been rotated to appropriate orientations. Thus, rotation of the tissue model is not a costly computation. Furthermore, each rotated and upsampled tissue model is used for 256 forward computations.

However, rotation of the propagated fields back to a common grid is costly because the field arrays are sampled more finely and every forward solution will require rotation. Some reduction in the cost of these rotations can be realized by only rotating forward field values that belong to the upper hemisphere. The blue dotted rectangles in FIG. 23 show these reductions for propagations from different facet inclinations. The trapezoidal regions in the figure indicate limits of the directivity patterns of elements within the f acet. These ranges can also be used to limit the rotated volumes, but these limits are do not translate into changes in array dimensions and would have to be built into the logic of the skew transformations.

These notes describe a method for accurate and efficient interpolation of a uniformly sampled time series x[n], n=0, ±1, ±2, . . . at fractional indices.

Any form of interpolation requires the time sequence to be composed of samples of a continuously varying signal with values at fractional indices that can be inferred from the sampled values. The signal is usually assumed to be continuous and band limited to frequencies ω with magnitudes that are less than the Nyquist frequency π. In that case, the continuous signal x(t) can be reproduced from the sequence x[n] by $$x(t) = \sum_{n=-\infty}^{\infty} x[n] \frac{\sin(\pi(t-n))}{\pi(t-n)}. \quad (1)$$

Unfortunately, Eq. (1) is not an efficient way to evaluate x(t) because the sine function dies off rather slowly so that a large number of terms are needed to form accurate estimates.

The right side of Eq. (1) is a discrete inner product of the sequence x[n] and the sequence $s_t[n]=\sin(\pi(t-n))/\pi(t-n)$ that may also be evaluated in the frequency domain. Let X(ω): −π≤ω≤π denote the discrete time Fourier transform of x[n] and let $S_t(\omega)$: −π≤ω≤π denote the discrete time Fourier transform of $s_t[n]$ given by $$S_t(\omega) = \sum_{n=-\infty}^{+\infty} \frac{\sin(\pi(t-n))}{\pi(t-n)} e^{-j\omega n} \quad (2)$$

$$= \sum_{n=-\infty}^{+\infty} \frac{1}{2\pi} \int_{-\pi}^{+\pi} e^{-j\omega(t-n)} d\omega$$

$$= e^{-j\omega t} \frac{1}{2\pi} \int_{-\pi}^{+\pi} \left( \sum_{n=-\infty}^{+\infty} e^{j\omega n} \right) d\omega$$

$$= e^{-j\omega t} \frac{1}{2\pi} \int_{-\pi}^{+\pi} 2\pi \delta(\omega) d\omega = e^{-j\omega t}$$

Then, by Parseval's formula, $$x(t) = \frac{1}{2\pi} \int_{-\pi}^{+\pi} X(\omega) S_t(\omega) d\omega = \frac{1}{2\pi} \int_{-\pi}^{+\pi} X(\omega) e^{-j\omega t} d\omega. \quad (3)$$

Equations (1) and (3) are time-domain and frequency-domain expressions of harmonic interpolation that, as noted above, is exact when the sample sequence is not aliased. Using the inverse FFT algorithm to evaluate Eq. (3) is an efficient way to interpolate values at many locations that are all offset by the same amount from the nearest sample. However, Eq. (3) is not an efficient alternative to Eq. (1) if the spacing of the interpolated samples is irregular.

Efficient interpolation schemes generally estimate x(t) as a linear combination of a few of the sample values that are nearest to t. For example, if $0 \leq \varepsilon \leq 0.5$, then a four-point interpolation of $x(\varepsilon)$ has the form $$x(\varepsilon) \approx w_{-1}(\varepsilon)x[-1]+w_0(\varepsilon)x[0]+w_1(\varepsilon)x[1]+w_2(\varepsilon)x[2]. \quad (4)$$

Applying the same weights to $x[n-1]$, $x[n]$, $x[n+1]$, $x[n+2]$ gives an estimate for $x(n+\varepsilon)$ and applying the weights in reverse order gives an estimate for $x(n+1-\varepsilon)$.

Equation (4) is also a discrete inner product that can be expressed in the frequency domain as $$x(\varepsilon) \approx \frac{1}{2\pi} \int_{-\pi}^{+\pi} X(\omega)[w_{-1}(\varepsilon)e^{j\omega}+w_0(\varepsilon)+w_1(\varepsilon)e^{-j\omega}+w_2(\varepsilon)e^{-2j\omega}]d\omega. \quad (5)$$

Equation (5) would give the same result as Eq. (3) (i.e., exact harmonic interpolation) if $$w_{-1}(\varepsilon)e^{j\omega}+w_0(\varepsilon)+w_1(\varepsilon)e^{-j\omega}+w_2(\varepsilon)e^{-2j\omega}=e^{-j\omega\varepsilon}. \quad (6)$$

However, equality for all bi is not attainable in Eq. (6) when $\varepsilon \neq 0$, so a least-square-error fit is appropriate. Since the exponential functions $e^{j\omega}$, 1, $e^{-j\omega}$, $e^{-2j\omega}$ are orthogonal on the interval $[-\pi, +\pi]$, the coefficients of this fit are given by $$w_k(\varepsilon) = \frac{1}{2\pi} \int_{-\pi}^{+\pi} e^{j\omega(\varepsilon-k)} d\omega = \frac{\sin(\pi(\varepsilon-k))}{\pi(\varepsilon-k)}. \quad (7)$$

This results in an imperfect interpolation that is characterized by the frequency response $$\frac{w_{-1}(\varepsilon)e^{j\omega}+w_0(\varepsilon)+w_1(\varepsilon)e^{-j\omega}+w_2(\varepsilon)e^{-2j\omega}}{e^{-j\omega\varepsilon}}. \quad (8)$$

The real and imaginary parts of this distortion are shown in FIG. 24 for $\varepsilon=0.0$, 0.1, 0.2, 0.3, 0.4, and 0.5. There is no distortion at all when $\varepsilon=0.0$, but the distortion increases as $\varepsilon$ increases and is largest when $\varepsilon=0.5$. This distortion is caused by the discontinuity in the imaginary part of $e^{-j\omega\varepsilon}$ as $\omega$ wraps around from $-\pi$ to $+\pi$. The value of the numerator in Eq. (8) is always the same at $-\pi$ as the value at $+\pi$ and, consequently, the fitted approximation to Eq. (6) becomes less accurate as the discontinuity increases (i.e., as $\varepsilon \to 0.5$).

The effect of the discontinuity may be reduced by fitting the interpolation coefficients to $W(\omega)e^{-j\omega\varepsilon}$ rather than $e^{-j\omega\varepsilon}$, where $W(\omega)$ is a symmetric window function that tapers off as $\omega \to \pm\pi$. Four-point interpolations can reproduce the frequency response $W(\omega) e^{-j\omega\varepsilon}$ with less distortion, and the response of the window $W(\omega)$ can be removed (without introducing any additional distortion) by frequency-domain prefiltering of $x[n]$ by the inverse response $1/W(\omega)$.

Selection of the function $W(\omega)$ is limited here by the requirement that the $\varepsilon=0$ interpolation response coincide with $W(\omega)$. This insures that interpolation of the prefiltered sample points will reproduce the sample values. Since $W(\omega)$ is a symmetric function the $\varepsilon=0.0$, filter weights must assign $w_2(0)=0$ and $w_1(0)=w_{-1}(0)$. This implies that the window function $W(\omega)$ must have the form $W(\omega)=\alpha+\beta \cos \omega$. Furthermore, since multiplying $W(\omega)$ by a constant scale factor does not alter the interpolation, the value of $W(0)$ can be assumed to be 1, and this implies that $\beta=\alpha-1$. Thus, the choice of $W(\omega)$ is reduced to the one-parameter family of functions $$W_\alpha(\omega)=\alpha+(1-\alpha)\cos \omega. \quad (9)$$

For each $\varepsilon$, the coefficients $w_{-1}(\varepsilon)$, $w_0(\varepsilon)$, $w_1(\varepsilon)$, $w_2(\varepsilon)$ are selected to minimize the square error in the approximation $$w_{-1}(\varepsilon)e^{j\omega}+w_0(\varepsilon)+w_1(\varepsilon)e^{-j\omega}+w_2(\varepsilon)e^{-2j\omega} \approx W_\alpha(\omega)e^{-j\omega\varepsilon}. \quad (10)$$

This minimization problem has solution $$\begin{aligned}
w_k(\varepsilon) &= \frac{1}{2\pi} \int_{-\pi}^{+\pi} [\alpha + (1-\alpha)\cos\omega]e^{-j\omega(\varepsilon-k)} d\omega \\
&= \alpha\left[\frac{1}{2\pi} \int_{-\pi}^{+\pi} e^{-j\omega(\varepsilon-k)} d\omega\right] + \frac{1-\alpha}{2}\left[\frac{1}{2\pi} \int_{-\pi}^{+\pi} e^{-j\omega(\varepsilon-k-1)} d\omega + \frac{1}{2\pi} \int_{-\pi}^{+\pi} e^{-j\omega(\varepsilon-k+1)} d\omega\right] \\
&= \alpha\left[\frac{\sin(\pi(\varepsilon-k))}{\pi(\varepsilon-k)}\right] + \frac{1-\alpha}{2}\left[\frac{\sin(\pi(\varepsilon-k-1))}{\pi(\varepsilon-k-1)} + \frac{\sin(\pi(\varepsilon-k+1))}{\pi(\varepsilon-k+1)}\right].
\end{aligned} \quad (11)$$

The frequency response of the distortion for this interpolation scheme is $$\frac{w_{-1}(\varepsilon)e^{j\omega}+w_0(\varepsilon)+w_1(\varepsilon)e^{-j\omega}+w_2(\varepsilon)e^{-2j\omega}}{W_\alpha(\omega)e^{-j\omega\varepsilon}}. \quad (12)$$

The real and imaginary parts of this distortion are shown in FIG. 25 for $\alpha=0.552$ that was chosen (by visual inspection) to minimize distortion. The distortion in FIG. 25 is substantially less than the distortion in FIG. 24. Even the curve for the $\varepsilon=0.5$ distortion deviates from 1.0 by less than 4% for frequencies between $-0.82 \pi$ and $+0.82 \pi$.

Some further improvement can be realized by reducing the emphasis of the fit at the extreme edges of the frequency band. This may be accomplished by only minimizing the square-error in Eq. (10) over the frequency range $[-\lambda\pi, +\lambda\pi]$ where $\lambda<1$. The computations are more complicated because the exponentials $e^{j\omega}$, 1, $e^{-j\omega}$, $e^{-2j\omega}$ are not orthogonal on this range. The solution is expressed in matrix form as $$\begin{pmatrix} w_{-1}(\varepsilon) \\ w_0(\varepsilon) \\ w_1(\varepsilon) \\ w_2(\varepsilon) \end{pmatrix} = \quad (13)$$

$$\begin{pmatrix} \langle e^{j\omega}, e^{j\omega} \rangle & \langle 1, e^{j\omega} \rangle & \langle e^{-j\omega}, e^{j\omega} \rangle & \langle e^{-j2\omega}, e^{j\omega} \rangle \\ \langle e^{j\omega}, 1 \rangle & \langle 1, 1 \rangle & \langle e^{-j\omega}, 1 \rangle & \langle e^{-j2\omega}, 1 \rangle \\ \langle e^{j\omega}, e^{-j\omega} \rangle & \langle 1, e^{-j\omega} \rangle & \langle e^{-j\omega}, e^{-j\omega} \rangle & \langle e^{-j2\omega}, e^{-j\omega} \rangle \\ \langle e^{j\omega}, e^{-j2\omega} \rangle & \langle 1, e^{-j2\omega} \rangle & \langle e^{-j\omega}, e^{-j2\omega} \rangle & \langle e^{-j2\omega}, e^{-j2\omega} \rangle \end{pmatrix}^{-1} \times$$

$$\begin{pmatrix} \langle W_\alpha(\omega)e^{-j\varepsilon\omega}, e^{j\omega} \rangle \\ \langle W_\alpha(\omega)e^{-j\varepsilon\omega}, 1 \rangle \\ \langle W_\alpha(\omega)e^{-j\varepsilon\omega}, e^{-j\omega} \rangle \\ \langle W_\alpha(\omega)e^{-j\varepsilon\omega}, e^{-2j\omega} \rangle \end{pmatrix},$$

where $$\langle e^{-jl\omega}, e^{-jk\omega} \rangle = \frac{1}{2\pi\lambda} \int_{-\lambda\pi}^{+\lambda\pi} e^{-j(l-k)\omega} d\omega = \frac{\sin(\lambda\pi(l-k))}{\lambda\pi(l-k)} \quad (14)$$

and $$\langle W_\alpha(\omega)e^{-j\varepsilon\omega}, e^{-jk\omega} \rangle = \quad (15)$$

$$\frac{1}{2\pi\lambda} \int_{-\lambda\pi}^{+\lambda\pi} [\alpha + (1-\alpha)\cos\omega]e^{-j\omega(\varepsilon-k)} d\omega = \alpha \left[ \frac{1}{2\pi} \int_{-\lambda\pi}^{+\lambda\pi} e^{-j\omega(\varepsilon-k)} d\omega \right] +$$

$$\frac{1-\alpha}{2} \left[ \frac{1}{2\pi} \int_{-\lambda\pi}^{+\lambda\pi} e^{-j\omega(\varepsilon-k-1)} d\omega + \frac{1}{2\pi} \int_{-\lambda\pi}^{+\lambda\pi} e^{-j\omega(\varepsilon-k+1)} d\omega \right] =$$

$$\lambda \left\{ \alpha \left[ \frac{\sin(\lambda\pi(\varepsilon-k))}{\lambda\pi(\varepsilon-k)} \right] + \frac{1-\alpha}{2} \left[ \frac{\sin(\lambda\pi(\varepsilon-k-1))}{\lambda\pi(\varepsilon-k-1)} + \frac{\sin(\lambda\pi(\varepsilon-k+1))}{\lambda\pi(\varepsilon-k+1)} \right] \right\}$$

and the real and imaginary parts of the distortion that result from the weights obtained for $\lambda=0.8$, $\alpha=0.56$ (also chosen by visual inspection to minimize distortion) are shown in FIG. 26.

This distortion should be acceptable for interpolations used in scattering calculations. However, if greater accuracy is required, then harmonic doubling of the sampling rate may be applied prior to the application of the prefiltered interpolation technique described above. In that case, the frequency response of the interpolated samples will be limited to the range $-\pi/2 \leq \omega \leq \pi/2$ where the distortion in FIG. 26 is essentially negligible.

It will be appreciated that variants of the above-disclosed and other features and functions, or alternatives thereof, may be combined into many other different systems or applications. Various presently unforeseen or unanticipated alternatives, modifications, variations, or improvements therein may be subsequently made by those skilled in the art which are also intended to be encompassed by the following claims.

What is claimed is:

1. A device for volumetric ultrasound imaging comprising:
    a transducer array, substantially configured in the shape of a faceted hemisphere to form a volumetric imaging region within a cavity of the faceted hemisphere, including transducer elements that transmit ultrasound signals to and receive ultrasound signals from a scattering object within the faceted hemisphere; and
    a plurality of data-acquisition assemblies, each connected to the transducer array, configured to simultaneously transmit the received ultrasound signals in parallel to a network of processors, the network of processors comprising:
    a plurality of acquisition and computation nodes, each comprising one or more graphical processing units (GPUs) that receive the received ultrasound signals in parallel and process the received ultrasound signals in parallel to obtain pulse-echo responses and reconstruct a volumetric image of the scattering object within the imaging region; and
    a control node that independently assigns delays to each transducer element and coordinates firing sequences and sampling intervals of the transducer elements to co-register the pulse-echo responses.

2. The device of claim 1, wherein the transducer elements are arranged across the surface of a plurality of triangular planar facets.

3. The device of claim 2, wherein some of the triangular planar facets are equilateral triangles and some of the triangular planar facets are isosceles triangles.

4. The device of claim 3, wherein:
    the isosceles triangles are arranged to form pentagonal transducer element assemblies; and
    the pentagonal transducer element assemblies and the equilateral triangles are arranged to form the faceted hemisphere.

5. The device of claim 2, wherein the transducer elements are arranged pseudorandomly across the surfaces of the triangular planar facets.

6. The device of claim 1, wherein the transducer elements are piezoelectric elements.

7. The device of claim 1, wherein at least one of the transducer elements further comprises a diverging lens.

8. The device of claim 1, wherein:
    the transducer array is configured to simultaneously transmit encoded transmissions from sets of the transducer elements; and the pulse echo responses are obtained by decoding the encoded transmissions.

9. The device of claim 1, further comprising:
    hardware cables that independently transfer the received ultrasound signals from each data-acquisition assembly to each processor in parallel.

10. The device of claim 9, wherein each of the hardware cables connects one of the processors to two of the data-acquisition assemblies.

11. A method for reconstructing a volumetric ultrasound image, the method comprising:
    providing an array of transducer subarrays that are substantially configured in the shape of a faceted hemisphere to form a volumetric imaging region within a cavity of a faceted hemisphere;
    transmitting ultrasound signals to and receiving ultrasound signals from a scattering object within the imaging region by transducer elements of the transducer subarrays;
    receiving the ultrasound signals from the transducer subarrays, in parallel, by a plurality of data-acquisition assemblies connected in parallel to the transducer subarrays;
    transmitting the ultrasound signals, in parallel, by the plurality of data-acquisition assemblies to a plurality of acquisition and computation nodes of a network of processors, each acquisition and computation node including one or more graphical processing units (GPUs);

processing the received ultrasound signals in parallel, by the acquisition and computation nodes, to obtain pulse-echo responses and perform parallel construction of a volumetric image of the scattering object within the imaging region the pulse-echo responses; and coordinating firing sequences and sampling intervals of the transducer elements, by a control node of the network of processors, to co-register the pulse-echo responses.

12. The method of claim 11, wherein the transducer elements are arranged across the surface of a plurality of triangular planar facets.

13. The method of claim 12, wherein some of the triangular planar facets are equilateral triangles and some of the triangular planar facets are isosceles triangles.

14. The method of claim 13, wherein:
the isosceles triangles are arranged to form pentagonal transducer element assemblies; and
the pentagonal transducer element assemblies and the equilateral triangles are arranged to form the faceted hemisphere.

15. The method of claim 12, wherein the transducer elements are arranged pseudorandomly across the surfaces of the triangular planar facets.

16. The method of claim 11, wherein the transducer elements are piezoelectric elements.

17. The method of claim 11, wherein at least one of the transducer elements further comprises a diverging lens.

18. The method of claim 11, wherein transmitting the ultrasound signals and obtaining the pulse-echo responses comprises:
simultaneously transmitting encoded transmissions from sets of the transducer elements; and
decoding the encoded transmissions.

19. The method of claim 11, wherein the received ultrasound signals are independently transferred from each data-acquisition assembly to each processor in parallel via hardware cables.

20. The method of claim 19, wherein each of the hardware cables connects one of the processors to two of the data-acquisition assemblies.

* * * * *